United States Patent
Park et al.

(10) Patent No.: US 10,026,908 B2
(45) Date of Patent: Jul. 17, 2018

(54) HETERO-CYCLIC COMPOUND AND ORGANIC LIGHT EMITTING DEVICE USING THE SAME

(71) Applicant: HEESUNG MATERIAL LTD., Yongin, Gyeonggi-do (KR)

(72) Inventors: Geon-Yu Park, Osan-si (KR); Jae-Yeol Ma, Yongin (KR); Dong-Jun Kim, Yongin (KR); Jin-Seok Choi, Suwon (KR); Dae-Hyuk Choi, Yongin (KR); Joo-Dong Lee, Seongnam (KR)

(73) Assignee: HEESUNG MATERIAL LTD., Yongin (KR)

( * ) Notice: Subject to any disclaimer, the term of this patent is extended or adjusted under 35 U.S.C. 154(b) by 0 days.

(21) Appl. No.: 15/591,366

(22) Filed: May 10, 2017

(65) Prior Publication Data

US 2017/0331052 A1 Nov. 16, 2017

(30) Foreign Application Priority Data

May 11, 2016 (KR) ........................ 10-2016-0057679

(51) Int. Cl.
*H01L 51/00* (2006.01)
*C07D 409/14* (2006.01)
(Continued)

(52) U.S. Cl.
CPC ........ *H01L 51/0074* (2013.01); *C07D 409/14* (2013.01); *C09K 11/02* (2013.01); *C09K 11/06* (2013.01); *H01L 51/006* (2013.01); *H01L 51/0052* (2013.01); *H01L 51/0085* (2013.01); *C09K 2211/1007* (2013.01);
(Continued)

(58) Field of Classification Search
None
See application file for complete search history.

(56) References Cited

U.S. PATENT DOCUMENTS 4,356,429 A 10/1982 Tang
8,227,801 B2 7/2012 Xia et al.
(Continued)

FOREIGN PATENT DOCUMENTS

CN 104292220 A 1/2015
KR 10-2013-0018724 A 2/2013
(Continued)

OTHER PUBLICATIONS

Kuwabara et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenyl-amino)triphenylamine (m-MTDATA), as Hole-Transport Materials", Advanced Materials, 1994, vol. 6, No. 9, pp. 677-679.
Extended European Search Report issued in corresponding European Application No. 17169928.3 dated Aug. 11, 2017 (5 pages).

*Primary Examiner* — Jack Chen
(74) *Attorney, Agent, or Firm* — Birch, Stewart, Kolasch & Birch, LLP

(57) ABSTRACT

The present application provides a hetero-cyclic compound which may significantly improve a service life, efficiency, electrochemical stability, and thermal stability of an organic light emitting device, and an organic light emitting device in which the hetero-cyclic compound is contained in an organic compound layer.

10 Claims, 2 Drawing Sheets

(51) Int. Cl.
*C09K 11/02* (2006.01)
*C09K 11/06* (2006.01)
*H01L 51/50* (2006.01)

(52) U.S. Cl.
CPC ............... *C09K 2211/1029* (2013.01); *C09K 2211/185* (2013.01); *H01L 51/0058* (2013.01); *H01L 51/5056* (2013.01); *H01L 51/5072* (2013.01); *H01L 51/5092* (2013.01); *H01L 51/5096* (2013.01)

(56) References Cited

U.S. PATENT DOCUMENTS

| | | |
|---|---|---|
| 9,266,865 B2 | 2/2016 | Numata et al. |
| 2011/0260138 A1* | 10/2011 | Xia ................. C07D 405/14 257/40 |
| 2015/0014649 A1 | 1/2015 | Ma et al. |
| 2015/0171342 A1 | 6/2015 | Jung et al. |
| 2016/0118601 A1 | 4/2016 | Huh et al. |
| 2017/0213968 A1 | 7/2017 | Park et al. |
| 2017/0331052 A1* | 11/2017 | Park ................. C07D 409/14 |

FOREIGN PATENT DOCUMENTS

| | | |
|---|---|---|
| KR | 10-2013-0100236 A | 9/2013 |
| KR | 10-2015-0061975 A | 6/2015 |
| KR | 10-2016-0047837 A | 5/2016 |
| WO | WO 2016/013867 A1 | 1/2016 |

\* cited by examiner

[Figure 1]
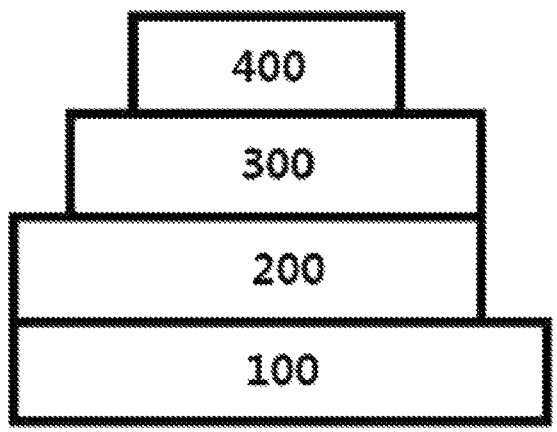
[Figure 2]
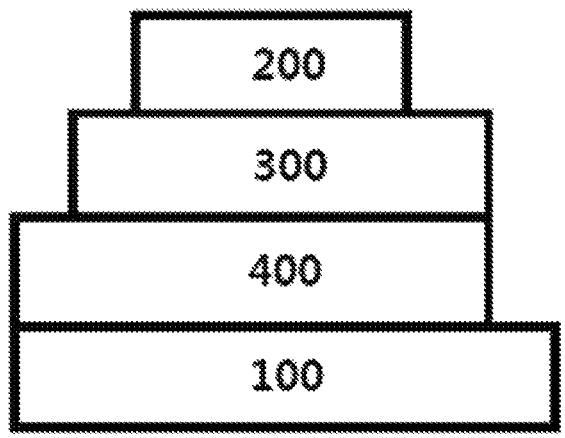

[Figure 3]
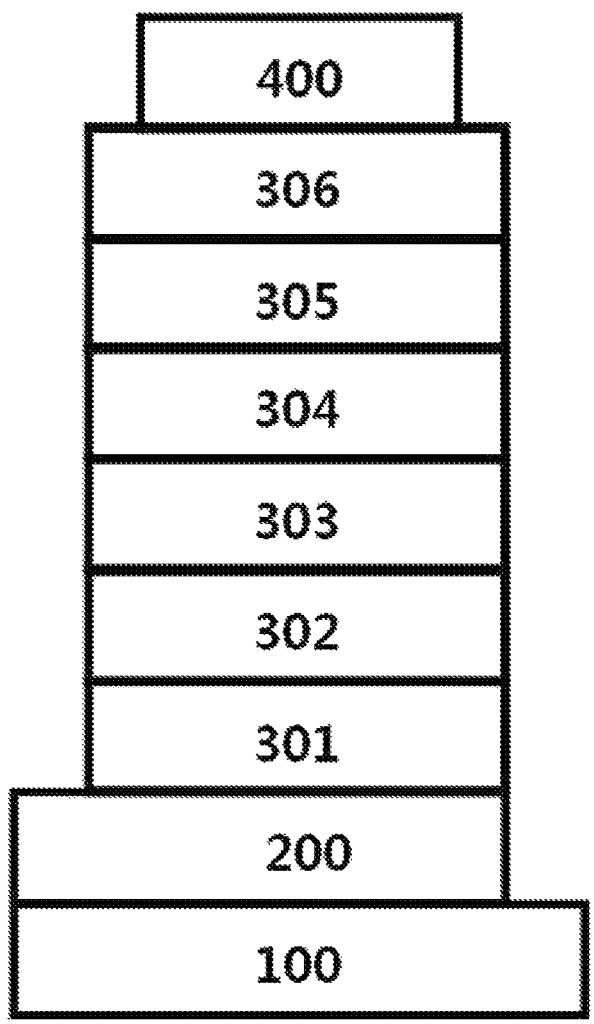

HETERO-CYCLIC COMPOUND AND ORGANIC LIGHT EMITTING DEVICE USING THE SAME

CROSS-REFERENCE TO RELATED APPLICATIONS

This application claims priority to and the benefit of Korean Patent Application No. 10-2016-0057679 filed in the Korean Intellectual Property Office on May 11, 2016, the entire contents of which are incorporated herein by reference.

TECHNICAL FIELD

The present application relates to a hetero-cyclic compound and an organic light emitting device using the same.

BACKGROUND ART

An electroluminescence device is a kind of self-emitting type display device, and has an advantage in that the viewing angle is wide, the contrast is excellent, and the response speed is fast.

An organic light emitting device has a structure in which an organic thin film is disposed between two electrodes. When a voltage is applied to an organic light emitting device having the structure, electrons and holes injected from the two electrodes combine with each other in an organic thin film to make a pair, and then, emit light while being extinguished. The organic thin film may be composed of a single layer or multi layers, if necessary.

A material for the organic thin film may have a light emitting function, if necessary. For example, as the material for the organic thin film, it is also possible to use a compound, which may itself constitute a light emitting layer alone, or it is also possible to use a compound, which may serve as a host or a dopant of a host-dopant-based light emitting layer. In addition, as a material for the organic thin film, it is also possible to use a compound, which may perform a function such as hole injection, hole transport, electron blocking, hole blocking, electron transport or electron injection.

In order to improve the performance, service life, or efficiency of the organic light emitting device, there is a continuous need for developing a material for an organic thin film.

DISCLOSURE

Technical Problem

It is necessary to perform studies on an organic light emitting device including a compound having a chemical structure, which may satisfy conditions required for a material which is available for the organic light emitting device, for example, appropriate energy levels, electrochemical stability, thermal stability, and the like, and may perform various functions required for the organic light emitting device according to the substituent.

Technical Solution

An exemplary embodiment of the present application has been made in an effort to provide a hetero-cyclic compound represented by the following Chemical Formula 1:

[Chemical Formula 1]

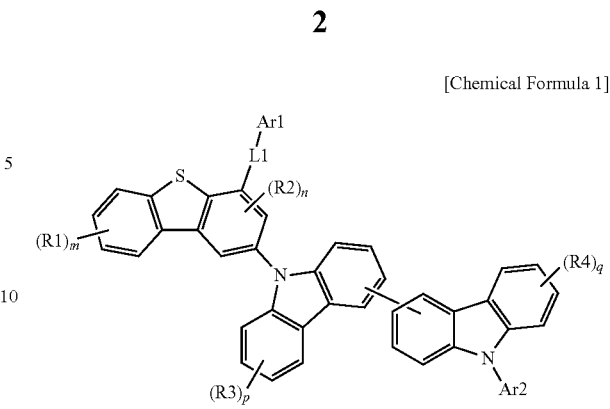

In Chemical Formula 1,

L1 is a direct bond or a substituted or unsubstituted $C_6$ to $C_{60}$ arylene group, Ar1 is a substituted or unsubstituted $C_6$ to $C_{60}$ aryl group; or a substituted or unsubstituted $C_2$ to $C_{60}$ heteroaryl group including at least one of S and O, Ar2 is a substituted or unsubstituted $C_6$ to $C_{60}$ aryl group; or a substituted or unsubstituted $C_2$ to $C_{60}$ heteroaryl group, R1 to R4 are the same as or different from each other, and are each independently selected from the group consisting of hydrogen; deuterium; a halogen group; —CN; a substituted or unsubstituted $C_1$ to $C_{60}$ alkyl group; a substituted or unsubstituted $C_2$ to $C_{60}$ alkenyl group; a substituted or unsubstituted $C_2$ to $C_{60}$ alkynyl group; a substituted or unsubstituted $C_1$ to $C_{60}$ alkoxy group; a substituted or unsubstituted $C_3$ to $C_{60}$ cycloalkyl group; a substituted or unsubstituted $C_2$ to $C_{60}$ heterocycloalkyl group; a substituted or unsubstituted $C_6$ to $C_{60}$ aryl group; a substituted or unsubstituted $C_2$ to $C_{60}$ heteroaryl group; —SiRR'R''; —P(=O)RR'; and an amine group which is unsubstituted or substituted with a $C_1$ to $C_{20}$ alkyl group, a substituted or unsubstituted $C_6$ to $C_{60}$ aryl group, or a $C_2$ to $C_{60}$ heteroaryl group, or two or more adjacent groups are bonded to each other to form a substituted or unsubstituted aliphatic or aromatic hydrocarbon ring, R, R', and R'' are the same as or different from each other, and are each independently hydrogen; deuterium; —CN; a substituted or unsubstituted $C_1$ to $C_{60}$ alkyl group; a substituted or unsubstituted $C_3$ to $C_{60}$ cycloalkyl group; a substituted or unsubstituted $C_6$ to $C_{60}$ aryl group; or a substituted or unsubstituted $C_2$ to $C_{60}$ heteroaryl group, m, p, and q are each independently an integer from 0 to 4, and n is an integer from 0 to 2.

An exemplary embodiment of the present application provides an organic light emitting device including a positive electrode, a negative electrode, and an organic material layer having one or more layers disposed between the positive electrode and the negative electrode, in which one or more layers of the organic material layer include the hetero-cyclic compound represented by Chemical Formula 1.

Advantageous Effects

A hetero-cyclic compound according to an exemplary embodiment of the present application may be used as a material for an organic material layer of an organic light emitting device. The hetero-cyclic compound may be used as a material for a hole injection layer, a hole transporting layer, a light emitting layer, an electron transporting layer, an electron injection layer, and the like in an organic light emitting device. In particular, the hetero-cyclic compound represented by Chemical Formula 1 may be used as a material for an electron transporting layer, a hole transporting layer, or a light emitting layer of an organic light emitting device. In addition, when the hetero-cyclic compound represented by Chemical Formula 1 is used for an organic light emitting device, the driving voltage of the device may be lowered, the light efficiency of the device may be improved, and the service life characteristics of the device may be improved due to the thermal stability of the compound.

DESCRIPTION OF DRAWINGS

FIGS. 1 to 3 each are views schematically illustrating a stacking structure of an organic light emitting device according to an exemplary embodiment of the present application.

REFERENCE NUMERAL

100: Substrate.
200: Positive electrode.
300: Organic material.
301: Hole injection layer.
302: Hole transporting layer.
303: Light emitting layer.
304: Hole blocking layer.
305: Electron transporting layer.
306: Electron injection layer.
400: Negative electrode.

BEST MODE

Hereinafter, the present application will be described in detail.

A hetero-cyclic compound according to an exemplary embodiment of the present application is represented by Chemical Formula 1. More specifically, the hetero-cyclic compound represented by Chemical Formula 1 may be used as a material for an organic material layer of an organic light emitting device by the structural characteristics of the core structure and the substituent as described above.

According to an exemplary embodiment of the present application, Chemical Formula 1 may be represented by any one of the following Chemical Formulae 2 to 13.

[Chemical Formula 2]

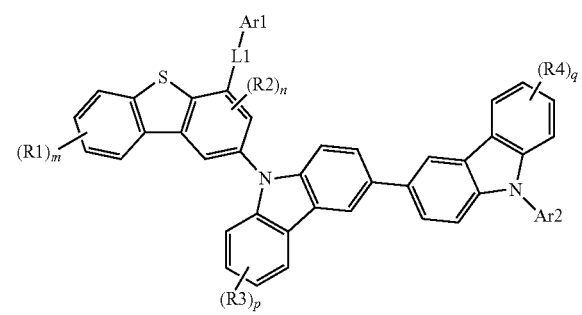

[Chemical Formula 3]

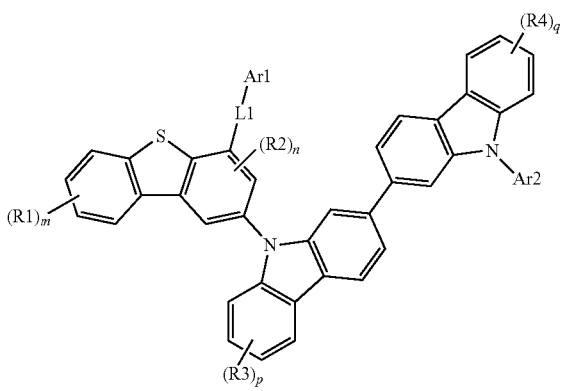

[Chemical Formula 4]

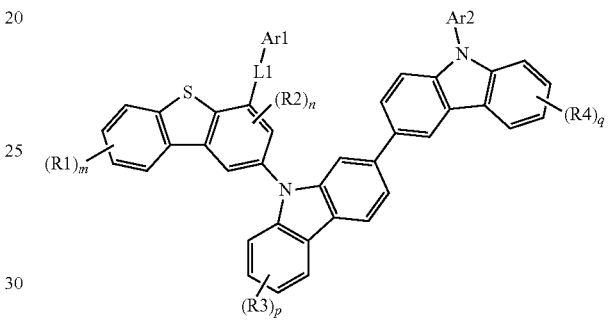

[Chemical Formula 5]

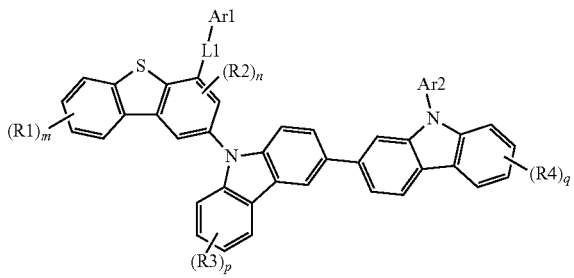

[Chemical Formula 6]

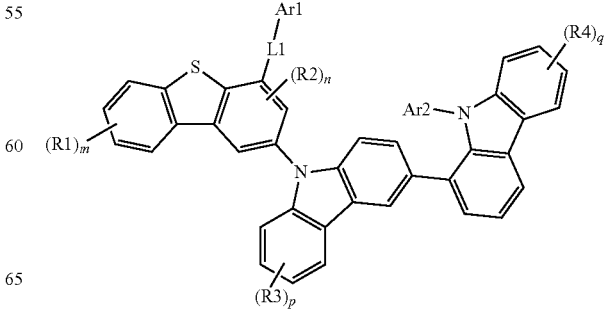

[Chemical Formula 7]

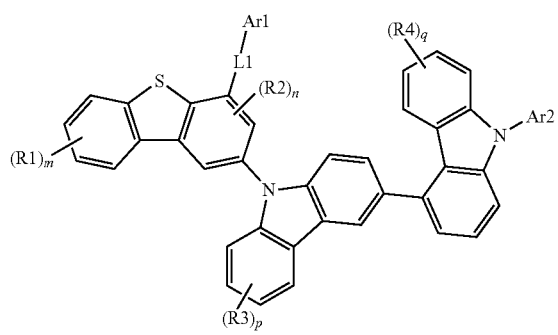

[Chemical Formula 8]

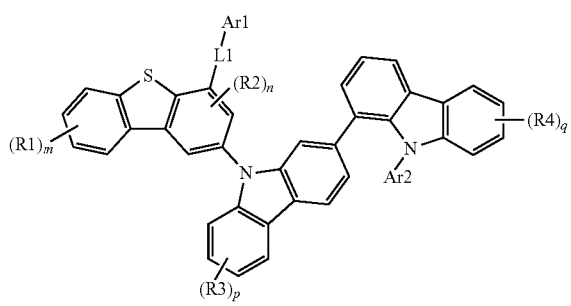

[Chemical Formula 9]

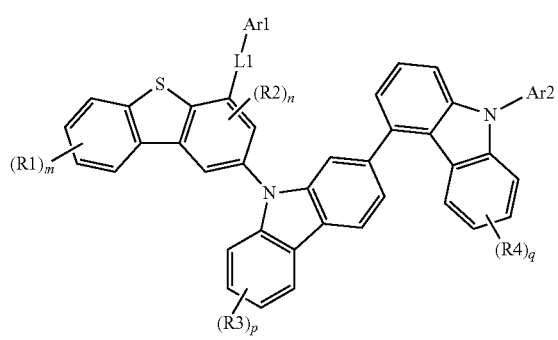

[Chemical Formula 10]

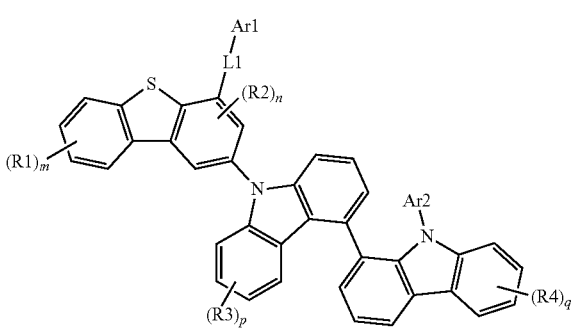

[Chemical Formula 11]

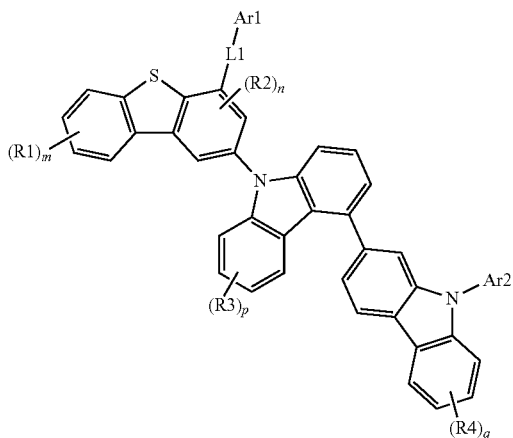

[Chemical Formula 12]

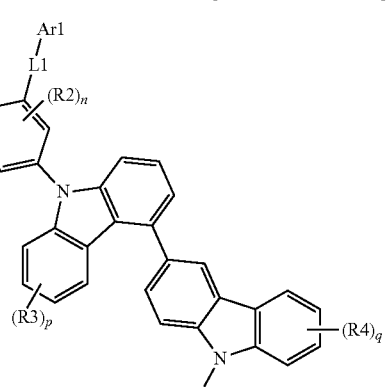

[Chemical Formula 13]

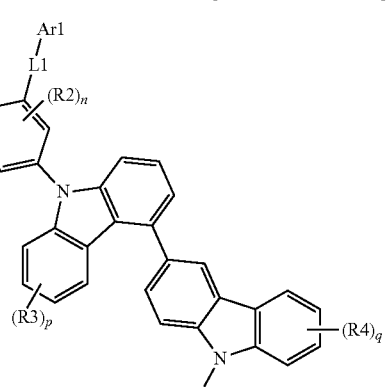

In Chemical Formulae 2 to 13, the definitions of L1, Ar1, Ar2, R1 to R4, m, n, p, and q are the same as those in Chemical Formula 1.

In an exemplary embodiment of the present application, when m, n, p, and q of Chemical Formulae 1 to 13 are each independently 2 or more, two or more R1 to R4 may be each the same as or different from each other.

In an exemplary embodiment of the present application, R1 to R4 of Chemical Formulae 1 to 13 may be each independently hydrogen or deuterium.

In an exemplary embodiment of the present application, Ar1 of Chemical Formulae 1 to 13 may be a substituted or unsubstituted $C_6$ to $C_{60}$ aryl group; a substituted or unsubstituted $C_2$ to $C_{60}$ heteroaryl group including S; or a substituted or unsubstituted $C_2$ to $C_{60}$ heteroaryl group including O.

In an exemplary embodiment of the present application, Ar1 of Chemical Formulae 1 to 13 may be a phenyl group, a biphenyl group, a naphthyl group, a fluorene group in which an alkyl group is substituted, a dibenzothiophene group, or a dibenzofuran group.

In an exemplary embodiment of the present application, Ar2 of Chemical Formulae 1 to 13 may be a substituted or unsubstituted $C_6$ to $C_{60}$ aryl group.

In an exemplary embodiment of the present application, Ar2 of Chemical Formulae 1 to 13 may be a phenyl group.

In the present application, the substituents of Chemical Formulae 1 to 13 will be more specifically described as follows.

In the present specification, "substituted or unsubstituted" means being unsubstituted or substituted with one or more substituents selected from the group consisting of deuterium; a halogen group; —CN; a $C_1$ to $C_{60}$ alkyl group; a $C_2$ to $C_{60}$ alkenyl group; a $C_2$ to $C_{60}$ alkynyl group; a $C_3$ to $C_{60}$ cycloalkyl group; a $C_2$ to $C_{60}$ heterocycloalkyl group; a $C_6$ to $C_{60}$ aryl group; a $C_2$ to $C_{60}$ heteroaryl group; —SiRR'R"; —P(=O)RR'; a $C_1$ to $C_{20}$ alkylamine group; a $C_6$ to $C_{60}$ arylamine group; and a $C_2$ to $C_{60}$ heteroarylamine group, being unsubstituted or substituted with a substituent to which two or more substituents among the substituents are bonded, or being unsubstituted or substituted with a substituent to which two or more substituents selected among the substituents are linked. For example, "the substituent to which two or more substituents are linked" may be a biphenyl group. That is, the biphenyl group may also be an aryl group, and may be interpreted as a substituent to which two phenyl groups are linked. The additional substituents may also be additionally substituted. R, R', and R" are the same as or different from each other, and are each independently hydrogen; deuterium; —CN; a substituted or unsubstituted $C_1$ to $C_{60}$ alkyl group; a substituted or unsubstituted $C_3$ to $C_{60}$ cycloalkyl group; a substituted or unsubstituted $C_6$ to $C_{60}$ aryl group; or a substituted or unsubstituted $C_2$ to $C_{60}$ heteroaryl group.

According to an exemplary embodiment of the present application, the "substituted or unsubstituted" means being unsubstituted or substituted with one or more substituents selected from the group consisting of deuterium, a halogen group, —CN, SiRR'R", P(=O)RR', a $C_1$ to $C_{60}$ straight or branched alkyl group, a $C_6$ to $C_{60}$ aryl group, and a $C_2$ to $C_{60}$ heteroaryl group, and R, R', and R" are the same as or different from each other, and are each independently hydrogen; deuterium; —CN; a $C_1$ to $C_{60}$ alkyl group which is unsubstituted or substituted with deuterium, a halogen group, —CN, a $C_1$ to $C_{60}$ alkyl group, a $C_6$ to $C_{60}$ aryl group, and a $C_2$ to $C_{60}$ heteroaryl group; a $C_3$ to $C_{60}$ cycloalkyl group which is unsubstituted or substituted with deuterium, halogen, —CN, a $C_1$ to $C_{20}$ alkyl group, a $C_6$ to $C_{60}$ aryl group, and a $C_2$ to $C_{60}$ heteroaryl group; a $C_6$ to $C_{60}$ aryl group which is unsubstituted or substituted with deuterium, halogen, —CN, a $C_1$ to $C_{20}$ alkyl group, a $C_6$ to $C_{60}$ aryl group, and a $C_2$ to $C_{60}$ heteroaryl group; or a $C_2$ to $C_{60}$ heteroaryl group which is unsubstituted or substituted with deuterium, halogen, —CN, a $C_1$ to $C_{20}$ alkyl group, a $C_6$ to $C_{60}$ aryl group, and a $C_2$ to $C_{60}$ heteroaryl group.

The term "substitution" means that a hydrogen atom bonded to a carbon atom of a compound is changed into another substituent, and a position to be substituted is not limited as long as the position is a position at which the hydrogen atom is substituted, that is, a position at which the substituent may be substituted, and when two or more are substituted, the two or more substituents may be the same as or different from each other.

In the present specification, the halogen may be fluorine, chlorine, bromine or iodine.

In the present specification, the alkyl group includes a straight-chain or branched-chain having 1 to 60 carbon atoms, and may be additionally substituted with another substituent. The number of carbon atoms of the alkyl group may be 1 to 60, specifically 1 to 40, and more specifically 1 to 20. Specific examples thereof include a methyl group, an ethyl group, a propyl group, an n-propyl group, an isopropyl group, a butyl group, an n-butyl group, an isobutyl group, a tert-butyl group, a sec-butyl group, a 1-methyl-butyl group, a 1-ethyl-butyl group, a pentyl group, an n-pentyl group, an isopentyl group, a neopentyl group, a tert-pentyl group, a hexyl group, an n-hexyl group, a 1-methylpentyl group, a 2-methylpentyl group, a 4-methyl-2-pentyl group, a 3,3-dimethylbutyl group, a 2-ethylbutyl group, a heptyl group, an n-heptyl group, a 1-methylhexyl group, a cyclopentylmethyl group, a cyclohexylmethyl group, an octyl group, an n-octyl group, a tert-octyl group, a 1-methylheptyl group, a 2-ethylhexyl group, a 2-propylpentyl group, an n-nonyl group, a 2,2-dimethylheptyl group, a 1-ethyl-propyl group, a 1,1-dimethyl-propyl group, an isohexyl group, a 2-methylpentyl group, a 4-methylhexyl group, a 5-methylhexyl group, and the like, but are not limited thereto.

In the present specification, the alkenyl group includes a straight-chain or branched-chain having 2 to 60 carbon atoms, and may be additionally substituted with another substituent. The number of carbon atoms of the alkenyl group may be 2 to 60, specifically 2 to 40, and more specifically 2 to 20. Specific examples thereof include a vinyl group, a 1-propenyl group, an isopropenyl group, a 1-butenyl group, a 2-butenyl group, a 3-butenyl group, a 1-pentenyl group, a 2-pentenyl group, a 3-pentenyl group, a 3-methyl-1-butenyl group, a 1,3-butadienyl group, an allyl group, a 1-phenylvinyl-1-yl group, a 2-phenylvinyl-1-yl group, a 2,2-diphenylvinyl-1-yl group, a 2-phenyl-2-(naphthyl-1-yl)vinyl-1-yl group, a 2,2-bis(diphenyl-1-yl)vinyl-1-yl group, a stilbenyl group, a styrenyl group, and the like, but are not limited thereto.

In the present specification, the alkynyl group includes a straight-chain or branched-chain having 2 to 60 carbon atoms, and may be additionally substituted with another substituent. The number of carbon atoms of the alkynyl group may be 2 to 60, specifically 2 to 40, and more specifically 2 to 20.

In the present specification, the cycloalkyl group includes a monocycle or polycycle having 3 to 60 carbon atoms, and may be additionally substituted with another substituent. Here, the polycycle means a group in which a cycloalkyl group is directly linked to or fused with another cyclic group. Here, another cyclic group may also be a cycloalkyl group, but may also be another kind of cyclic group, for example, a heterocycloalkyl group, an aryl group, a heteroaryl group, and the like. The number of carbon atoms of the cycloalkyl group may be 3 to 60, specifically 3 to 40, and more specifically 5 to 20. Specific examples thereof include a cyclopropyl group, a cyclobutyl group, a cyclopentyl group, a 3-methylcyclopentyl group, a 2,3-dimethylcyclopentyl group, a cyclohexyl group, a 3-methylcyclohexyl group, a 4-methylcyclohexyl group, a 2,3-dimethylcyclohexyl group, a 3,4,5-trimethylcyclohexyl group, a 4-tert-butylcyclohexyl group, a cycloheptyl group, a cyclooctyl group, and the like, but are not limited thereto.

In the present specification, the heterocycloalkyl group includes O, S, Se, N, or Si as a heteroatom, includes a monocycle or polycycle having 2 to 60 carbon atoms, and may be additionally substituted with another substituent. Here, the polycycle means a group in which a heterocycloalkyl group is directly linked to or fused with another cyclic group. Here, another cyclic group may also be a heterocycloalkyl group, but may also be another kind of cyclic group, for example, a cycloalkyl group, an aryl group, a heteroaryl group, and the like. The number of carbon atoms of the heterocycloalkyl group may be 2 to 60, specifically 2 to 40, and more specifically 3 to 20.

In the present specification, the aryl group includes a monocycle or polycycle having 6 to 60 carbon atoms, and may be additionally substituted with another substituent. Here, the polycycle means a group in which an aryl group is directly linked to or fused with another cyclic group. Here, another cyclic group may also be an aryl group, but may also be another kind of cyclic group, for example, a cycloalkyl group, a heterocycloalkyl group, a heteroaryl group, and the like. The aryl group includes a spiro group. The number of carbon atoms of the aryl group may be 6 to 60, specifically 6 to 40, and more specifically 6 to 25. Specific examples of the aryl group include a phenyl group, a biphenyl group, a triphenyl group, a naphthyl group, an anthryl group, a chrysenyl group, a phenanthrenyl group, a perylenyl group, a fluoranthenyl group, a triphenylenyl group, a phenalenyl group, a pyrenyl group, a tetracenyl group, a pentacenyl group, a fluorenyl group, an indenyl group, an acenaphthylenyl group, a benzofluorenyl group, a spirobifluorenyl group, a 2,3-dihydro-1H-indenyl group, a fused cyclic group thereof, and the like, but are not limited thereto.

In the present specification, the spiro group is a group including a spiro structure, and may have 15 to 60 carbon atoms. For example, the spiro group may include a structure in which a 2,3-dihydro-1H-indene group or a cyclohexane group is spiro-bonded to a fluorenyl group. Specifically, the spiro group may include any one of the groups of the following structural formulae.

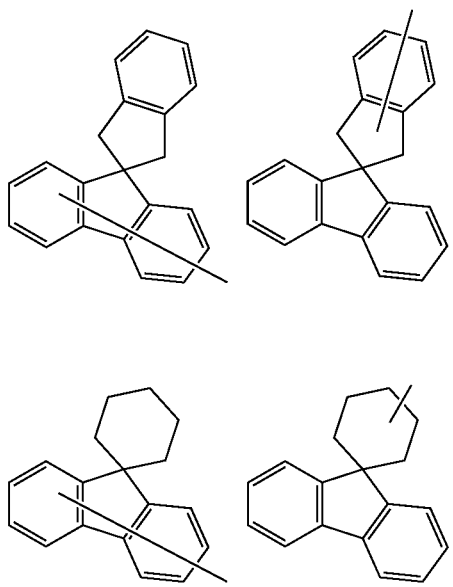

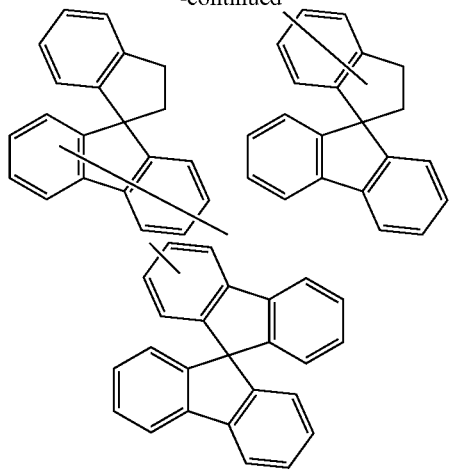

In the present specification, the heteroaryl group includes S, O, Se, N, or Si as a heteroatom, includes a monocycle or polycycle having 2 to 60 carbon atoms, and may be additionally substituted with another substituent. Here, the polycycle means a group in which a heteroaryl group is directly linked to or fused with another cyclic group. Here, another cyclic group may also be a heteroaryl group, but may also be another kind of cyclic group, for example, a cycloalkyl group, a heterocycloalkyl group, an aryl group, and the like. The number of carbon atoms of the heteroaryl group may be 2 to 60, specifically 2 to 40, and more specifically 3 to 25. Specific examples of the heteroaryl group include a pyridyl group, a pyrrolyl group, a pyrimidyl group, a pyridazinyl group, a furanyl group, a thiophene group, an imidazolyl group, a pyrazolyl group, an oxazolyl group, an isoxazolyl group, a thiazolyl group, an isothiazolyl group, a triazolyl group, a furazanyl group, an oxadiazolyl group, a thiadiazolyl group, a dithiazolyl group, a tetrazolyl group, a pyranyl group, a thiopyranyl group, a diazinyl group, an oxazinyl group, a thiazinyl group, a dioxynyl group, a triazinyl group, a tetrazinyl group, a quinolyl group, an isoquinolyl group, a quinazolinyl group, an isoquinazolinyl group, a quinoxalyl group, a naphthyridyl group, an acridinyl group, a phenanthridinyl group, an imidazopyridinyl group, a diaza naphthalenyl group, a triazaindene group, an indolyl group, an indolizinyl group, a benzothiazolyl group, a benzoxazolyl group, a benzimidazolyl group, a benzothiophene group, a benzofuran group, a dibenzothiophene group, a dibenzofuran group, a carbazolyl group, a benzocarbazolyl group, a dibenzocarbazolyl group, a phenazinyl group, a dibenzosilole group, spirobi (dibenzosilole), a dihydrophenazinyl group, a phenoxazinyl group, a phenanthridyl group, an imidazopyridinyl group, a thienyl group, an indolo[2,3-a]carbazolyl group, an indolo[2,3-b]carbazolyl group, an indolinyl group, a 10,11-dihydro-dibenzo[b,f]azepin group, a 9,10-dihydroacridinyl group, a phenanthrazinyl group, a phenothiazinyl group, a phthalazinyl group, a naphthylidinyl group, a phenanthrolinyl group, a benzo[c][1,2,5]thiadiazolyl group, a 5,10-dihydrodibenzo[b,e][1,4]azasilinyl, a pyrazolo[1,5-c]quinazolinyl group, a pyrido[1,2-b]indazolyl group, a pyrido[1,2-a]imidazo[1,2-e]indolinyl group, a 5,11-dihydroindeno[1,2-b]carbazolyl group, and the like, but are not limited thereto.

In the present specification, the amine group may be selected from the group consisting of a monoalkylamine group; a monoarylamine group; a monoheteroarylamine group; —NH$_2$; a dialkylamine group; a diarylamine group; a diheteroarylamine group; an alkylarylamine group; an alkylheteroarylamine group; and an arylheteroarylamine group, and the number of carbon atoms thereof is not particularly limited, but is preferably 1 to 30. Specific examples of the amine group include a methylamine group, a dimethylamine group, an ethylamine group, a diethylamine group, a phenylamine group, a naphthylamine group, a biphenylamine group, a dibiphenylamine group, an anthracenylamine group, a 9-methyl-anthracenylamine group, a diphenylamine group, a phenylnaphthylamine group, a ditolylamine group, a phenyltolylamine group, a triphenylamine group, a biphenylnaphthylamine group, a phenylbiphenylamine group, a biphenylfluorenylamine group, a phenyltriphenylenylamine group, a biphenyltriphenylenylamine group, and the like, but are not limited thereto.

In the present specification, an arylene group means that there are two bonding positions in an aryl group, that is, a divalent group. The above-described description on the aryl group may be applied to the arylene group, except for a divalent arylene group. Further, a heteroarylene group means that there are two bonding positions in a heteroaryl group, that is, a divalent group. The above-described description on the heteroaryl group may be applied to the heteroarylene group, except for a divalent heteroarylene group.

According to an exemplary embodiment of the present application, Chemical Formula 1 may be represented by any one of the following compounds, but is not limited thereto.

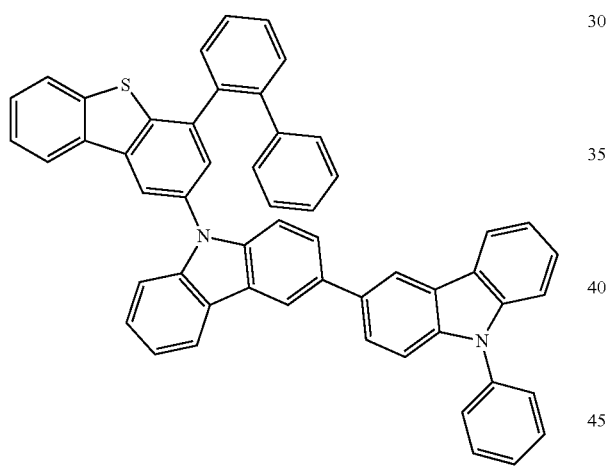

1

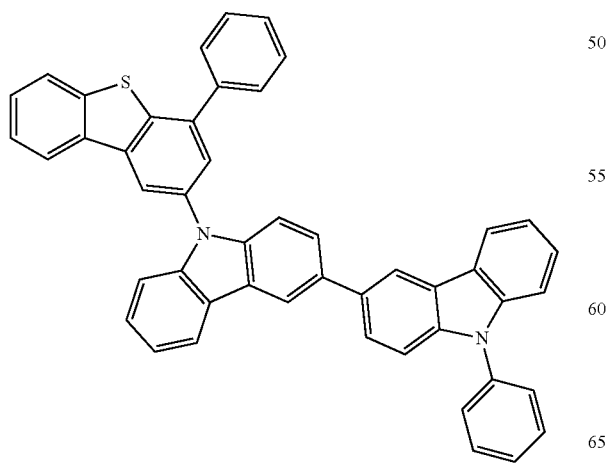

2

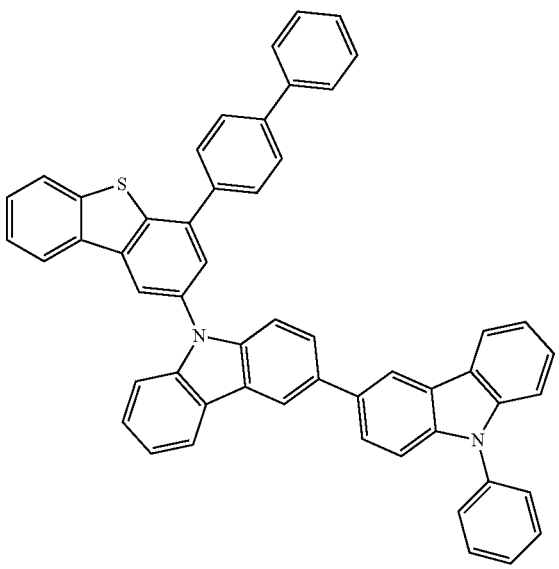

3

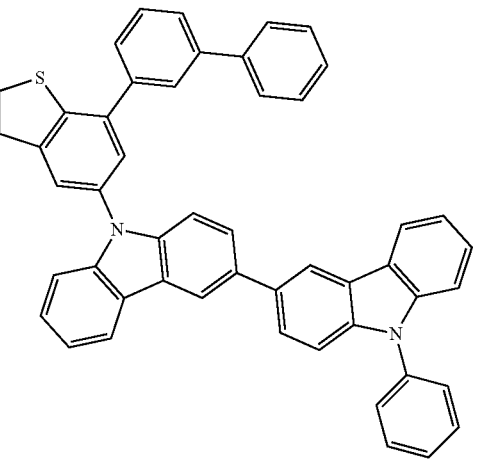

4

5

6
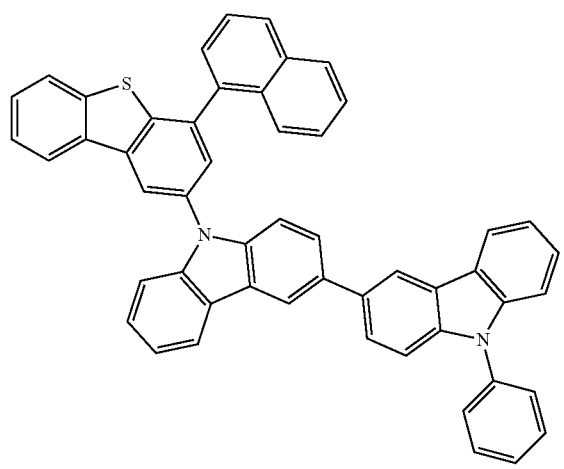
7
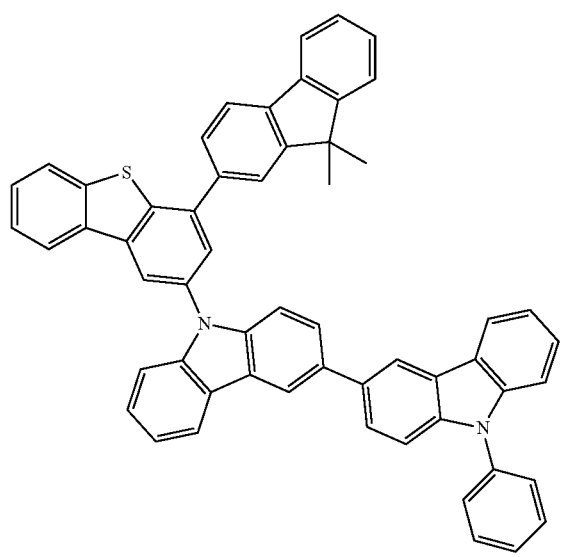
8
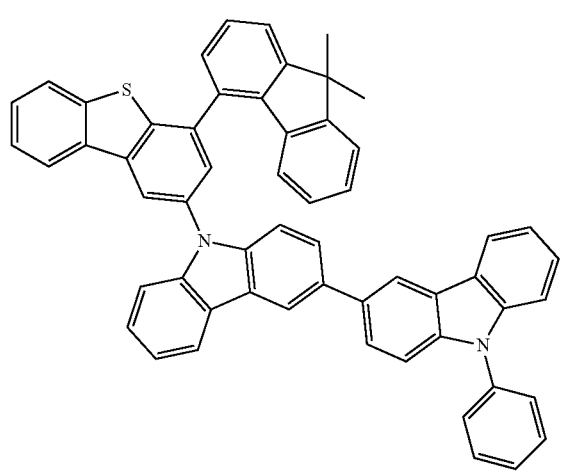
9
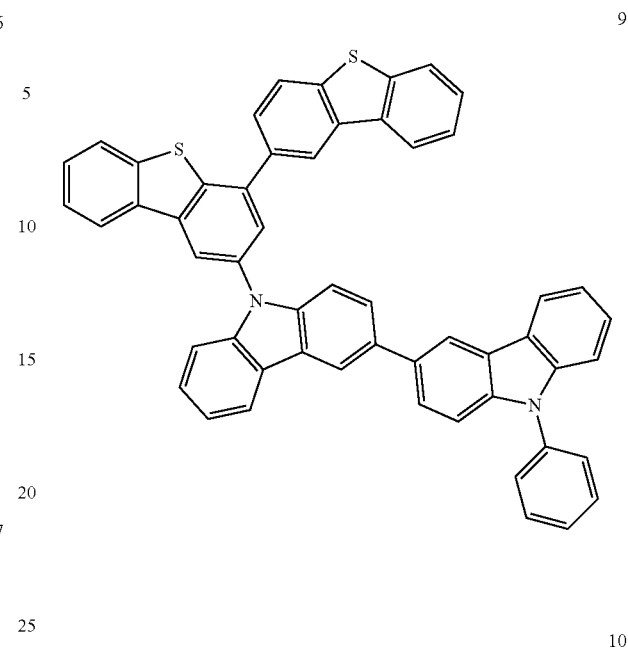
10
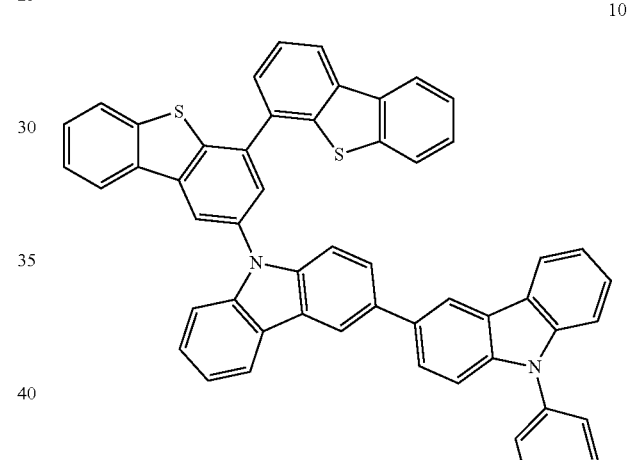
11
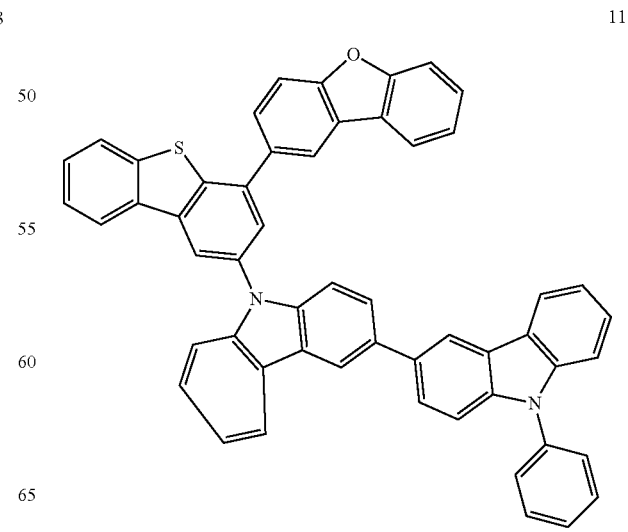

12
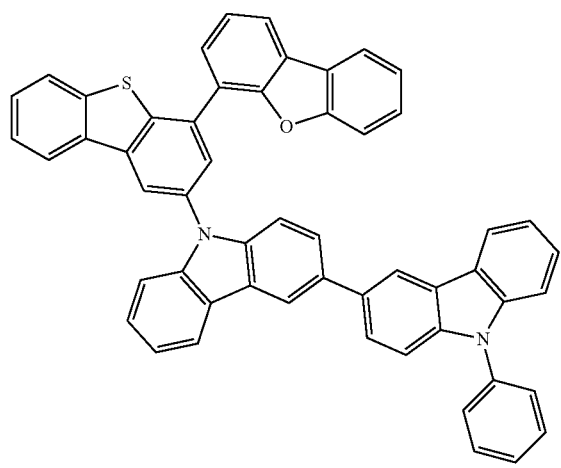
13
15
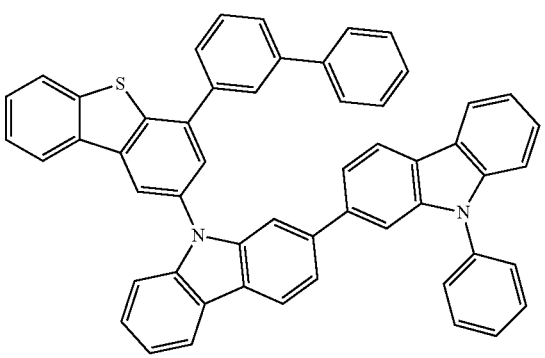
16
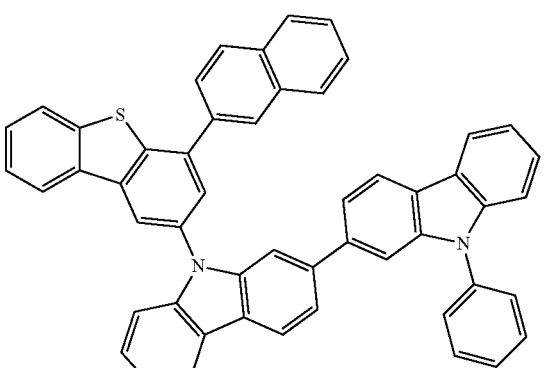
17
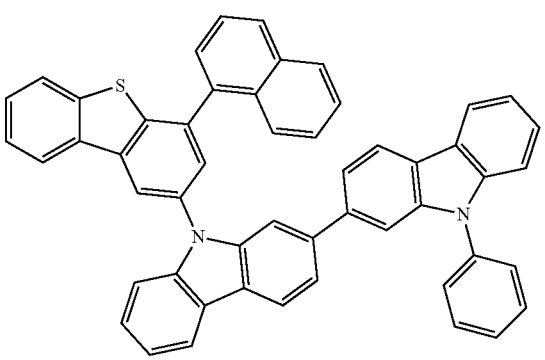
14
18
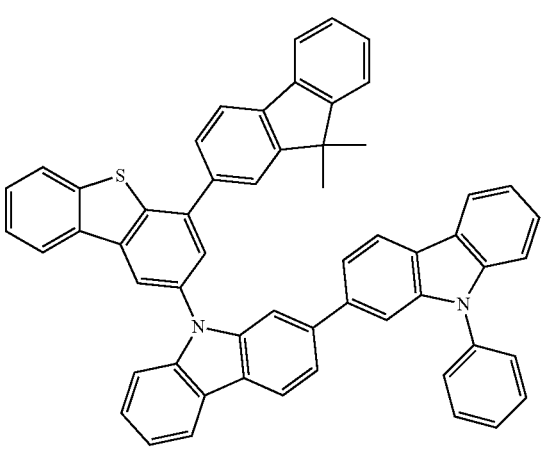

19
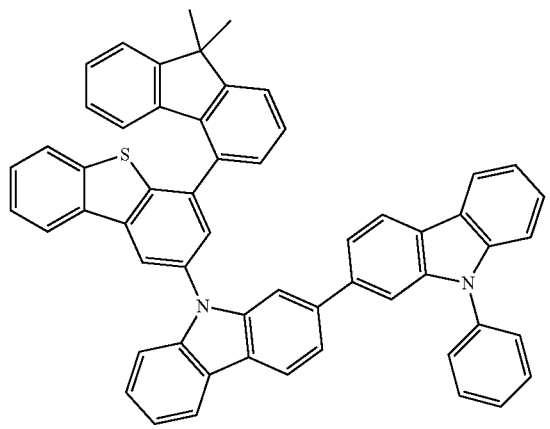
20
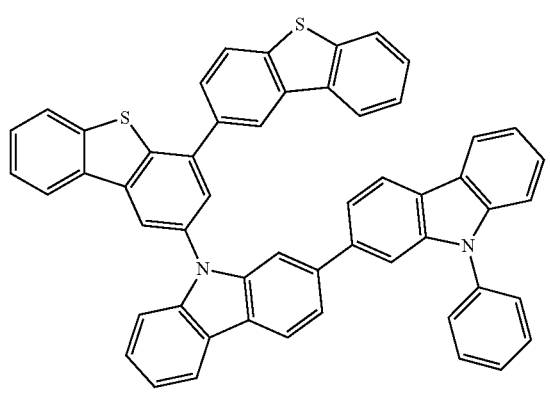
21
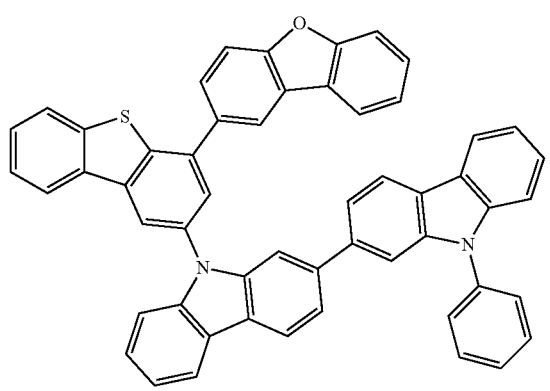
22
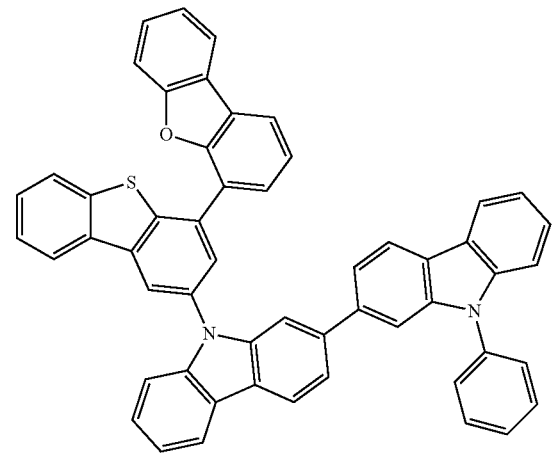
23
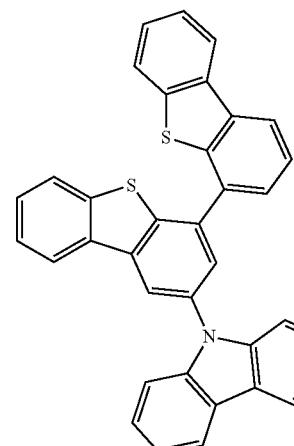
24
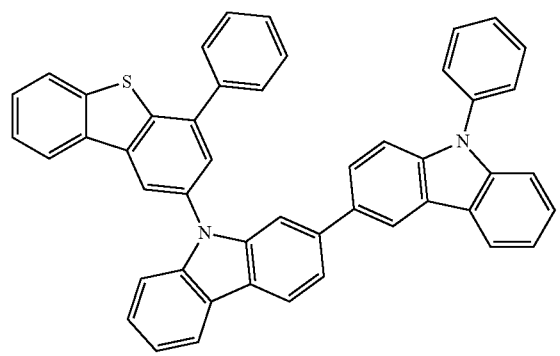

25
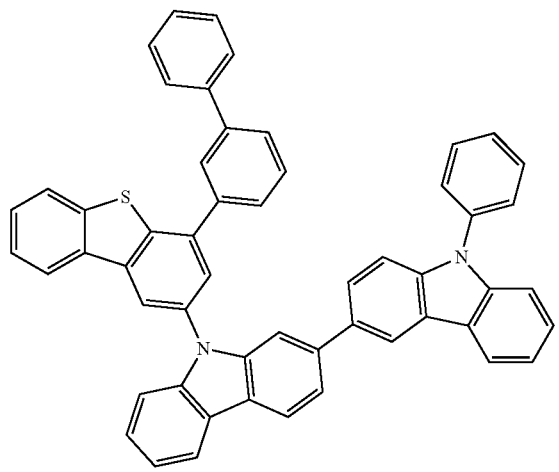
26
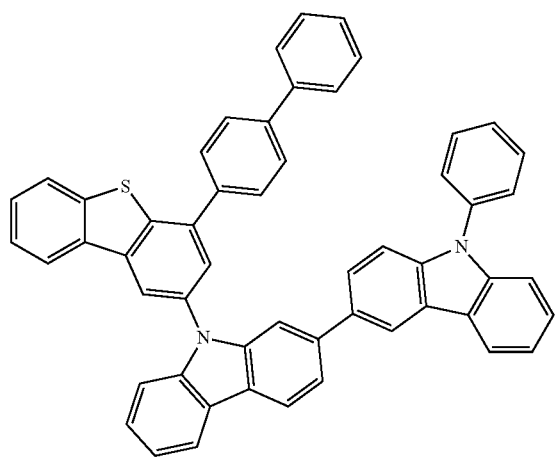
27
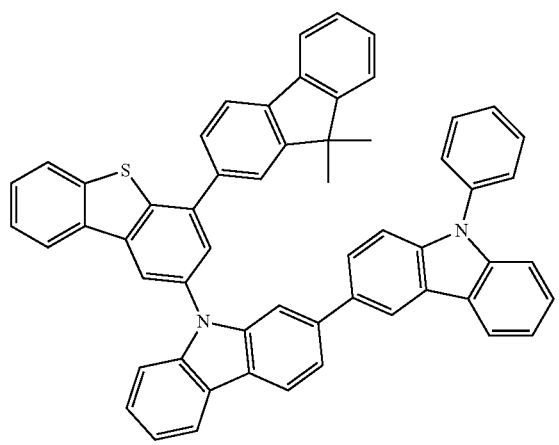
28
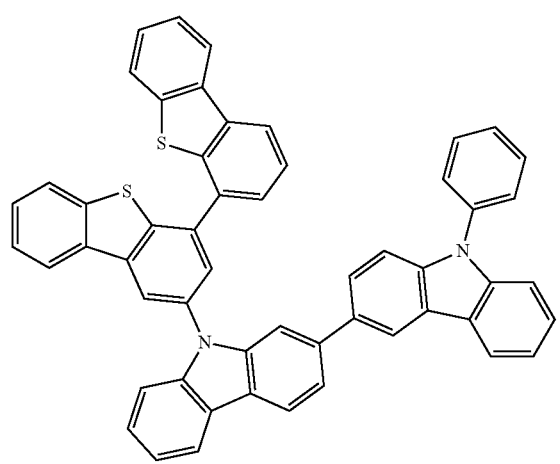
29
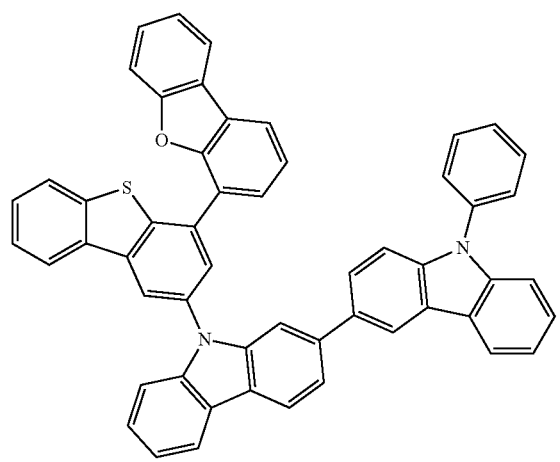
30
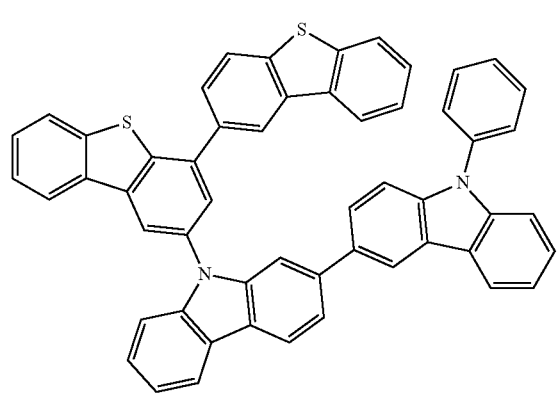

31
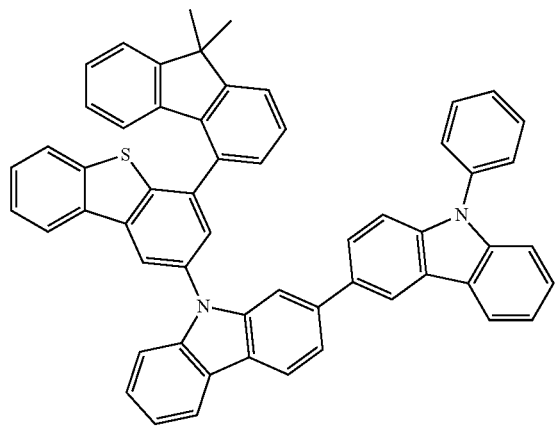
32
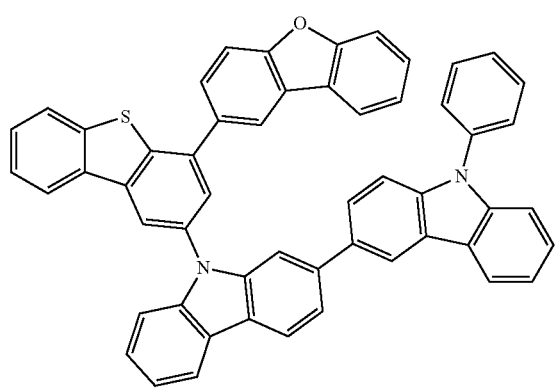
33
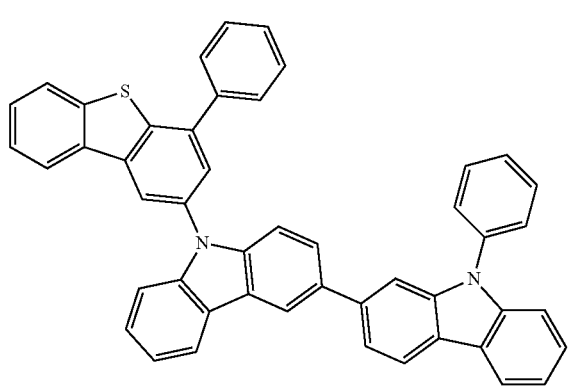
34
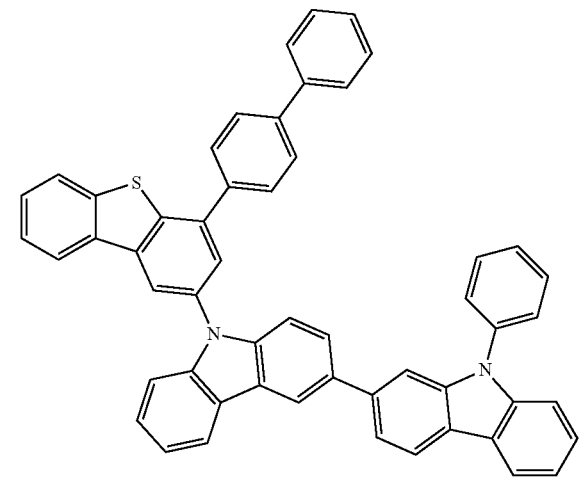
35
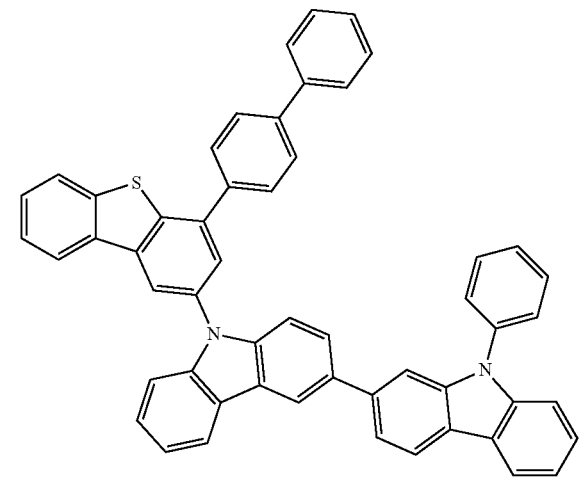
36
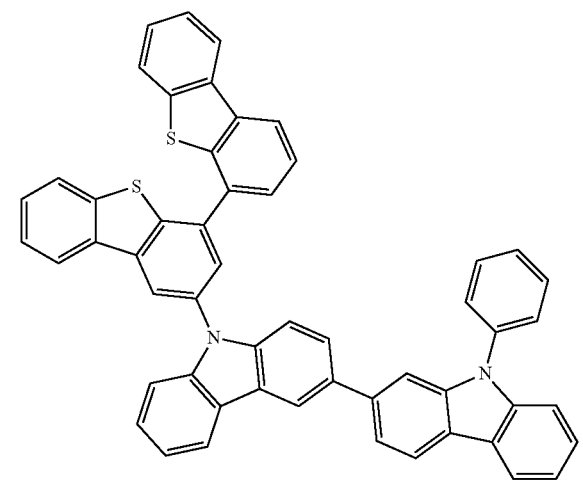

37
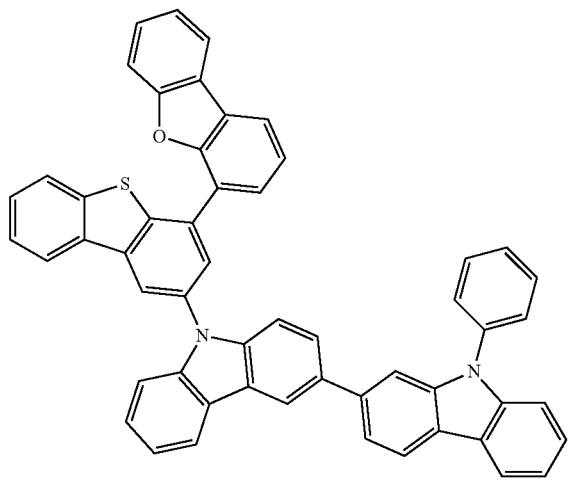
38
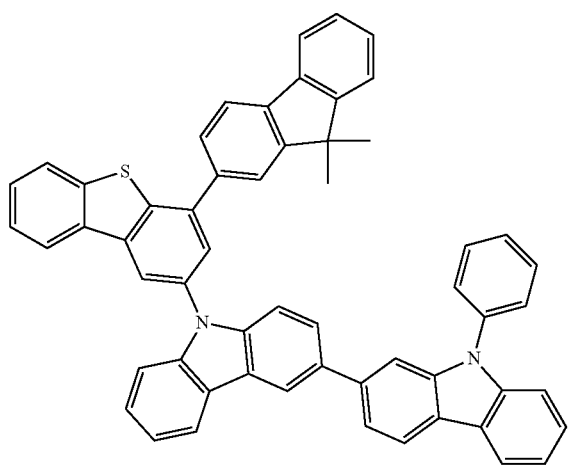
39
40
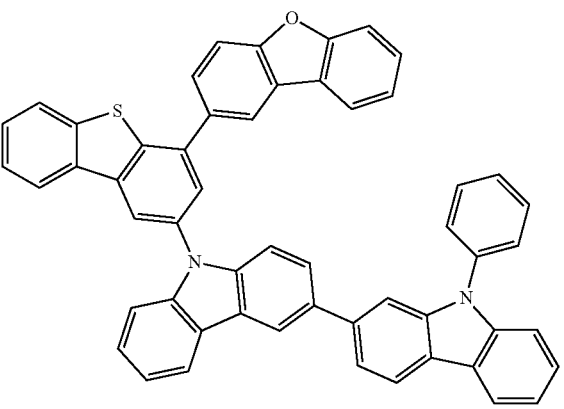
41
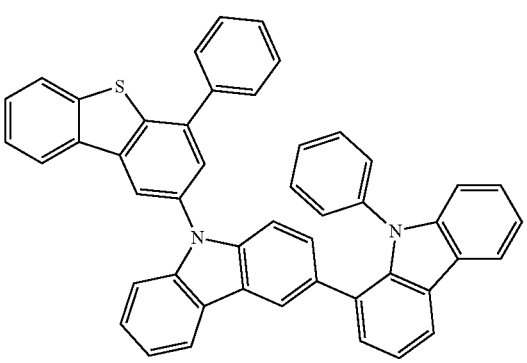
42
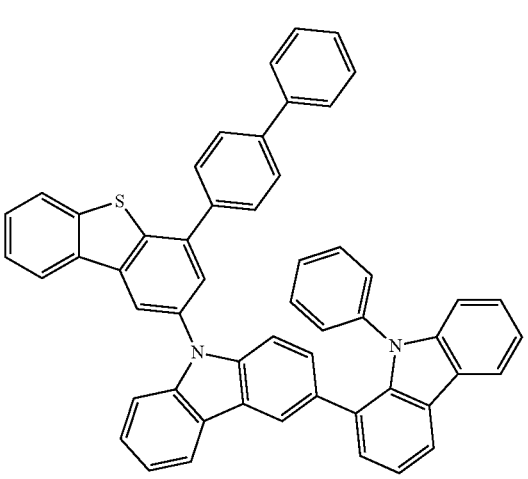
43

44
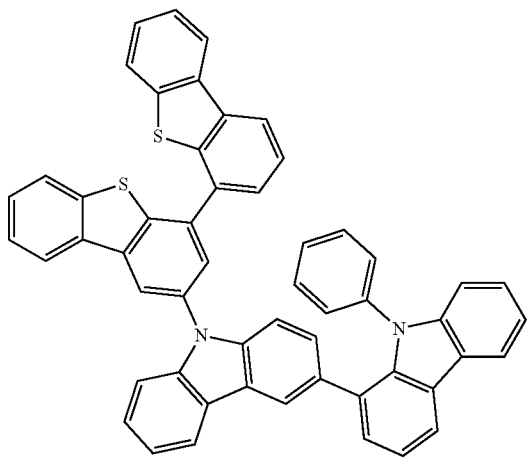
45
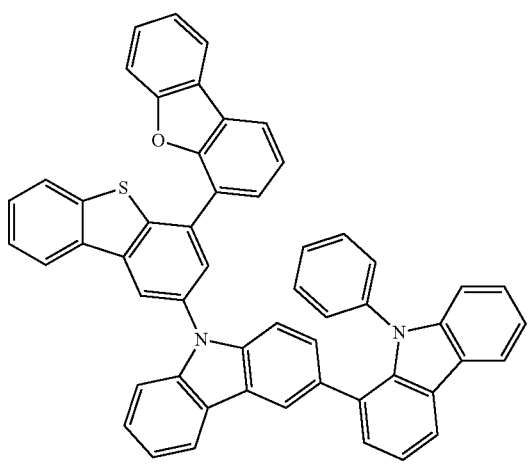
46
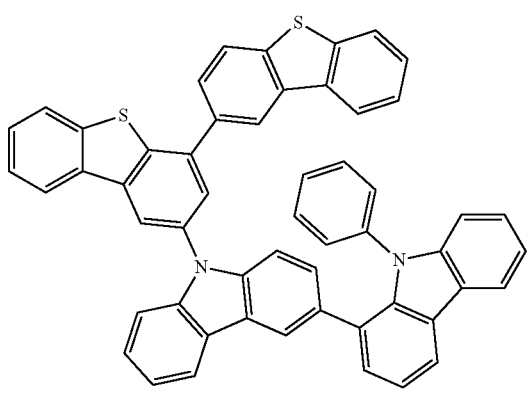
47
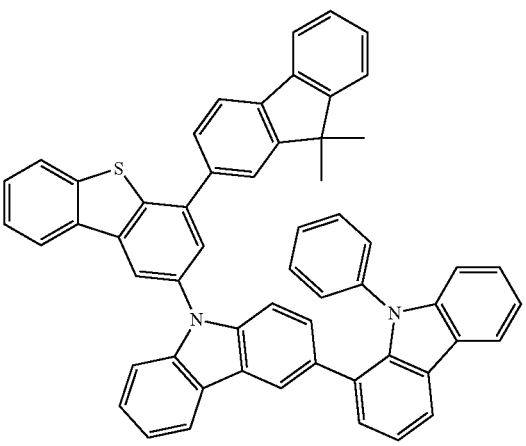
48
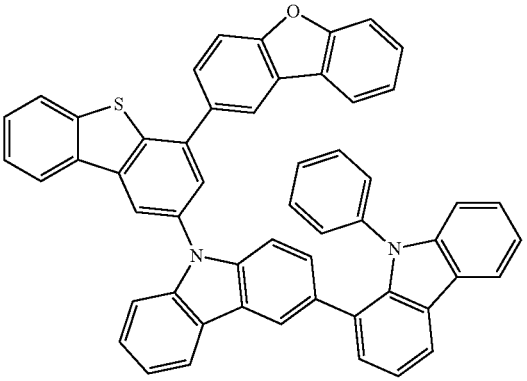
49
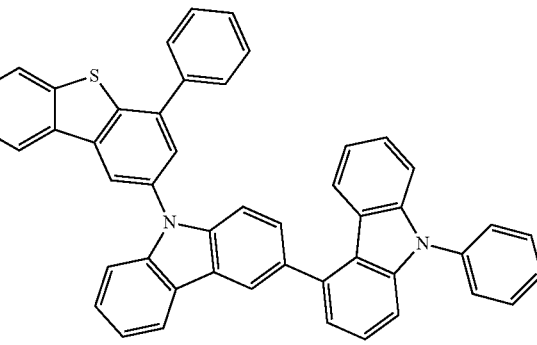

50
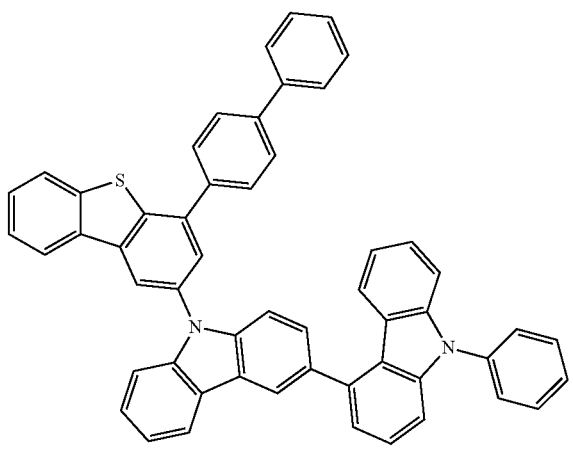
51
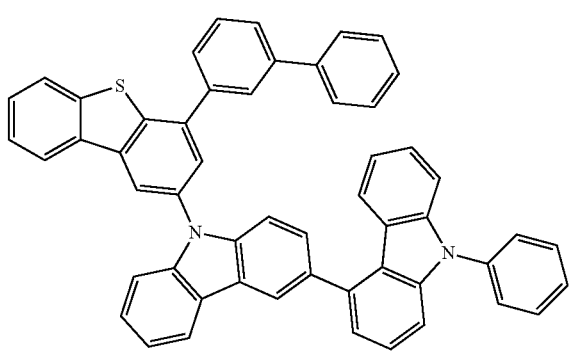
52
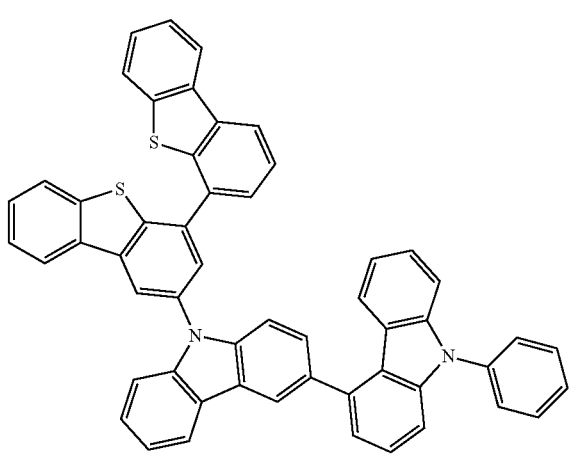
53
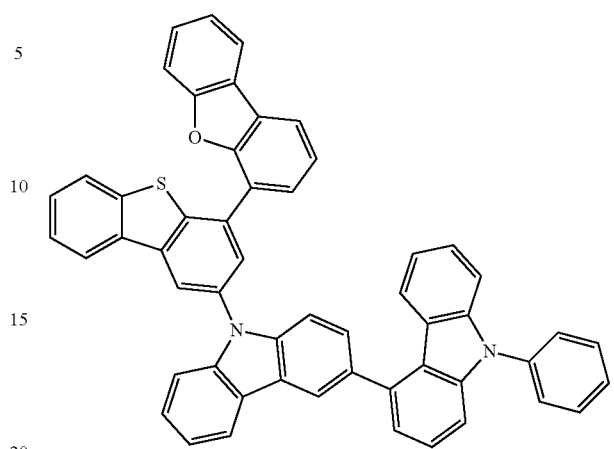
54
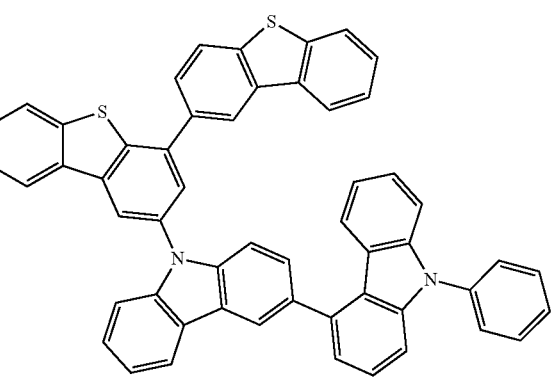
55
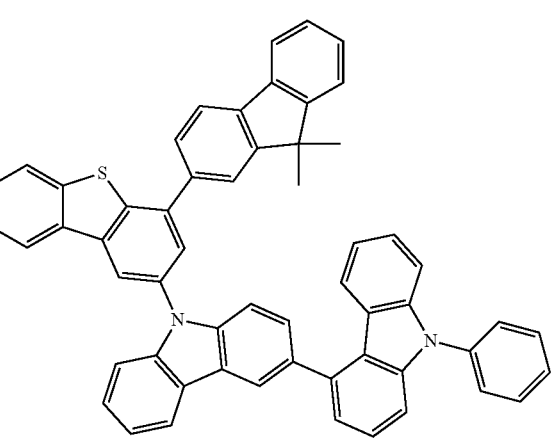

56
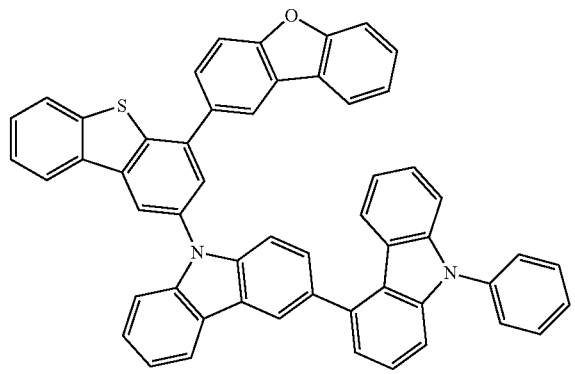
57
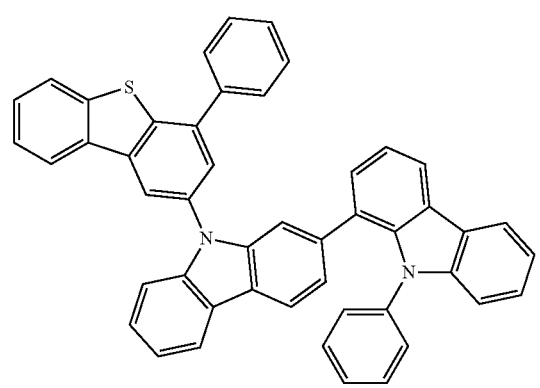
58
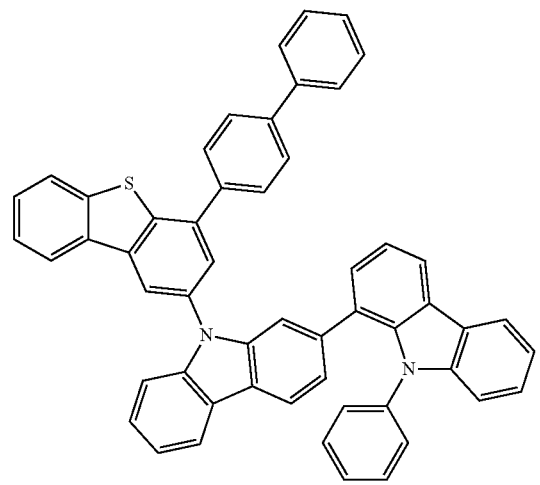
59
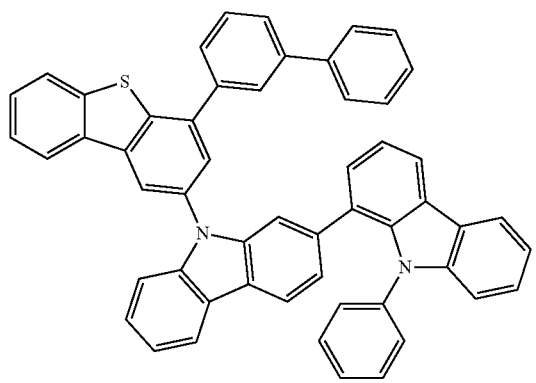
60
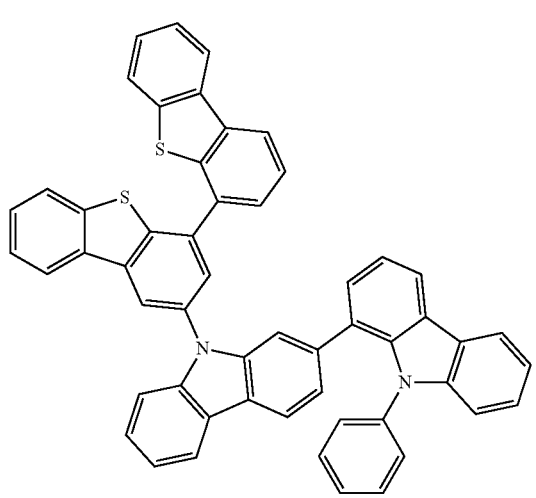
61
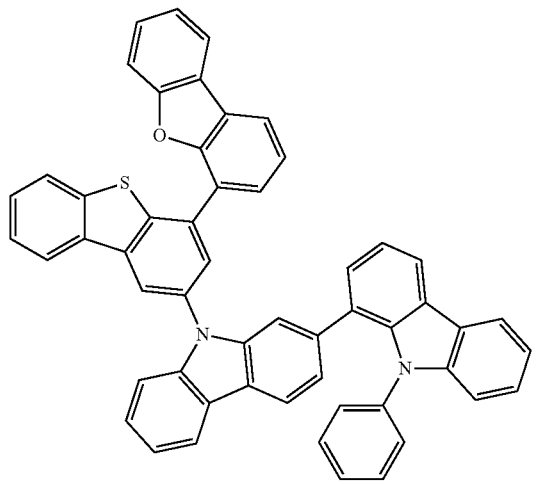

62
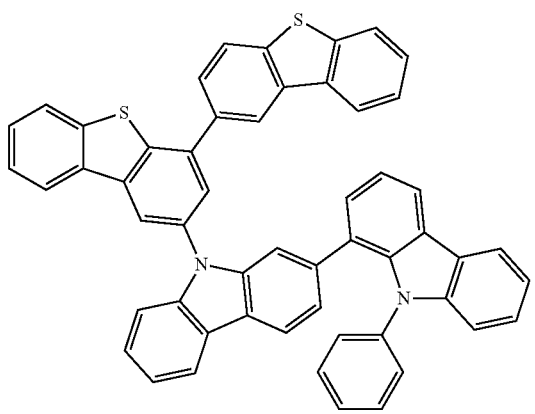
63
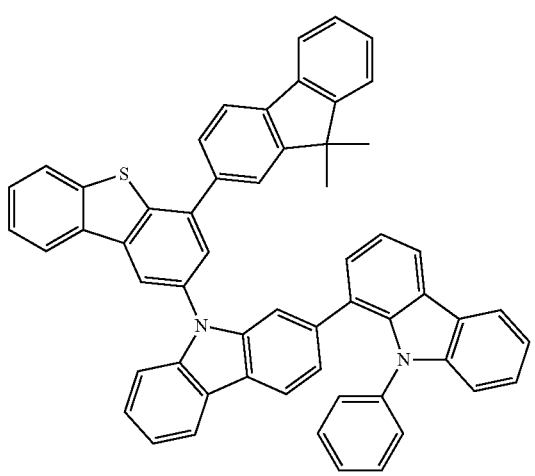
64
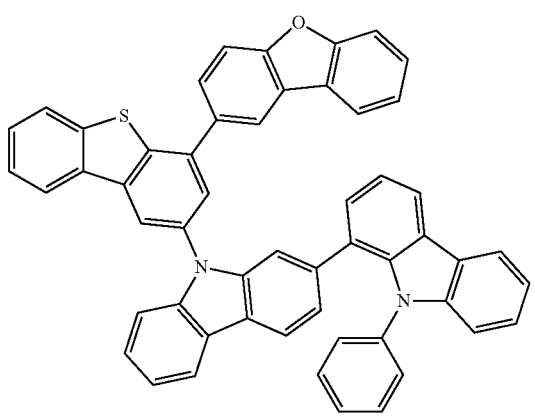
65
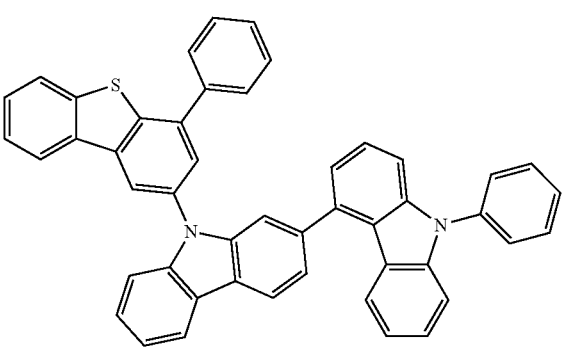
66
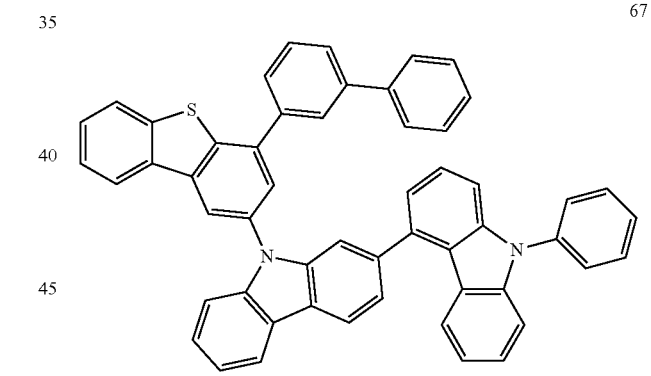
67
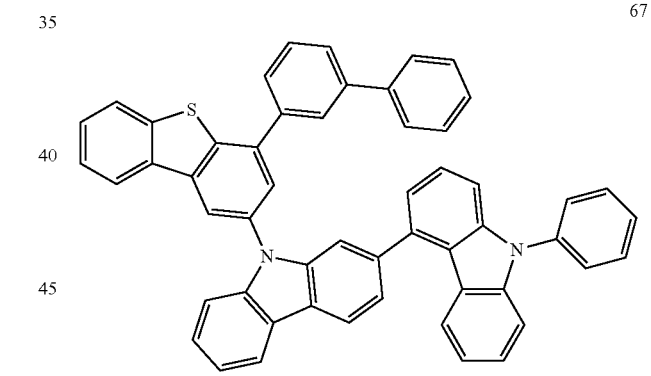
68
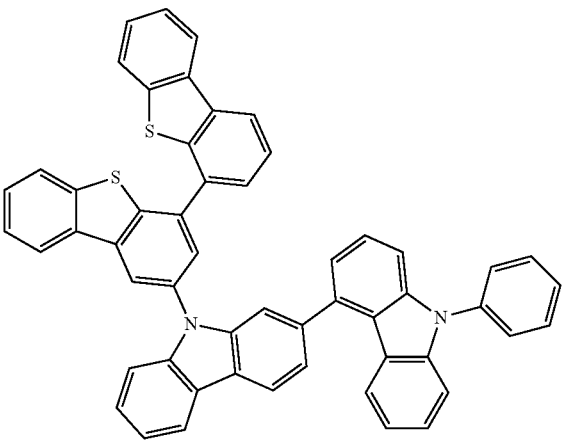

69
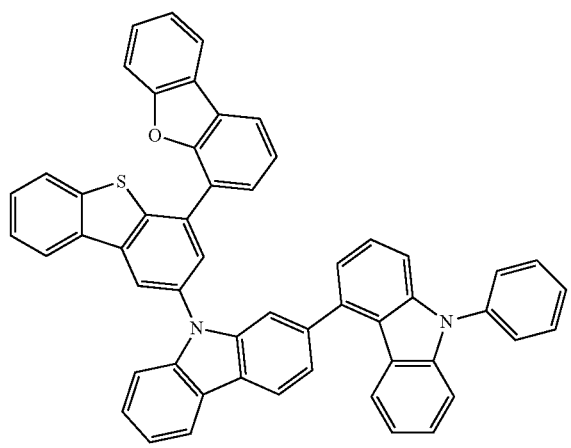
70
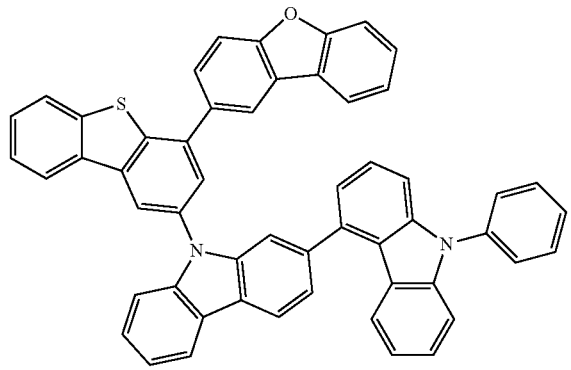
71
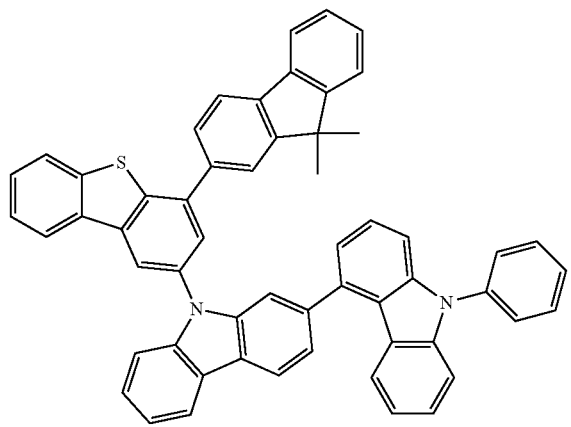
72
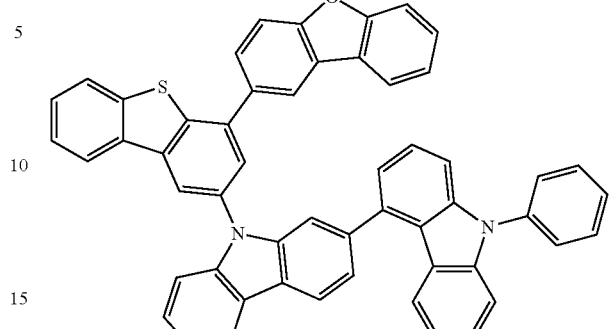
73
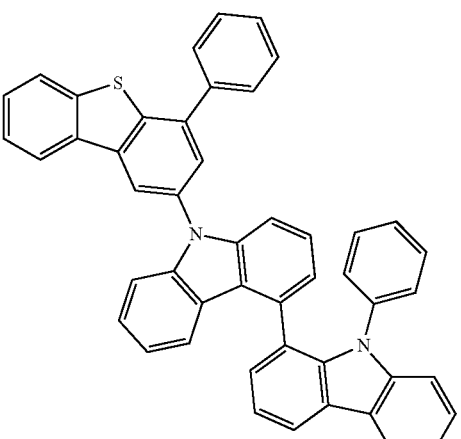
74
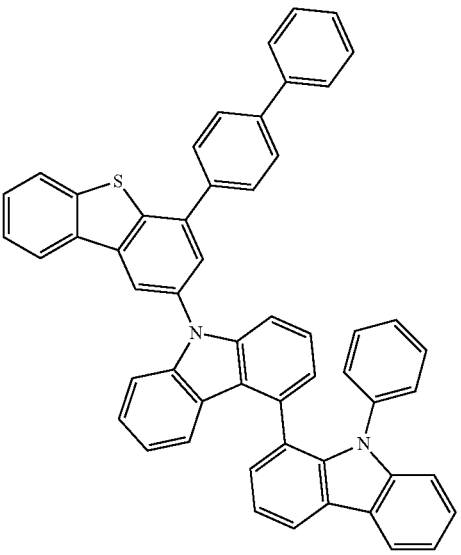

75
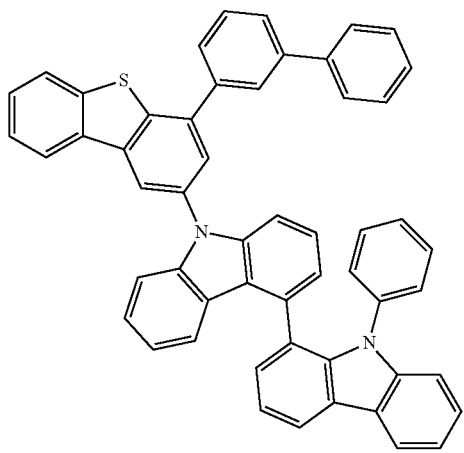
76
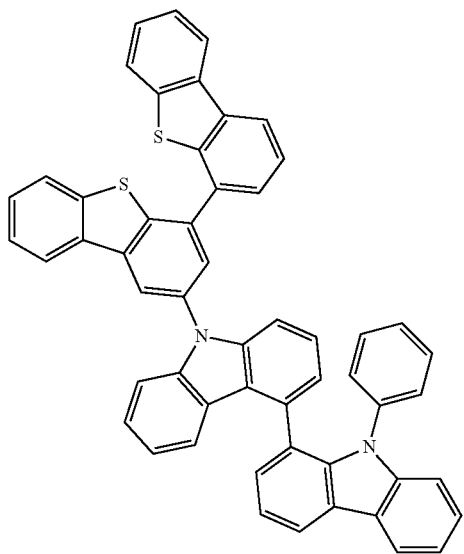
77
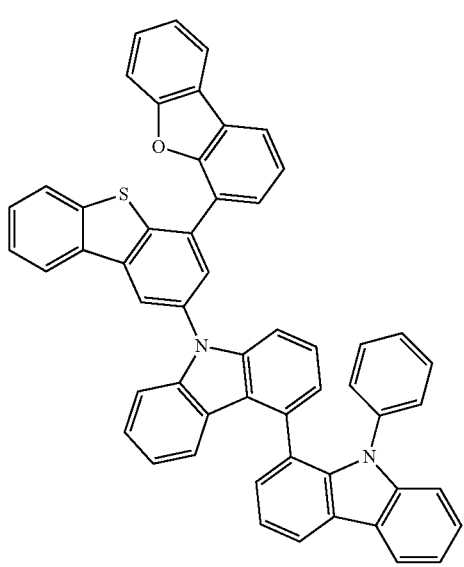
78
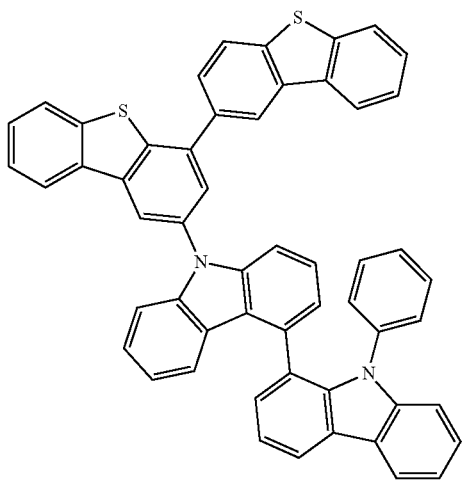
79
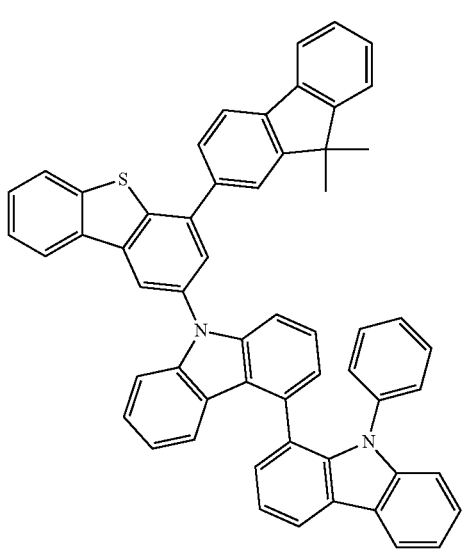
80
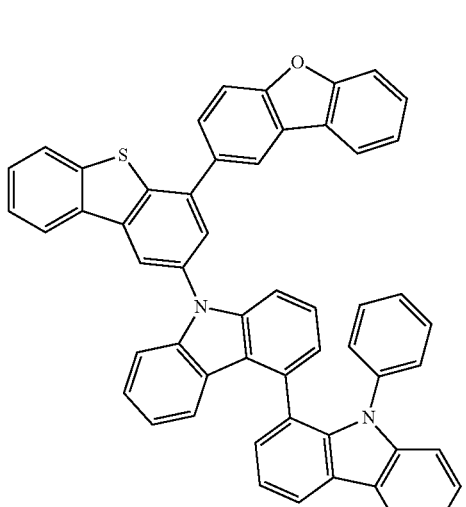

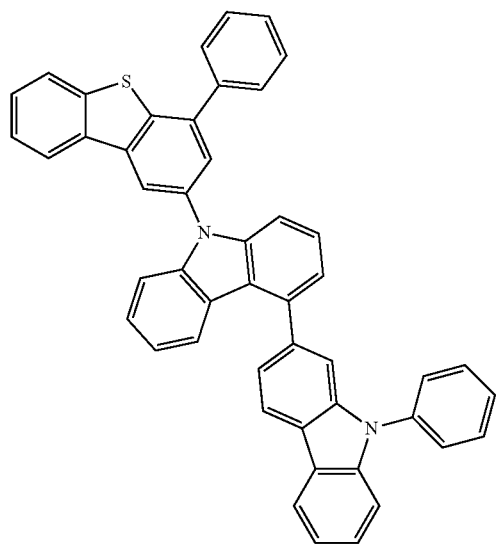
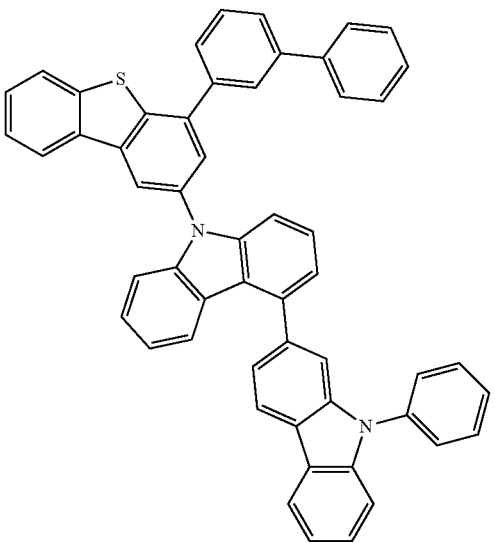

85
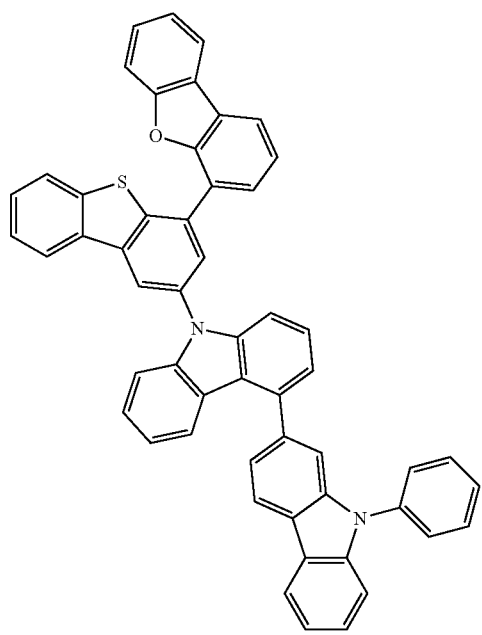
86
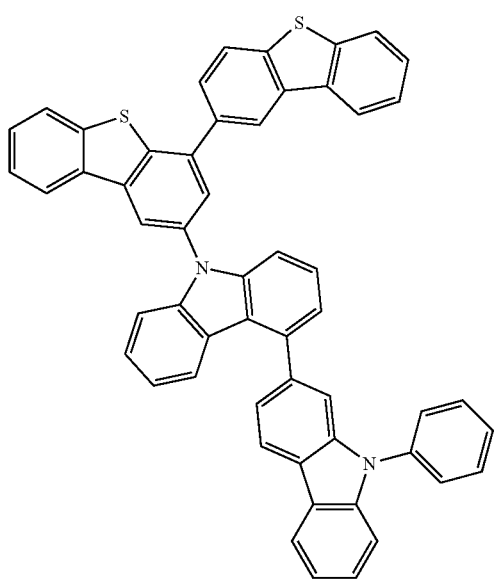
87
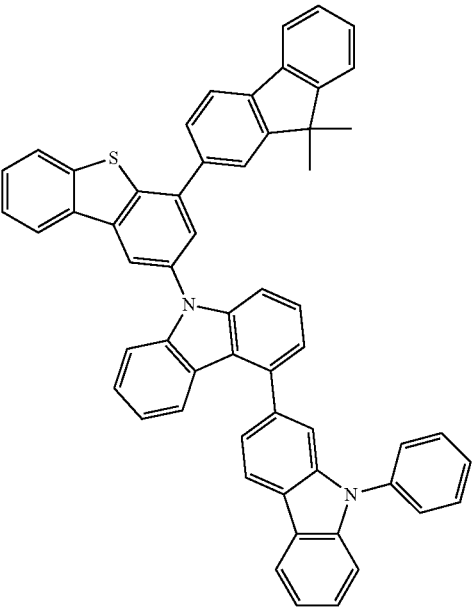
88
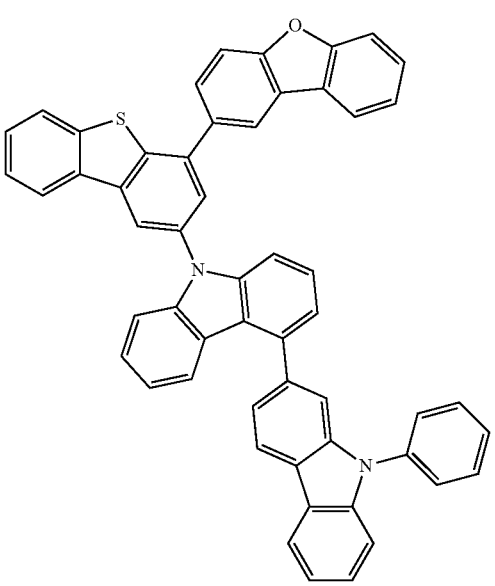

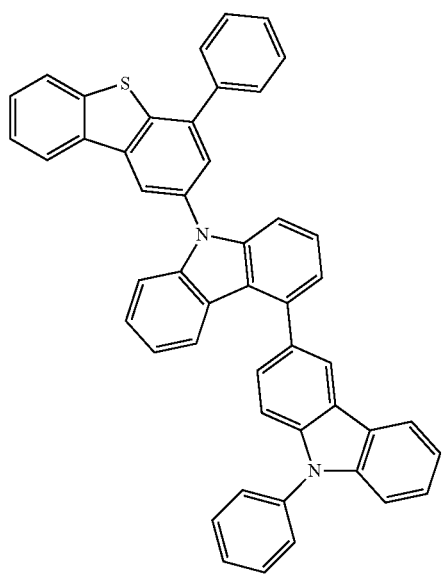
89
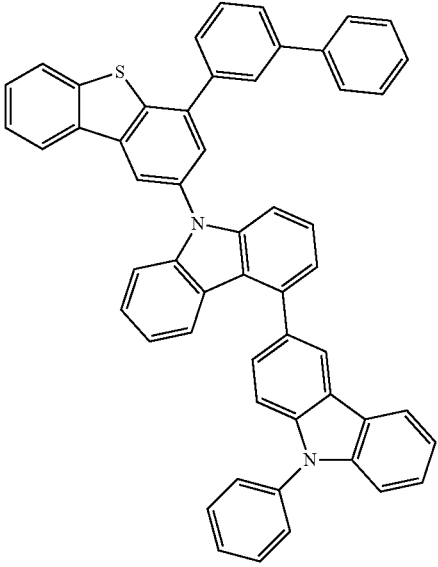
91
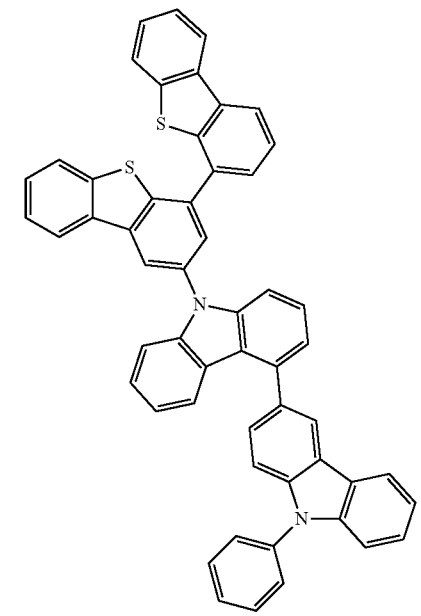
92

93
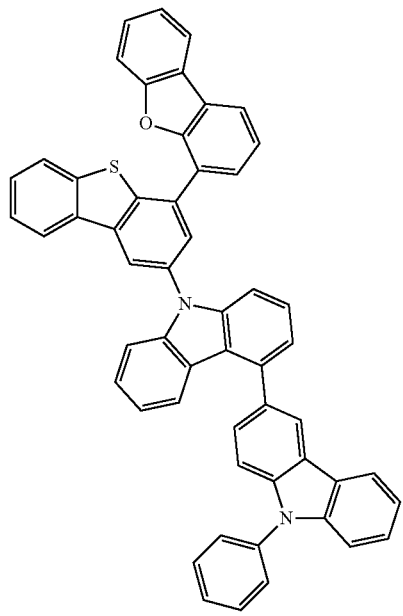
94
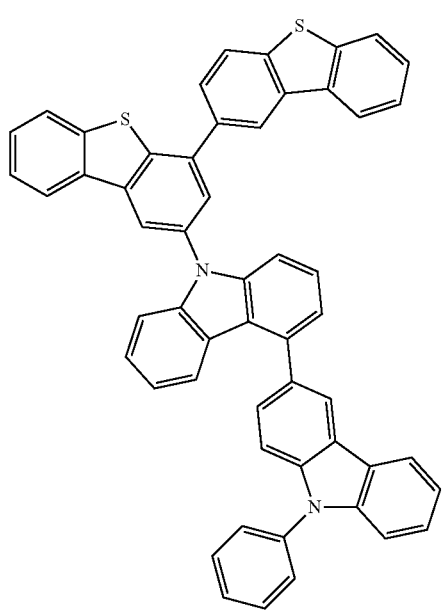
95
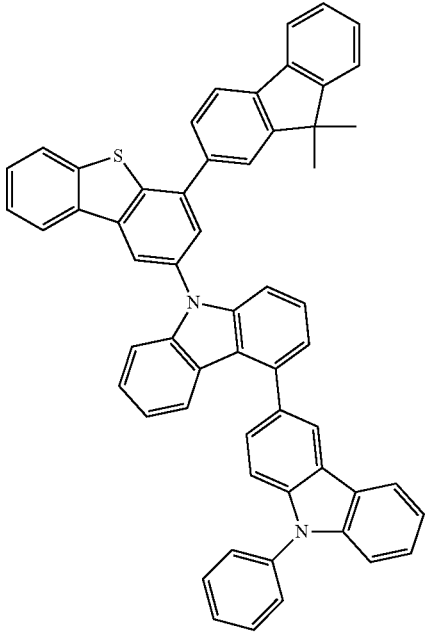
96
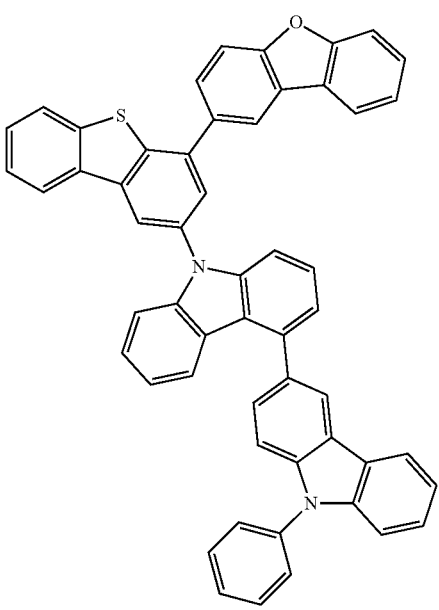

97
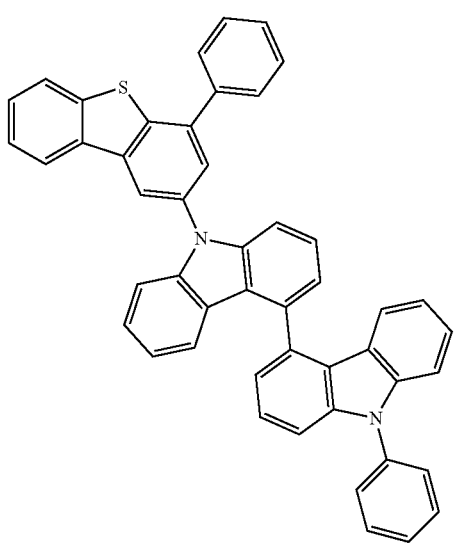
99
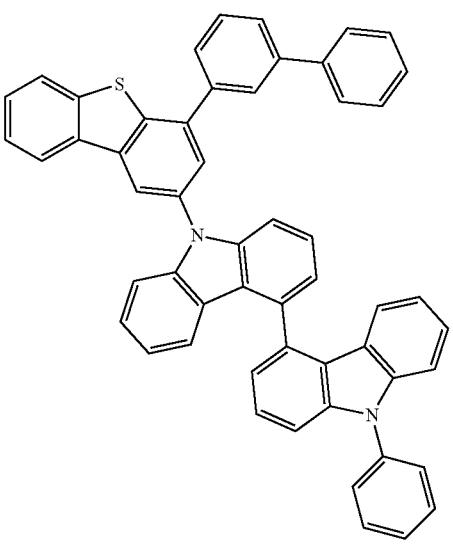
98
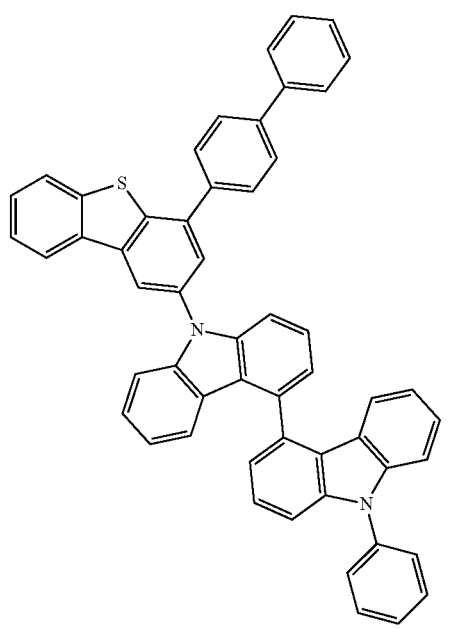
100
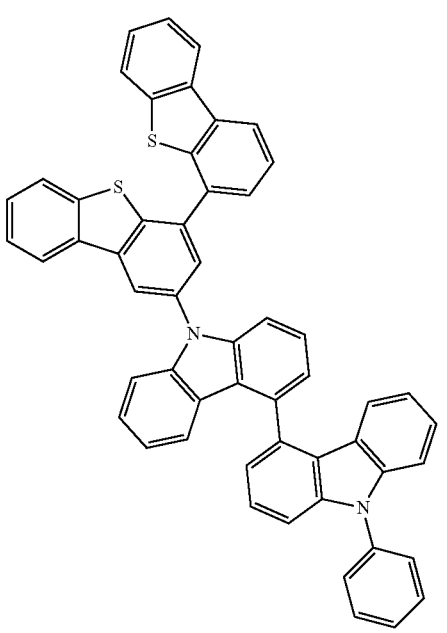

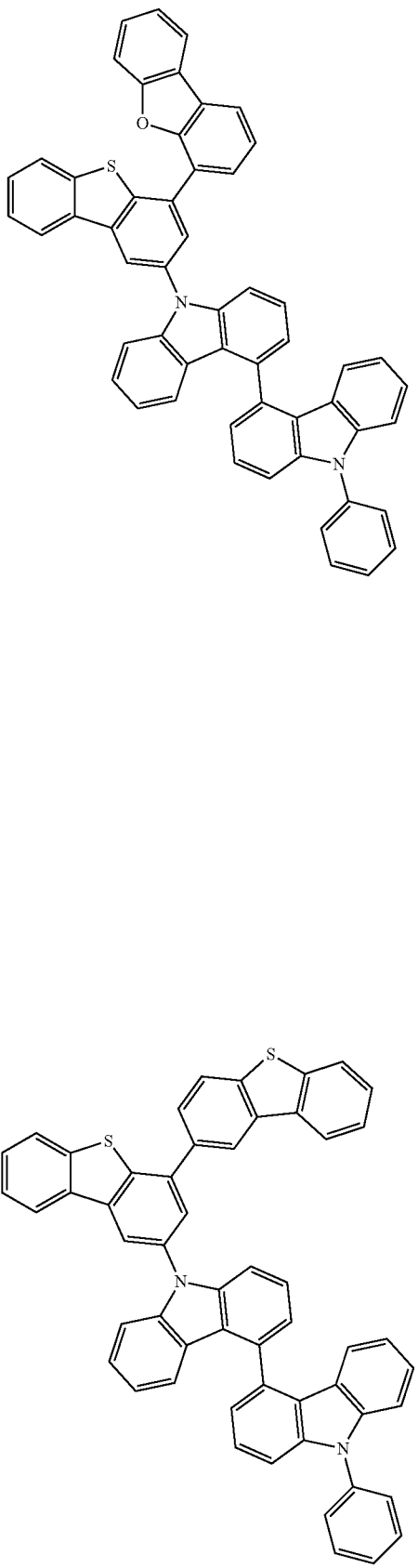

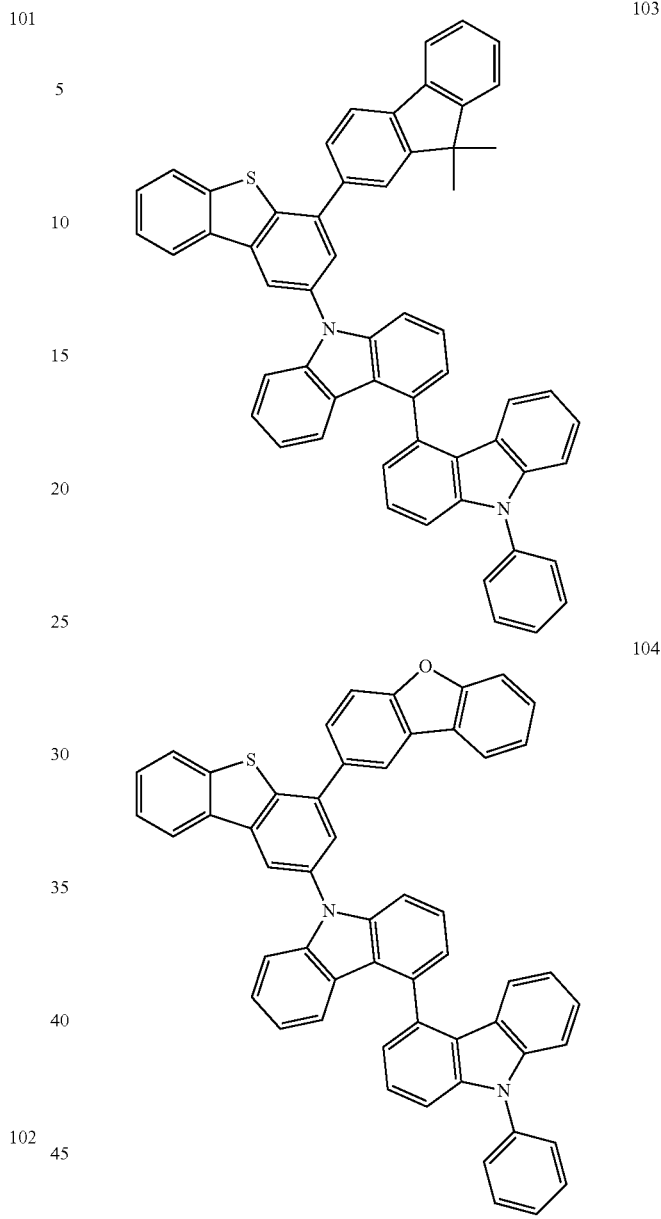

Various substituents may be introduced into the structure of Chemical Formula 1 to synthesize a compound having inherent characteristics of a substituent introduced. For example, a substituent usually used for a hole injection layer material, a material for transporting holes, a light emitting layer material, and an electron transporting layer material, which are used for manufacturing an organic light emitting device, may be introduced into the core structure to synthesize a material which satisfies conditions required for each organic material layer.

It is possible to finely adjust an energy band gap by introducing various substituents into the structure of Chemical Formula 1, and meanwhile, it is possible to improve characteristics at the interface between organic materials and diversify the use of the material.

Meanwhile, the hetero-cyclic compound has a high glass transition temperature (Tg) and thus has excellent thermal stability. The increase in thermal stability becomes an important factor for providing driving stability to a device.

The hetero-cyclic compound according to an exemplary embodiment of the present application may be prepared by a multi-step chemical reaction. Some intermediate compounds are first prepared, and the compound of Chemical Formula 1 may be prepared from the intermediate compounds. More specifically, the hetero-cyclic compound according to an exemplary embodiment of the present application may be prepared based on the Preparation Examples to be described below.

Another exemplary embodiment of the present application provides an organic light emitting device including the hetero-cyclic compound represented by Chemical Formula 1.

The organic light emitting device according to an exemplary embodiment of the present application may be manufactured by typical manufacturing methods and materials of the organic light emitting device, except that the above-described hetero-cyclic compound is used to form an organic material layer having one or more layers.

The hetero-cyclic compound may be formed as an organic material layer by not only a vacuum deposition method, but also a solution application method when an organic light emitting device is manufactured. Here, the solution application method means spin coating, dip coating, inkjet printing, screen printing, a spray method, roll coating, and the like, but is not limited thereto.

Specifically, the organic light emitting device according to an exemplary embodiment of the present application includes a positive electrode, a negative electrode, and an organic material layer having one or more layers disposed between the positive electrode and the negative electrode, in which one or more layers of the organic material layer include the hetero-cyclic compound represented by Chemical Formula 1.

FIGS. 1 to 3 exemplify the stacking sequence of the electrodes and the organic material layer of the organic light emitting device according to an exemplary embodiment of the present application. However, the scope of the present application is not intended to be limited by these drawings, and the structure of the organic light emitting device known in the art may also be applied to the present application.

According to FIG. 1, an organic light emitting device in which a positive electrode (200), an organic material layer (300), and a negative electrode (400) are sequentially stacked on a substrate (100) is illustrated. However, the organic light emitting device is not limited only to such a structure, and as in FIG. 2, an organic light emitting device in which a negative electrode, an organic material layer, and a positive electrode are sequentially stacked on a substrate may also be implemented.

FIG. 3 exemplifies a case where an organic material layer is a multilayer. An organic light emitting device according to FIG. 3 includes a hole injection layer (301), a hole transporting layer (302), a light emitting layer (303), a hole blocking layer (304), an electron transporting layer (305), and an electron injection layer (306). However, the scope of the present application is not limited by the stacking structure as described above, and if necessary, the other layers except for the light emitting layer may be omitted, and another necessary functional layer may be further added.

The organic light emitting device according to the present specification may be manufactured by the materials and methods known in the art, except that one or more layers of the organic material layer include the hetero-cyclic compound represented by Chemical Formula 1.

The hetero-cyclic compound represented by Chemical Formula 1 may alone constitute one or more layers of the organic material layer of the organic light emitting device. However, the hetero-cyclic compound represented by Chemical Formula 1 may be mixed with another material, if necessary, to constitute an organic material layer.

The hetero-cyclic compound represented by Chemical Formula 1 may be used as a material for an electron transporting layer, a hole blocking layer, or a light emitting layer, and the like in an organic light emitting device. As an example, the hetero-cyclic compound represented by Chemical Formula 1 may be used as a material for an electron transporting layer, a hole transporting layer, or a light emitting layer of an organic light emitting device.

The hetero-cyclic compound represented by Chemical Formula 1 may be used as a material for a light emitting layer in an organic light emitting device. As an example, the hetero-cyclic compound represented by Chemical Formula 1 may be used as a material for a phosphorescent host of a light emitting layer in an organic light emitting device.

In the organic light emitting device according to an exemplary embodiment of the present application, materials other than the hetero-cyclic compound of Chemical Formula 1 will be exemplified below, but these materials are illustrative only and are not for limiting the scope of the present application, and may be replaced with materials publicly known in the art.

As a positive electrode material, materials having a relatively high work function may be used, and a transparent conductive oxide, a metal or a conductive polymer, and the like may be used. Specific examples of the positive electrode material include: a metal such as vanadium, chromium, copper, zinc, and gold, or an alloy thereof; a metal oxide such as zinc oxide, indium oxide, indium tin oxide (ITO), and indium zinc oxide (IZO); a combination of a metal and an oxide, such as ZnO:Al or $SnO_2$:Sb; a conductive polymer such as poly(3-methyl compound), poly[3,4-(ethylene-1,2-dioxy)compound] (PEDT), polypyrrole, and polyaniline; and the like, but are not limited thereto.

As a material for the negative electrode, materials having a relatively low work function may be used, and a metal, a metal oxide, or a conductive polymer, and the like may be used. Specific examples of the negative electrode material include: a metal such as magnesium, calcium, sodium, potassium, titanium, indium, yttrium, lithium, gadolinium, aluminum, silver, tin, and lead, or an alloy thereof; a multi-layer structured material such as LiF/Al or $LiO_2$/Al; and the like, but are not limited thereto.

As a hole injection material, a publicly-known hole injection material may also be used, and it is possible to use, for example, a phthalocyanine compound such as copper phthalocyanine disclosed in U.S. Pat. No. 4,356,429 or starburst-type amine derivatives described in the document [Advanced Material, 6, p. 677 (1994)], for example, tris(4-carbazoyl-9-ylphenyl)amine (TCTA), 4,4',4"-tris[phenyl(m-tolyl)amino]triphenylamine (m-MTDATA), 1,3,5-tris[4-(3-methylphenylphenylamino)phenyl]benzene (m-MTDAPB), polyaniline/dodecylbenzenesulfonic acid or poly(3,4-ethylenedioxythiophene)/poly(4-styrenesulfonate), which is a soluble conductive polymer, polyaniline/camphor sulfonic acid or polyaniline/poly(4-styrene-sulfonate), and the like.

As a hole transporting material, a pyrazoline derivative, an arylamine-based derivative, a stilbene derivative, a triphenyldiamine derivative, and the like may be used, and a low-molecular weight or polymer material may also be used.

As an electron transporting material, it is possible to use an oxadiazole derivative, anthraquinodimethane and a derivative thereof, benzoquinone and a derivative thereof, naphthoquinone and a derivative thereof, anthraquinone and a derivative thereof, tetracyanoanthraquinodimethane and a derivative thereof, a fluorenone derivative, diphenyldicyanoethylene and a derivative thereof, a diphenoquinone derivative, a metal complex of 8-hydroxyquinoline and a derivative thereof, and the like, and a low-molecular weight material and a polymer material may also be used.

As an electron injection material, for example, LiF is representatively used in the art, but the present application is not limited thereto.

As a light emitting material, a red, green, or blue light emitting material may be used, and if necessary, two or more light emitting materials may be mixed and used. In this case, two or more light emitting materials are deposited or used as an individual supply source, or pre-mixed to be deposited and used as one supply source. Further, as the light emitting material, a fluorescent material may also be used, but a phosphorescent material may also be used. As the light emitting material, it is also possible to use alone a material which emits light by combining holes and electrons each injected from a positive electrode and a negative electrode, but materials in which a host material and a dopant material are involved in light emission together may also be used.

When hosts of the light emitting material are mixed and used, the same series of hosts may also be mixed and used, and different series of hosts may also be mixed and used. For example, two or more materials selected from n-type host materials or p-type host materials may be used as a host material for a light emitting layer.

The organic light emitting device according to an exemplary embodiment of the present application may be a top emission type, a bottom emission type, or a dual emission type according to the material to be used.

The hetero-cyclic compound according to an exemplary embodiment of the present application may act even in organic electronic devices including organic solar cells, organic photoconductors, organic transistors, and the like, based on the principle similar to those applied to organic light emitting devices.

Hereinafter, the present specification will be described in more detail through Examples, but these Examples are provided only for exemplifying the present application, and are not intended to limit the scope of the present application.

EXAMPLES

<Preparation Example 1> Synthesis of Compound 2

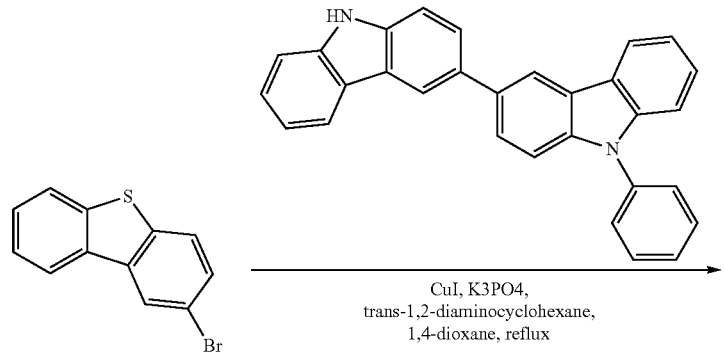

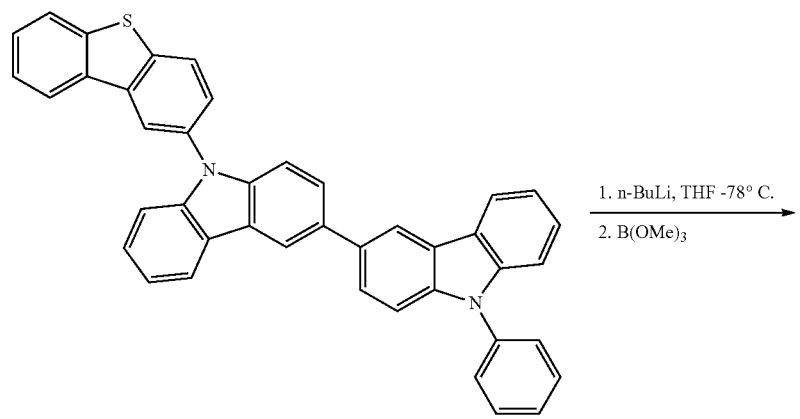

2-2(ref 2)

-continued

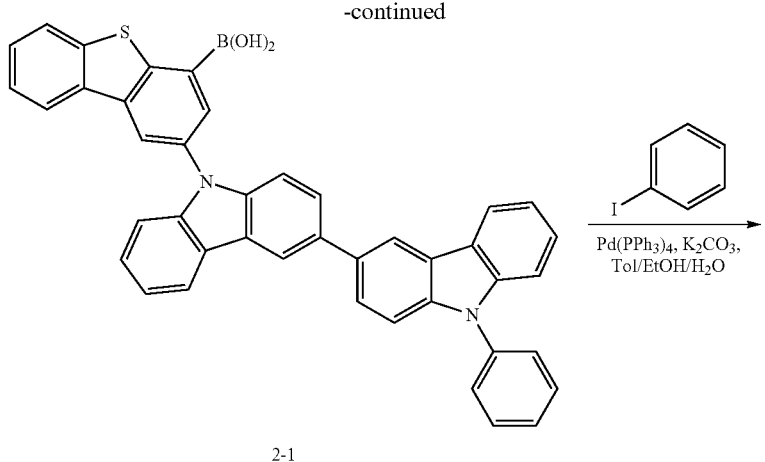

2-1

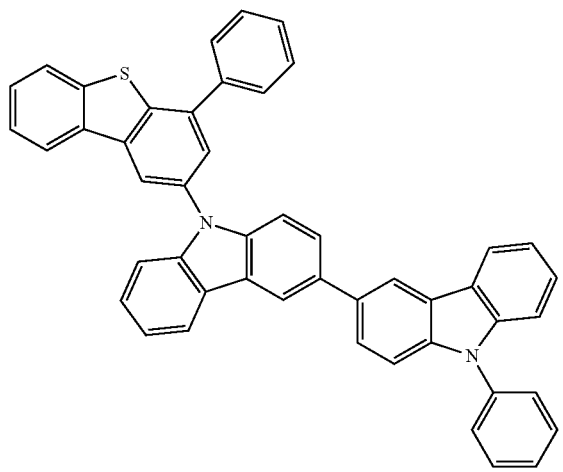

2

1) Preparation of Compound 2-2 (ref 2)

4.2 g (15.8 mM) of 2-bromodibenzo[b,d]thiophene, 6.5 g (15.8 mM) of 9-phenyl-9H,9'H-3,3'-bicarbazole, 3.0 g (15.8 mM) of CuI, 1.9 mL (15.8 mM) of trans-1,2-diaminocyclohexane, and 3.3 g (31.6 mM) of $K_3PO_4$ were dissolved in 100 mL of 1,4-oxane, and then the resulting solution was refluxed for 24 hours. After the reaction was completed, distilled water and DCM were added thereto at room temperature, extraction was performed, the organic layer was dried over $MgSO_4$, and then the solvent was removed by a rotary evaporator. The reactant was purified by column chromatography (DCM:Hex=1:3) and recrystallized with methanol to obtain 7.9 g (85%) of Target Compound 2-2.

2) Preparation of Compound 2-1

7.4 mL (18.6 mmol) of 2.5 M n-BuLi was added dropwise to a mixed solution containing 8.4 g (14.3 mmol) of Compound 2-2 and 100 mL of THF at −78° C., and the resulting mixture was stirred at room temperature for 1 hour. 4.8 mL (42.9 mmol) of trimethyl borate was added dropwise to the reaction mixture, and the resulting mixture was stirred at room temperature for 2 hours. After the reaction was completed, distilled water and DCM were added thereto at room temperature, extraction was performed, the organic layer was dried over $MgSO_4$, and then the solvent was removed by a rotary evaporator. The reactant was purified by column chromatography (DCM:MeOH=100:3) and recrystallized with DCM to obtain 3.9 g (70%) of Target Compound 2-1.

3) Preparation of Compound 2

6.7 g (10.5 mM) of Compound 2-1, 2.1 g (10.5 mM) of iodobenzene, 606 mg (0.52 mM) of $Pd(PPh_3)_4$, and 2.9 g (21.0 mM) of $K_2CO_3$ were dissolved in 100/20/20 mL of toluene/EtOH/$H_2O$, and then the resulting solution was refluxed for 12 hours. After the reaction was completed, distilled water and DCM were added thereto at room temperature, extraction was performed, the organic layer was dried over $MgSO_4$, and then the solvent was removed by a rotary evaporator. The reactant was purified by column chromatography (DCM:Hex=1:3) and recrystallized with methanol to obtain 4.9 g (70%) of Target Compound 2. Target Compound A was synthesized by performing the preparation in the same manner as in the preparation of Compound 2, except that Intermediate A in the following Table 1 was used instead of iodobenzene in the preparation of Compound 2.

TABLE 1
| Compound No. | Intermediate A | Target Compound A | Yield |
|---|---|---|---|
| 1 | 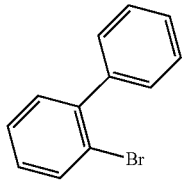 [SMILES: Brc1ccccc1-c1ccccc1] | 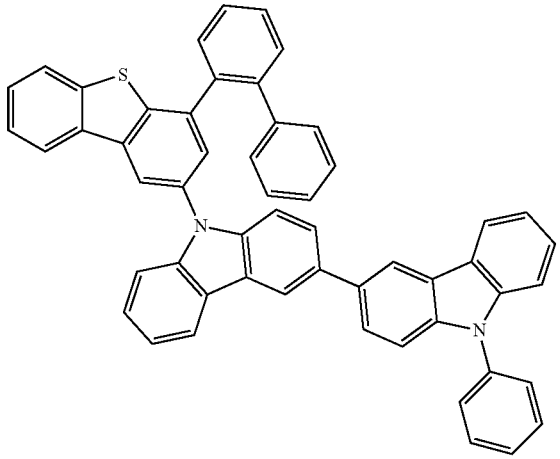 [SMILES: c1ccc(-c2ccccc2-c2cc(-n3c4ccccc4c4cc(-c5ccc6c(c5)c5ccccc5n6-c5ccccc5)ccc43)cc3c2sc2ccccc23)cc1] | 79% |
| 3 | 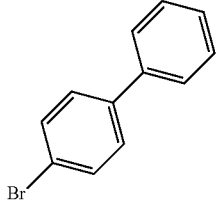 [SMILES: Brc1ccc(-c2ccccc2)cc1] | 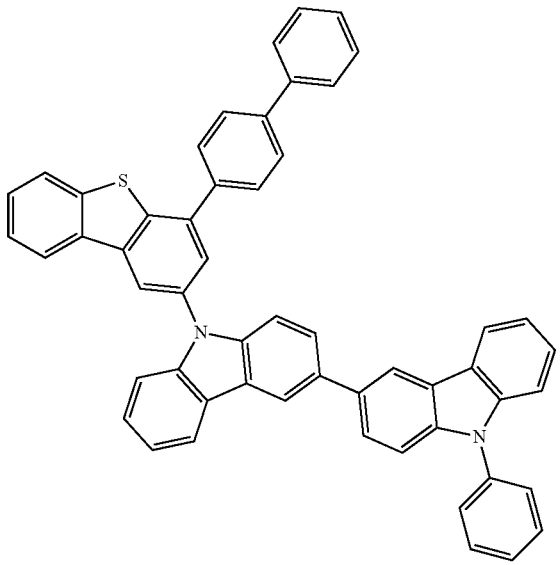 [SMILES: c1ccc(-c2ccc(-c3cc(-n4c5ccccc5c5cc(-c6ccc7c(c6)c6ccccc6n7-c6ccccc6)ccc54)cc4c3sc3ccccc34)cc2)cc1] | 83% |
| 4 | 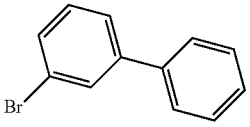 [SMILES: Brc1cccc(-c2ccccc2)c1] | 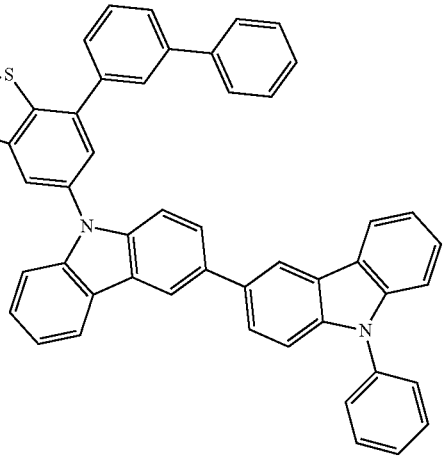 | 81% |

TABLE 1-continued
| Compound No. | Intermediate A | Target Compound A | Yield |
| --- | --- | --- | --- |
| 5 | 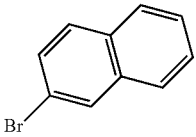 [SMILES: Brc1ccc2ccccc2c1] | 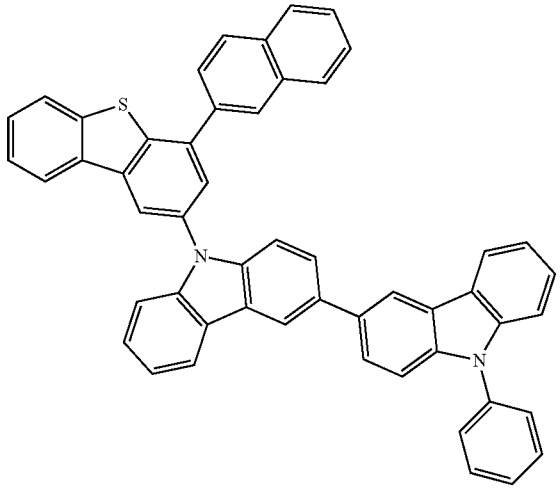 [SMILES: c1ccc(-n2c3ccccc3c3cc(-c4ccc5c(c4)c4ccccc4n5-c4cc(-c5ccc6ccccc6c5)c5sc6ccccc6c5c4)ccc32)cc1] | 72% |
| 6 | 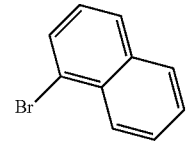 [SMILES: Brc1cccc2ccccc12] | 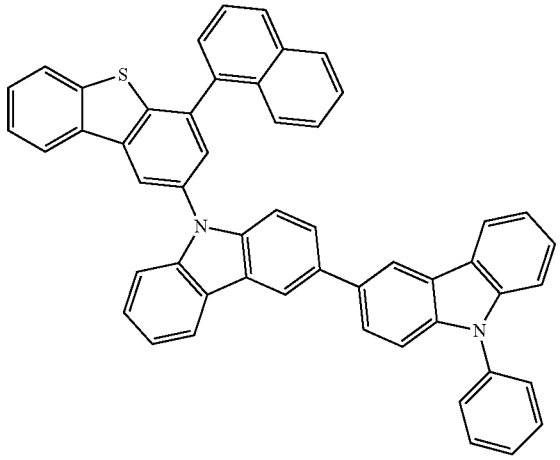 [SMILES: c1ccc(-n2c3ccccc3c3cc(-c4ccc5c(c4)c4ccccc4n5-c4cc(-c5cccc6ccccc56)c5sc6ccccc6c5c4)ccc32)cc1] | 75% |
| 7 | 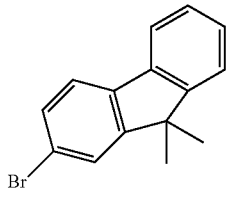 [SMILES: CC1(C)c2ccccc2-c2ccc(Br)cc21] | 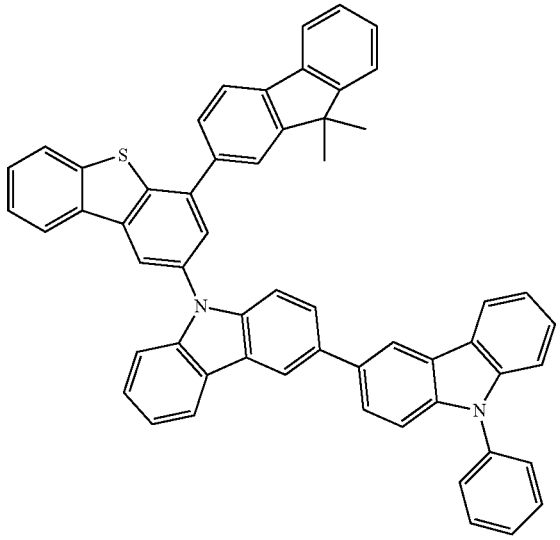 [SMILES: CC1(C)c2ccccc2-c2ccc(-c3cc(-n4c5ccccc5c5cc(-c6ccc7c(c6)c6ccccc6n7-c6ccccc6)ccc54)cc4c3sc3ccccc34)cc21] | 86% |

TABLE 1-continued
| Compound No. | Intermediate A | Target Compound A | Yield |
|---|---|---|---|
| 8 | 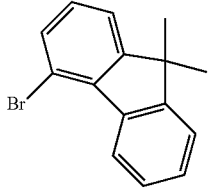 [SMILES: CC1(C)c2ccccc2-c2c(Br)cccc21] | 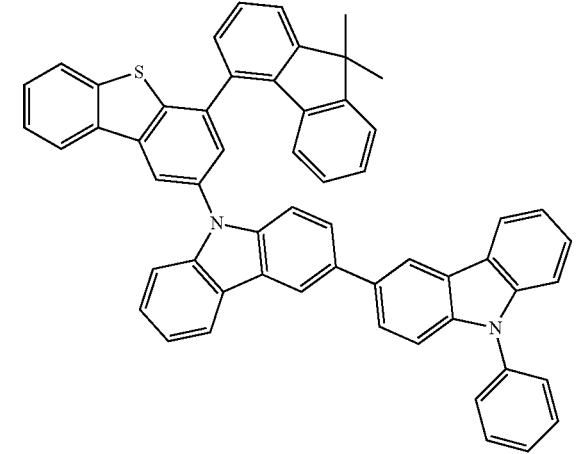 [SMILES: CC1(C)c2ccccc2-c2c(-c3cc(-n4c5ccccc5c5cc(-c6ccc7c(c6)c6ccccc6n7-c6ccccc6)ccc54)cc4c3sc3ccccc34)cccc21] | 87% |
| 9 | 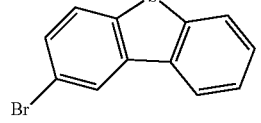 | 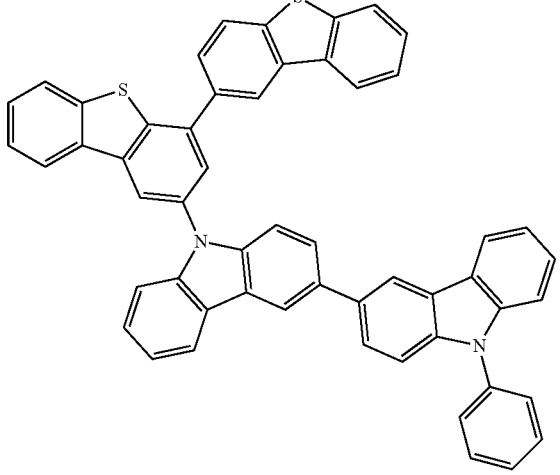 | 78% |
| 10 | 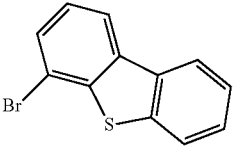 [SMILES: Brc1cccc2c1sc1ccccc12] | 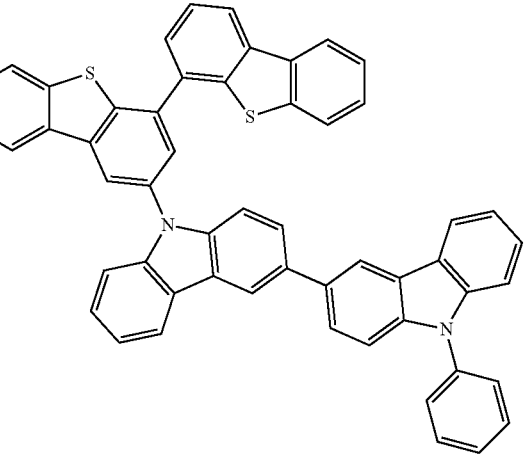 | 82% |

TABLE 1-continued

| Compound No. | Intermediate A | Target Compound A | Yield |
|---|---|---|---|
| 11 | 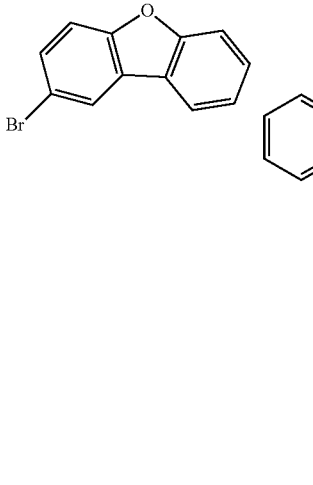 | 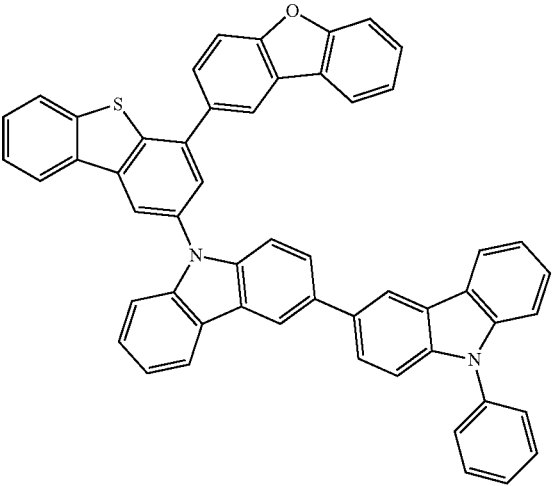 [SMILES: c1ccc(-n2c3ccccc3c3cc(-c4ccc5c(c4)c4ccccc4n5-c4cc(-c5ccc6oc7ccccc7c6c5)c5sc6ccccc6c5c4)ccc32)cc1] | 89% |
| 12 | 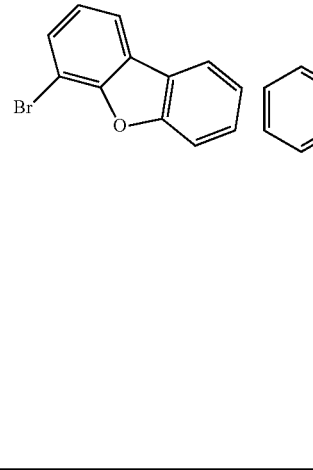 | 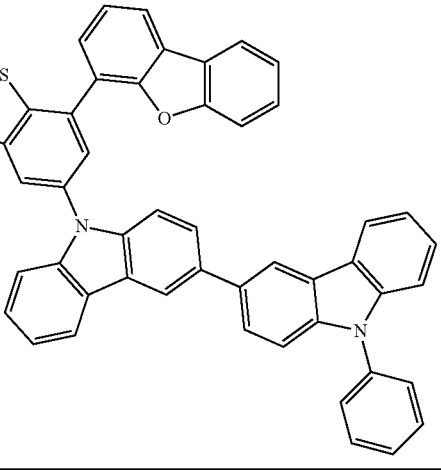 | 73% |

Target Compound B was synthesized by performing the preparation in the same manner as in the preparation of Compound 2, except that Intermediate B and Intermediate C in the following Table 2 were used in the preparation of Compound 2.

TABLE 2

| Compound No. | Intermediate B | Intermediate C | Target Compound B | Yield |
|---|---|---|---|---|
| 13 | 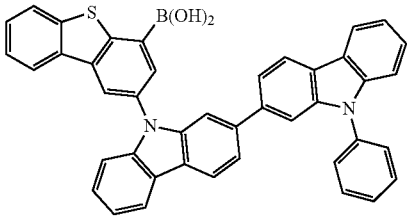 [SMILES: OB(O)c1cc(-n2c3ccccc3c3ccc(-c4ccc5c6ccccc6n(-c6ccccc6)c5c4)cc32)cc2c1sc1ccccc12] | 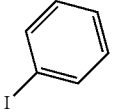 | 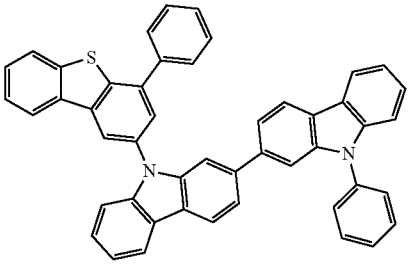 [SMILES: c1ccc(-c2cc(-n3c4ccccc4c4ccc(-c5ccc6c7ccccc7n(-c7ccccc7)c6c5)cc43)cc3c2sc2ccccc23)cc1] | 78% |

TABLE 2-continued

| Compound No. | Intermediate B | Intermediate C | Target Compound B | Yield |
|---|---|---|---|---|
| 14 | | | | 81% |
| 24 | | | | 83% |
| 26 | | | | 85% |
| 33 | | | | 79% |

TABLE 2-continued

| Compound No. | Intermediate B | Intermediate C | Target Compound B | Yield |
|---|---|---|---|---|
| 34 | | | | 83% |
| 41 | | | | 72% |
| 42 | | | | 79% |
| 49 | | | | 75% |

TABLE 2-continued

| Compound No. | Intermediate B | Intermediate C | Target Compound B | Yield |
|---|---|---|---|---|
| 50 | | | | 78% |
| 57 | | | | 81% |
| 58 | | | | 82% |
| 65 | | | | 87% |

TABLE 2-continued
| Compound No. | Intermediate B | Intermediate C | Target Compound B | Yield |
|---|---|---|---|---|
| 66 | 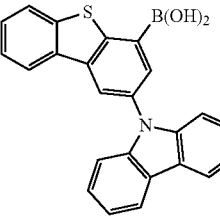 | 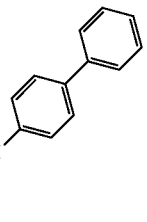 | 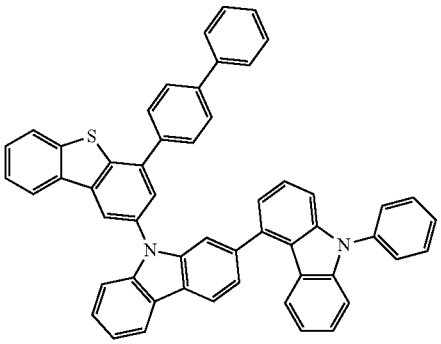 [SMILES: c1ccc(-c2ccc(-c3cc(-n4c5ccccc5c5ccc(-c6cccc7c6c6ccccc6n7-c6ccccc6)cc54)cc4c3sc3ccccc34)cc2)cc1] | 81% |
| 73 | 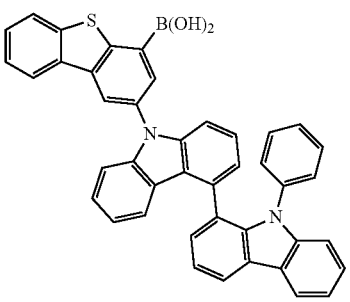 [SMILES: OB(O)c1cc(-n2c3ccccc3c3c(-c4cccc5c6ccccc6n(-c6ccccc6)c45)cccc32)cc2c1sc1ccccc12] | 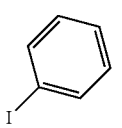 | 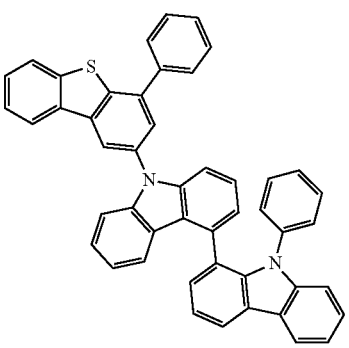 [SMILES: c1ccc(-c2cc(-n3c4ccccc4c4c(-c5cccc6c7ccccc7n(-c7ccccc7)c56)cccc43)cc3c2sc2ccccc23)cc1] | 78% |
| 74 | 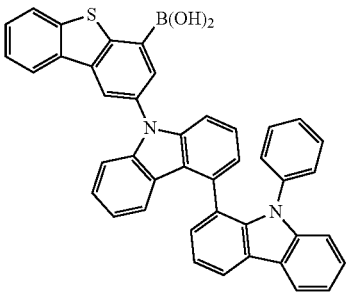 [SMILES: OB(O)c1cc(-n2c3ccccc3c3c(-c4cccc5c6ccccc6n(-c6ccccc6)c45)cccc32)cc2c1sc1ccccc12] | 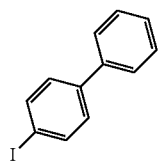 [SMILES: Ic1ccc(-c2ccccc2)cc1] | 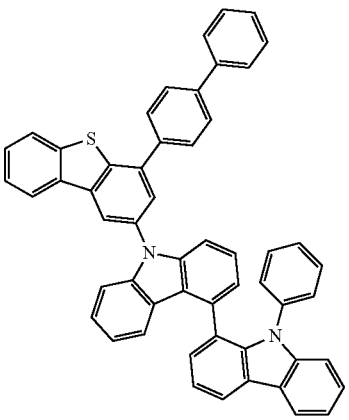 [SMILES: c1ccc(-c2ccc(-c3cc(-n4c5ccccc5c5c(-c6cccc7c8ccccc8n(-c8ccccc8)c67)cccc54)cc4c3sc3ccccc34)cc2)cc1] | 79% |
| 81 | 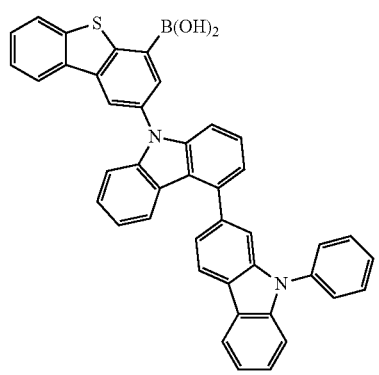 [SMILES: OB(O)c1cc(-n2c3ccccc3c3c(-c4ccc5c6ccccc6n(-c6ccccc6)c5c4)cccc32)cc2c1sc1ccccc12] | 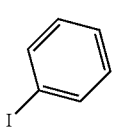 | 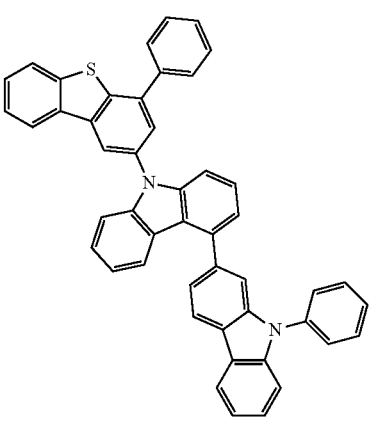 [SMILES: c1ccc(-c2cc(-n3c4ccccc4c4c(-c5ccc6c7ccccc7n(-c7ccccc7)c6c5)cccc43)cc3c2sc2ccccc23)cc1] | 82% |

TABLE 2-continued

| Compound No. | Intermediate B | Intermediate C | Target Compound B | Yield |
|---|---|---|---|---|
| 82 | | | | 86% |
| 89 | | | | 89% |
| 90 | | | | 85% |

TABLE 2-continued

| Compound No. | Intermediate B | Intermediate C | Target Compound B | Yield |
|---|---|---|---|---|
| 97 | 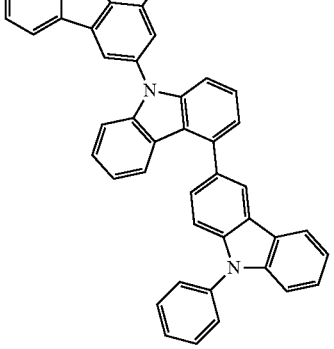 | 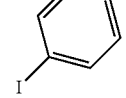 | 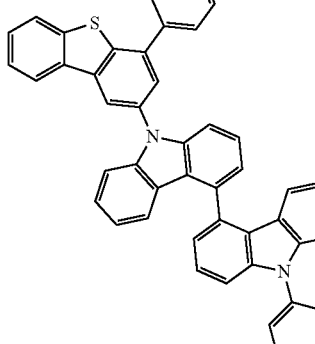 | 73% |
| 98 | 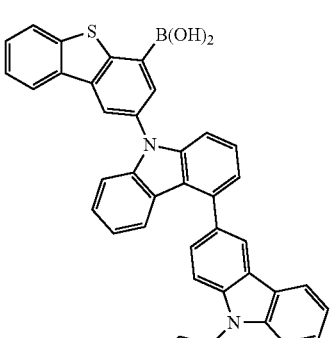 | 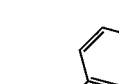 | 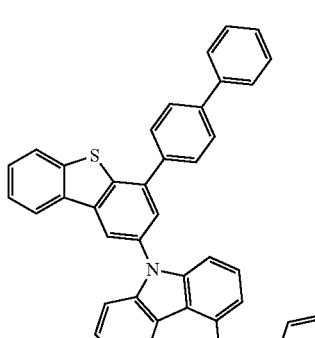 | 77% |

<Preparation Example 2> Synthesis of Compound Ref 2

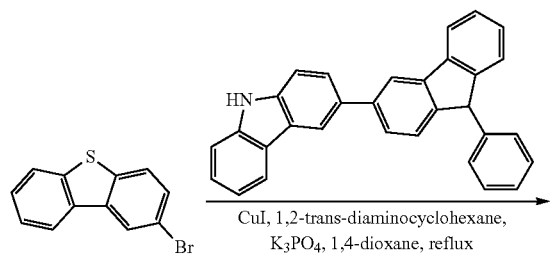

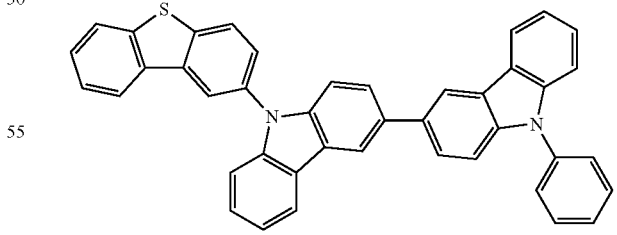

ref 2

4.2 g (15.8 mM) of 2-bromodibenzo[b,d]thiophene, 6.5 g (15.8 mM) of 9-phenyl-9H,9'H-3,3'-bicarbazole, 3.0 g (15.8 mM) of CuI, 1.9 mL (15.8 mM) of trans-1,2-diaminocyclohexane, and 3.3 g (31.6 mM) of K₃PO₄ were dissolved in 100 mL of 1,4-oxane, and then the resulting solution was refluxed for 24 hours. After the reaction was completed, distilled water and DCM were added thereto at room temperature, extraction was performed, the organic layer was dried over MgSO₄, and then the solvent was removed by a rotary evaporator. The reactant was purified by column chromatography (DCM:Hex=1:3) and recrystallized with methanol to obtain 7.9 g (85%) of Target Compound ref 2.

<Preparation Example 3> Synthesis of Compound Ref 3

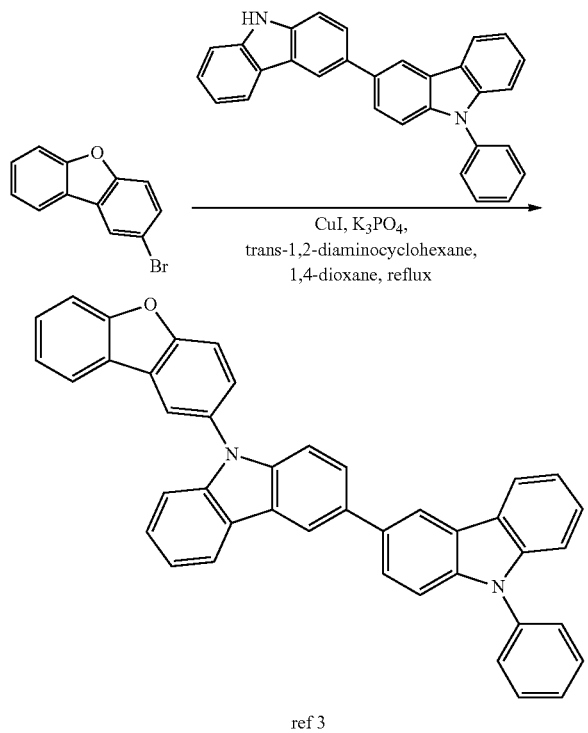

ref 3

3.9 g (15.8 mM) of 2-bromodibenzo[b,d]furan, 6.5 g (15.8 mM) of 9-phenyl-9H,9'H-3,3'-bicarbazole, 3.0 g (15.8 mM) of CuI, 1.9 mL (15.8 mM) of trans-1,2-diaminocyclohexane, and 3.3 g (31.6 mM) of K₃PO₄ were dissolved in 100 mL of 1,4-oxane, and then the resulting solution was refluxed for 24 hours. After the reaction was completed, distilled water and DCM were added thereto at room temperature, extraction was performed, the organic layer was dried over MgSO₄, and then the solvent was removed by a rotary evaporator. The reactant was purified by column chromatography (DCM:Hex=1:3) and recrystallized with methanol to obtain 7.7 g (85%) of Target Compound ref 3.

<Preparation Example 4> Synthesis of Compound Ref 4

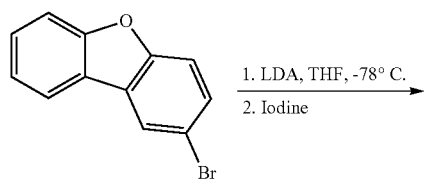

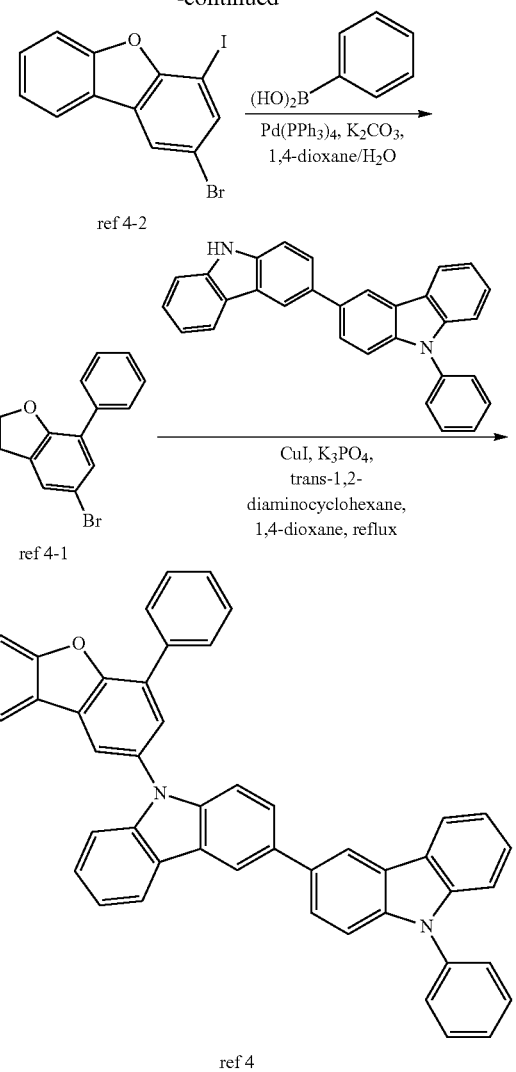

ref 4

1) Preparation of Compound Ref 4-2

88.0 mL (157.8 mM) of 1.8 M LDA was added dropwise to a mixed solution containing 30.0 g (121.4 mM) of 2-bromodibenzofuran and 300 mL of THF at −78° C., and the resulting mixture was stirred at room temperature for 1 hour. 11.0 g (42.9 mmol) of iodine was put into the reaction mixture, and the resulting mixture was stirred at room temperature for 2 hours. After the reaction was completed, distilled water and DCM were added thereto at room temperature, extraction was performed, the organic layer was dried over MgSO₄, and then the solvent was removed by a rotary evaporator. The reactant was purified by column chromatography (DCM) and recrystallized with MeOH to obtain 23.1 g (51%) of Target Compound ref 4-2.

2) Preparation of Compound Ref 4-1

3.9 g (10.5 mM) of Compound ref 4-2, 1.3 g (10.5 mM) of phenylboronic acid, 606 mg (0.52 mM) of Pd(PPh₃)₄, and 2.9 g (21.0 mM) of K₂CO₃ were dissolved in 100/20/20 mL of toluene/EtOH/H₂O, and then the resulting solution was refluxed for 12 hours. After the reaction was completed, distilled water and DCM were added thereto at room temperature, extraction was performed, the organic layer was dried over MgSO₄, and then the solvent was removed by a rotary evaporator. The reactant was purified by column chromatography (DCM:Hex=1:3) and recrystallized with methanol to obtain 2.4 g (70%) of Target Compound ref 4-1.

3) Preparation of Compound Ref 4

5.1 g (15.8 mM) of Compound ref 4-1, 6.5 g (15.8 mM) of 9-phenyl-9H,9'H-3,3'-bicarbazole, 3.0 g (15.8 mM) of CuI, 1.9 mL (15.8 mM) of trans-1,2-diaminocyclohexane, and 3.3 g (31.6 mM) of $K_3PO_4$ were dissolved in 100 mL of 1,4-oxane, and then the resulting solution was refluxed for 24 hours. After the reaction was completed, distilled water and DCM were added thereto at room temperature, extraction was performed, the organic layer was dried over $MgSO_4$, and then the solvent was removed by a rotary evaporator. The reactant was purified by column chromatography (DCM:Hex=1:3) and recrystallized with methanol to obtain 8.7 g (85%) of Target Compound ref 4.

<Preparation Example 5> Synthesis of Compound Ref 5

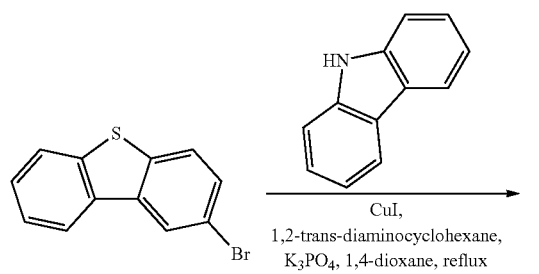

ref 5-2

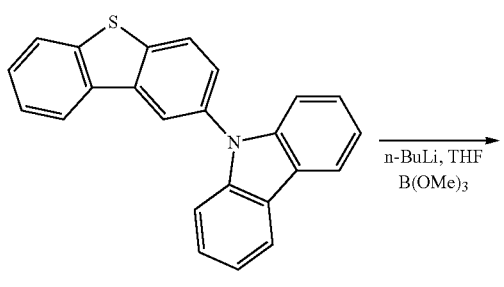

ref 5-1

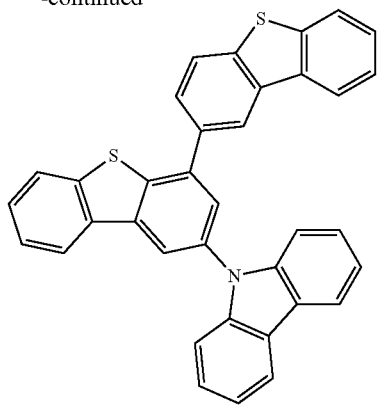

ref 5

1) Preparation of Compound Ref 5-2

5.0 g (19.0 mM) of 2-bromodibenzo[b,d]thiophene, 2.6 g (15.8 mM) of 9H-carbazole, 3.0 g (15.8 mM) of CuI, 1.9 mL (15.8 mM) of trans-1,2-diaminocyclohexane, and 3.3 g (31.6 mM) of $K_3PO_4$ were dissolved in 100 mL of 1,4-oxane, and then the resulting solution was refluxed for 24 hours. After the reaction was completed, distilled water and DCM were added thereto at room temperature, extraction was performed, the organic layer was dried over $MgSO_4$, and then the solvent was removed by a rotary evaporator. The reactant was purified by column chromatography (DCM:Hex=1:3) and recrystallized with methanol to obtain 4.7 g (85%) of Compound ref 5-2.

2) Preparation of Compound Ref 5-1

7.4 mL (18.6 mM) of 2.5 M n-BuLi was added dropwise to a mixed solution containing 5 g (14.3 mM) of Compound ref 5-2 and 100 mL of THF at −78° C., and the resulting mixture was stirred at room temperature for 1 hour. 4.8 mL (42.9 mM) of trimethyl borate (B(OMe)$_3$) was added dropwise to the reaction mixture, and the resulting mixture was stirred at room temperature for 2 hours. After the reaction was completed, distilled water and DCM were added thereto at room temperature, extraction was performed, the organic layer was dried over $MgSO_4$, and then the solvent was removed by a rotary evaporator. The reactant was purified by column chromatography (DCM:MeOH=100:3) and recrystallized with DCM to obtain 3.9 g (70%) of Target Compound ref 5-1.

3) Preparation of Compound Ref 5

7.5 g (19.0 mM) of Compound ref 5-1, 5.0 g (19.0 mM) of 2-bromodibenzo[b,d]thiophene, 1.1 g (0.95 mM) of Pd(PPh$_3$)$_4$, and 5.2 g (38.0 mM) of $K_2CO_3$ were dissolved in 100/20/20 mL of toluene/EtOH/H$_2$O, and then the resulting solution was refluxed for 12 hours. After the reaction was completed, distilled water and DCM were added thereto at room temperature, extraction was performed, the organic layer was dried over $MgSO_4$, and then the solvent was removed by a rotary evaporator. The reactant was purified by column chromatography (DCM:Hex=1:3) and recrystallized with methanol to obtain 7.1 g (70%) of Target Compound ref 5.

<Preparation Example 6> Synthesis of Compound Ref 6

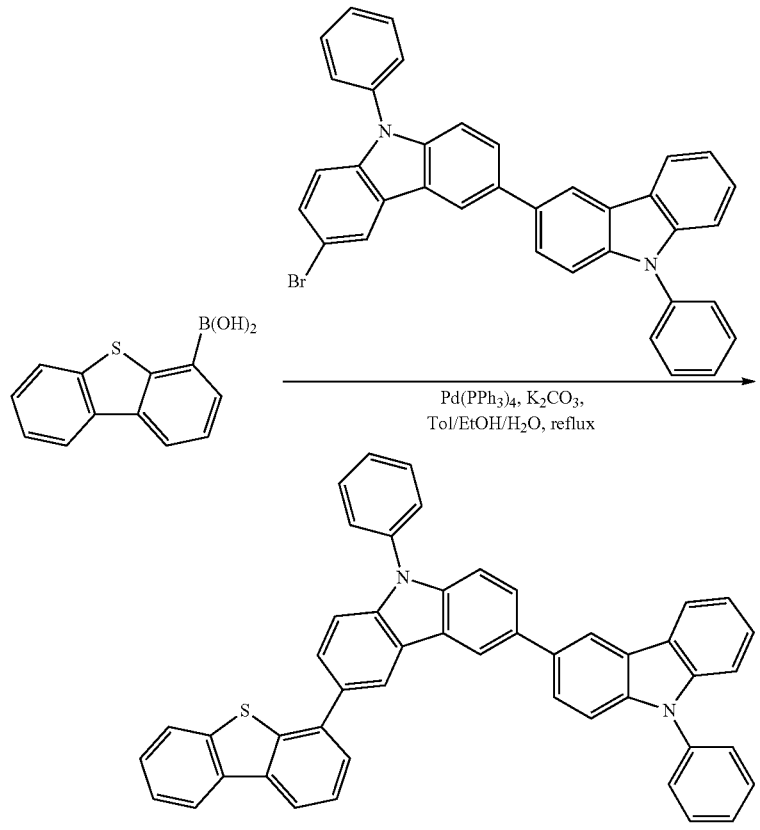

ref 6

4.3 g (19.0 mM) of dibenzo[b,d]thiophen-4-ylboronic acid, 10.7 g (19.0 mM) of 6-bromo-9,9'-diphenyl-9H,9'H-3,3'-bicarbazole, 1.1 g (0.95 mM) of Pd(PPh$_3$)$_4$, and 5.2 g (38.0 mM) of K$_2$CO$_3$ were dissolved in 100/20/20 mL of toluene/EtOH/H$_2$O, and then the resulting solution was refluxed for 12 hours. After the reaction was completed, distilled water and DCM were added thereto at room temperature, extraction was performed, the organic layer was dried over MgSO$_4$, and then the solvent was removed by a rotary evaporator. The reactant was purified by column chromatography (DCM:Hex=1:3) and recrystallized with methanol to obtain 8.9 g (70%) of Target Compound ref 6. Compounds were prepared in the same manner as in the Preparation Examples, and the synthesis confirmation results thereof are shown in the following Tables 3 to 4.

TABLE 3

| Compound No. | $^1$H NMR(CDCl$_3$, 200 Mz) |
|---|---|
| 1 | δ = 8.55 (1H, d), 8.45 (1H, d), 8.30 (1H, d), 8.19 (1H, d), 8.13 (1H, d), 8.00~7.89 (8H, m), 7.79~7.77 (4H, m), 7.62~7.35 (15H, m), 7.20~7.16 (2H, m) |
| 2 | δ = 8.55 (1H, d), 8.45 (1H, d), 8.30 (1H, d), 8.19 (1H, d), 8.13 (1H, d), 8.00~7.89 (6H, m), 7.77 (2H, m), 7.62~7.35 (15H, m), 7.20~7.16 (2H, m) |
| 3 | δ = 8.55 (1H, d), 8.45 (1H, d), 8.30 (1H, d), 8.19 (1H, d), 8.13 (1H, d), 8.00~7.89 (6H, m), 7.77~7.75 (4H, m), 7.62~7.41 (13H, m), 7.25~7.16 (6H, m) |

TABLE 3-continued

| Compound No. | $^1$H NMR(CDCl$_3$, 200 Mz) |
|---|---|
| 4 | δ = 8.55 (1H, d), 8.45 (1H, d), 8.30 (1H, d), 8.19 (1H, d), 8.13 (1H, d), 8.00~7.89 (7H, m), 7.77~7.73 (5H, m), 7.61~7.35 (15H, m), 7.20~7.16 (2H, m) |
| 5 | δ = 8.55 (1H, d), 8.45 (1H, d), 8.30 (1H, d), 8.19~7.89 (11H, m), 7.77 (2H, m), 7.63~7.49 (12H, m), 7.38~7.35 (2H, m), 7.20~7.16 (2H, m) |
| 6 | δ = 8.95 (1H, d), 8.55~8.45 (3H, m), 8.30 (1H, d), 8.20~8.09 (4H, m), 8.00~7.89 (6H, m), 7.77 (3H, m), 7.62~7.35 (12H, m), 7.20~7.16 (2H, m) |
| 7 | δ = 8.55 (1H, d), 8.45 (1H, d), 8.30 (1H, d), 8.19~8.09 (3H, m), 8.00~7.89 (8H, m), 7.78~7.77 (3H, m), 7.62~7.49 (10H, m), 7.38~7.16 (5H, m), 1.69 (6H, s) |
| 8 | δ = 8.55 (1H, d), 8.45 (1H, d), 8.30 (1H, d), 8.19~8.13 (2H, m), 8.00~7.89 (7H, m), 7.78~7.77 (3H, m), 7.65~7.16 (17H, m), 1.69 (6H, s) |
| 9 | δ = 8.55 (1H, d), 8.45 (2H, d), 8.30 (1H, d), 8.19~8.12 (4H, m), 8.00~7.89 (8H, m), 7.77 (2H, m), 7.62~7.49 (11H, m), 7.35 (1H, t), 7.21~7.16 (2H, m) |
| 10 | δ = 8.55 (2H, d), 8.45 (2H, d), 8.32~8.30 (2H, m), 8.19 (1H, d), 8.12 (1H, d), 8.00~7.89 (7H, m), 7.77~7.49 (14H, m), 7.35 (1H, t), 7.21~7.16 (2H, m) |
| 11 | δ = 8.55 (1H, d), 8.45 (1H, d), 8.30 (1H, d), 8.19 (1H, d), 8.13 (1H, d), 8.00~7.77 (12H, m), 7.62~7.31 (13H, m), 7.20~7.16 (2H, m) |
| 12 | δ = 8.55 (1H, d), 8.45 (1H, d), 8.30 (1H, d), 8.19~7.89 (11H, m), 7.77 (2H, m), 7.62~7.31 (14H, m), 7.20~7.16 (2H, m) |

TABLE 4

| Compound | FD-Mass | Compound | FD-Mass |
|---|---|---|---|
| 1 | m/z = 742.94(C54H34N2S = 742.24) | 2 | m/z = 666.84(C48H30N2S = 666.21) |
| 3 | m/z = 742.94(C54H34N2S = 742.24) | 4 | m/z = 742.94(C54H34N2S = 742.24) |
| 5 | m/z = 716.90(C52H32N2S = 716.23) | 6 | m/z = 716.90(C52H32N2S = 716.23) |
| 7 | m/z = 783.00(C57H38N2S = 782.28) | 8 | m/z = 783.00(C57H38N2S = 782.28) |
| 9 | m/z = 772.98(C54H32N2S2 = 772.20) | 10 | m/z = 772.98(C54H32N2S2 = 772.20) |
| 11 | m/z = 756.92(C54H32N2OS = 756.22) | 12 | m/z = 756.92(C54H32N2OS = 756.22) |
| 13 | m/z = 666.84(C48H30N2S = 666.21) | 14 | m/z = 742.94(C54H34N2S = 742.24) |
| 15 | m/z = 742.94(C54H34N2S = 742.24) | 16 | m/z = 716.90(C52H32N2S = 716.23) |
| 17 | m/z = 716.90(C52H32N2S = 716.23) | 18 | m/z = 783.00(C57H38N2S = 782.28) |
| 19 | m/z = 783.00(C57H38N2S = 782.28) | 20 | m/z = 772.98(C54H32N2S2 = 772.20) |
| 21 | m/z = 756.92(C54H32N2OS = 756.22) | 22 | m/z = 756.92(C54H32N2OS = 756.22) |
| 23 | m/z = 772.98(C54H32N2S2 = 772.20) | 24 | m/z = 666.84(C48H30N2S = 666.21) |
| 25 | m/z = 742.94(C54H34N2S = 742.24) | 26 | m/z = 742.94(C54H34N2S = 742.24) |
| 27 | m/z = 783.00(C57H38N2S = 782.28) | 28 | m/z = 772.98(C54H32N2S2 = 772.20) |
| 29 | m/z = 756.92(C54H32N2OS = 756.22) | 30 | m/z = 772.98(C54H32N2S2 = 772.20) |
| 31 | m/z = 783.00(C57H38N2S = 782.28) | 32 | m/z = 756.92(C54H32N2OS = 756.22) |
| 33 | m/z = 666.84(C48H30N2S = 666.21) | 34 | m/z = 742.947(C54H34N2S = 742.24) |
| 35 | m/z = 742.94(C54H34N2S = 742.24) | 36 | m/z = 772.98(C54H32N2S2 = 772.20) |
| 37 | m/z = 756.92(C54H32N2OS = 756.22) | 38 | m/z = 772.98(C54H32N2S2 = 772.20) |
| 39 | m/z = 783.00(C57H38N2S = 782.28) | 40 | m/z = 756.92(C54H32N2OS = 756.22) |
| 41 | m/z = 666.84(C48H30N2S = 666.21) | 42 | m/z = 742.94(C54H34N2S = 742.24) |
| 43 | m/z = 742.94(C54H34N2S = 742.24) | 44 | m/z = 772.98(C54H32N2S2 = 772.20) |
| 45 | m/z = 756.92(C54H32N2OS = 756.22) | 46 | m/z = 772.98(C54H32N2S2 = 772.20) |
| 47 | m/z = 783.00(C57H38N2S = 782.28) | 48 | m/z = 756.92(C54H32N2OS = 756.22) |
| 49 | m/z = 666.84(C48H30N2S = 666.21) | 50 | m/z = 742.94(C54H34N2S = 742.24) |
| 51 | m/z = 742.94(C54H34N2S = 742.24) | 52 | m/z = 772.98(C54H32N2S2 = 772.20) |
| 53 | m/z = 756.92(C54H32N2OS = 756.22) | 54 | m/z = 772.98(C54H32N2S2 = 772.20) |
| 55 | m/z = 783.00(C57H38N2S = 782.28) | 56 | m/z = 756.92(C54H32N2OS = 756.22) |
| 57 | m/z = 666.84(C48H30N2S = 666.21) | 58 | m/z = 742.94(C54H34N2S = 742.24) |
| 59 | m/z = 742.94(C54H34N2S = 742.24) | 60 | m/z = 772.98(C54H32N2S2 = 772.20) |
| 61 | m/z = 756.92(C54H32N2OS = 756.22) | 62 | m/z = 772.98(C54H32N2S2 = 772.20) |
| 63 | m/z = 783.00(C57H38N2S = 782.28) | 64 | m/z = 756.92(C54H32N2OS = 756.22) |
| 65 | m/z = 666.84(C48H30N2S = 666.21) | 66 | m/z = 742.94(C54H34N2S = 742.24) |
| 67 | m/z = 742.94(C54H34N2S = 742.24) | 68 | m/z = 772.98(C54H32N2S2 = 772.20) |
| 69 | m/z = 756.92(C54H32N2OS = 756.22) | 70 | m/z = 772.98(C54H32N2S2 = 772.20) |
| 71 | m/z = 783.00(C57H38N2S = 782.28) | 72 | m/z = 756.92(C54H32N2OS = 756.22) |
| 73 | m/z = 666.84(C48H30N2S = 666.21) | 74 | m/z = 742.94(C54H34N2S = 742.24) |
| 75 | m/z = 742.94(C54H34N2S = 742.24) | 76 | m/z = 772.98(C54H32N2S2 = 772.20) |
| 77 | m/z = 756.92(C54H32N2OS = 756.22) | 78 | m/z = 772.98(C54H32N2S2 = 772.20) |
| 79 | m/z = 783.00(C57H38N2S = 782.28) | 80 | m/z = 756.92(C54H32N2OS = 756.22) |
| 81 | m/z = 666.84(C48H30N2S = 666.21) | 82 | m/z = 742.94(C54H34N2S = 742.24) |
| 83 | m/z = 742.94(C54H34N2S = 742.24) | 84 | m/z = 772.98(C54H32N2S2 = 772.20) |
| 85 | m/z = 756.92(C54H32N2OS = 756.22) | 86 | m/z = 772.98(C54H32N2S2 = 772.20) |
| 87 | m/z = 783.00(C57H38N2S = 782.28) | 88 | m/z = 756.92(C54H32N2OS = 756.22) |
| 89 | m/z = 666.84(C48H30N2S = 666.21) | 90 | m/z = 742.94(C54H34N2S = 742.24) |
| 91 | m/z = 742.94(C54H34N2S = 742.24) | 92 | m/z = 772.98(C54H32N2S2 = 772.20) |
| 93 | m/z = 756.92(C54H32N2OS = 756.22) | 94 | m/z = 772.98(C54H32N2S2 = 772.20) |
| 95 | m/z = 783.00(C57H38N2S = 782.28) | 96 | m/z = 756.92(C54H32N2OS = 756.22) |
| 97 | m/z = 666.84(C48H30N2S = 666.21) | 98 | m/z = 742.94(C54H34N2S = 742.24) |
| 99 | m/z = 742.94(C54H34N2S = 742.24) | 100 | m/z = 772.98(C54H32N2S2 = 772.20) |

TABLE 4-continued

| Compound | FD-Mass | Compound | FD-Mass |
|---|---|---|---|
| 101 | m/z = 756.92(C54H32N2OS = 756.22) | 102 | m/z = 772.98(C54H32N2S2 = 772.20) |
| 103 | m/z = 783.00(C57H38N2S = 782.28) | 104 | m/z = 756.92(C54H32N2OS = 756.22) |

Table 3 shows NMR values, and Table 4 shows measured values by field desorption mass spectrometry (FD-MS).

Experimental Examples

1) Manufacture of Organic Light Emitting Device

A glass substrate thinly coated with ITO to have a thickness of 1,500 Å was ultrasonically washed with distilled water. When the washing with distilled water is finished, the glass substrate was ultrasonically washed with a solvent such as acetone, methanol, and isopropyl alcohol, was dried and then was subjected to UVO treatment for 5 minutes by using UV in a UV washing machine. Thereafter, the substrate was transferred to a plasma washing machine (PT), and then was subjected to plasma treatment in a vacuum state for an ITO work function and in order to remove a residual film, and was transferred to a thermal deposition equipment for organic deposition. As the common layers, the hole injection layer 4,4',4''-tris[2-naphthyl(phenyl)amino]triphenylamine (2-TNATA) and the hole transporting layer N,N'-di(1-naphthyl)-N,N'-diphenyl-(1,1'-biphenyl)-4,4'-diamine (NPB) were formed on the ITO transparent electrode (positive electrode).

A light emitting layer was thermally vacuum deposited thereon as follows. The light emitting layer was deposited to have a thickness of 400 Å by using a compound described in the following Table 5 as a host and tris(2-phenylpyridine) iridium (Ir(ppy)$_3$) as a green phosphorescent dopant to dope the host with Ir(ppy)$_3$ in an amount of 7%. Thereafter, BCP as a hole blocking layer was deposited to have a thickness of 60 Å, and Alq$_3$ as an electron transporting layer was deposited to have a thickness of 200 Å thereon. Finally, lithium fluoride (LiF) was deposited to have a thickness of 10 Å on the electron transporting layer to form an electron injection layer, and then aluminum (Al) was deposited to have a thickness of 1,200 Å on the electron injection layer to form a negative electrode, thereby manufacturing an organic light emitting device.

Meanwhile, all the organic compounds required for manufacturing an OLED were subjected to vacuum sublimed purification under $10^{-6}$ to $10^{-8}$ torr for each material, and then used for the manufacture of OLED.

2) Driving Voltage and Light Emitting Efficiency of Organic Light Emitting Device For the organic light emitting device manufactured as described above, electroluminescence (EL) characteristics were measured by M7000 manufactured by McScience Inc., and based on the measurement result thereof, T$_{90}$ was measured by a service life measurement equipment (M6000) manufactured by McScience Inc., when the reference luminance was 3,000 cd/m$^2$. Characteristics of the organic light emitting device of the present invention are as shown in the following Table 5.

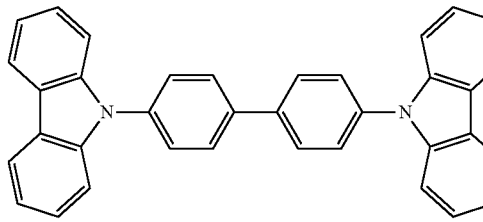

[CBP]

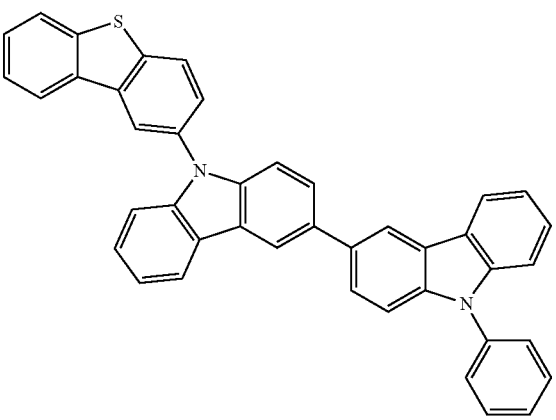

[ref 2]

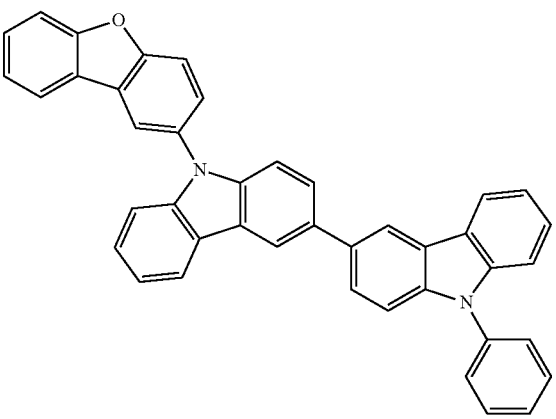

[ref 3]

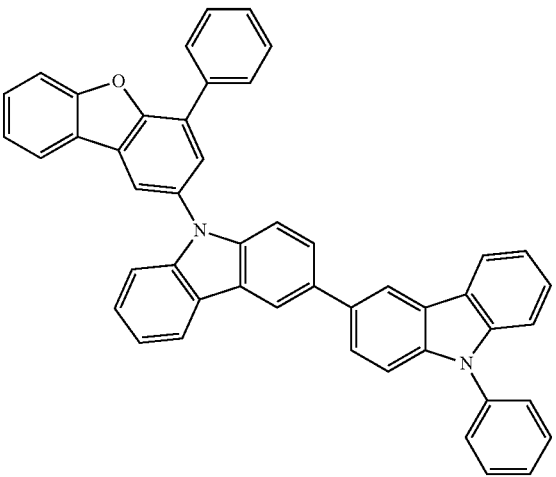

[ref 4]

[ref 5]

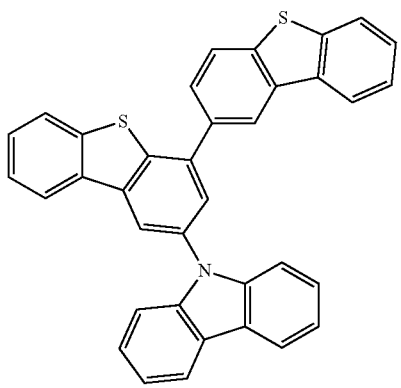

[ref 6]

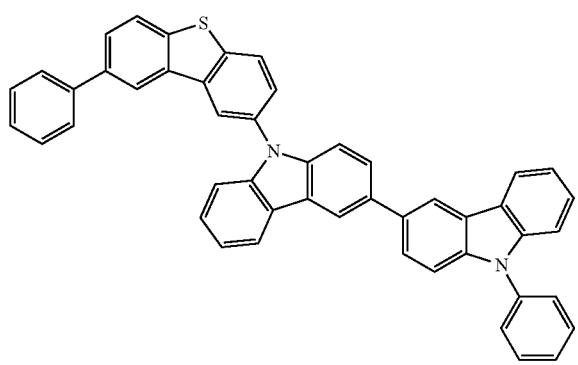

TABLE 5

| Compound | Driving voltage (V) | Efficiency (cd/A) | Color coordinate (x, y) | Service life ($T_{90}$) |
|---|---|---|---|---|
| Example 1 | 1 | 4.02 | 65.2 | (0.292, 0.694) | 240 |
| Example 2 | 2 | 4.05 | 67.2 | (0.294, 0.694) | 272 |
| Example 3 | 3 | 3.90 | 68.9 | (0.273, 0.673) | 191 |
| Example 4 | 4 | 4.30 | 62.5 | (0.313, 0.683) | 241 |
| Example 5 | 5 | 4.29 | 61.1 | (0.291, 0.654) | 201 |
| Example 6 | 6 | 4.39 | 62.1 | (0.301, 0.654) | 203 |
| Example 7 | 7 | 4.39 | 62.1 | (0.291, 0.684) | 193 |
| Example 8 | 8 | 4.19 | 66.1 | (0.317, 0.653) | 213 |
| Example 9 | 9 | 4.40 | 63.2 | (0.295, 0.674) | 210 |
| Example 10 | 10 | 3.88 | 69.9 | (0.290, 0.632) | 234 |
| Example 11 | 11 | 4.01 | 66.6 | (0.286, 0.645) | 219 |
| Example 12 | 12 | 3.93 | 68.3 | (0.312, 0.653) | 185 |
| Example 13 | 13 | 4.35 | 67.7 | (0.291, 0.684) | 195 |
| Example 14 | 14 | 4.25 | 63.7 | (0.290, 0.684) | 200 |
| Example 15 | 24 | 3.80 | 70.2 | (0.284, 0.690) | 212 |
| Example 16 | 26 | 4.29 | 65.4 | (0.285, 0.671) | 227 |
| Example 17 | 33 | 4.09 | 67.0 | (0.336, 0.661) | 240 |
| Example 18 | 34 | 4.25 | 65.7 | (0.282, 0.645) | 216 |
| Example 19 | 41 | 4.05 | 63.2 | (0.271, 0.655) | 249 |
| Example 20 | 42 | 3.90 | 69.9 | (0.314, 0.702) | 220 |
| Example 21 | 49 | 4.48 | 64.7 | (0.331, 0.651) | 232 |
| Example 22 | 50 | 3.98 | 71.2 | (0.304, 0.682) | 225 |
| Example 23 | 57 | 4.02 | 62.7 | (0.281, 0.655) | 214 |
| Example 24 | 58 | 3.79 | 72.5 | (0.291, 0.672) | 237 |
| Example 25 | 65 | 4.08 | 74.1 | (0.321, 0.667) | 198 |
| Example 26 | 66 | 4.35 | 64.2 | (0.284, 0.645) | 171 |
| Example 27 | 73 | 4.17 | 65.8 | (0.291, 0.692) | 188 |
| Example 28 | 74 | 3.81 | 64.7 | (0.293, 0.692) | 248 |
| Example 29 | 81 | 3.93 | 67.0 | (0.281, 0.675) | 212 |
| Example 30 | 82 | 4.02 | 62.7 | (0.331, 0.672) | 258 |
| Example 31 | 89 | 4.59 | 74.1 | (0.322, 0.645) | 298 |
| Example 32 | 90 | 4.22 | 64.2 | (0.291, 0.692) | 191 |
| Example 33 | 97 | 4.29 | 65.1 | (0.281, 0.655) | 181 |
| Example 34 | 98 | 4.49 | 67.0 | (0.291, 0.642) | 212 |

TABLE 5-continued

| Compound | Driving voltage (V) | Efficiency (cd/A) | Color coordinate (x, y) | Service life ($T_{90}$) |
|---|---|---|---|---|
| Comparative Example 1 | CBP | 5.89 | 41.1 | (0.328, 0.681) | 52 |
| Comparative Example 2 | Ref 2 | 4.83 | 62.4 | (0.318, 0.671) | 95 |
| Comparative Example 3 | Ref 3 | 4.33 | 65.5 | (0.284, 0.651) | 62 |
| Comparative Example 4 | Ref 4 | 4.13 | 68.5 | (0.328, 0.641) | 72 |
| Comparative Example 5 | Ref 5 | 4.93 | 61.4 | (0.308, 0.641) | 54 |
| Comparative Example 6 | Ref 6 | 4.21 | 65.1 | (0.276, 0.631) | 63 |

It could be confirmed that the compound of the present invention exhibited particularly better service life characteristics than Comparative Examples 1 to 6 in the evaluation of the phosphorescent green devices. Further, when the compound of the present invention is compared with Comparative Examples 3 and 4, it is thought that since dibenzothiophene shows stronger aromaticity than dibenzofuran, dibenzothiophene is structurally stable and exhibits long service life characteristics for this reason, and when the compound of the present invention is compared with Comparative Examples 2 and 6, it is determined that in the case where a substituent is substituted at the No. 4 position of dibenzothiophene, dibenzothiophene serves as a protective group which protects the No. 4 position having good reactivity, and as a result, the molecular stability is increased, and long service life characteristics are exhibited. Furthermore, when the compound of the present invention is compared with Comparative Example 5, it can be confirmed that the compound of the present invention exhibits long service life characteristics because the biscarbazole has a better hole transporting capability than carbazole.

What is claimed is:

1. A hetero-cyclic compound represented by the following Chemical Formula 1:

[Chemical Formula 1]

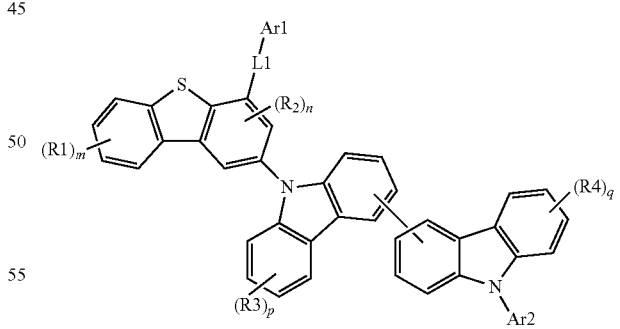

in Chemical Formula 1,
L1 is a direct bond or a substituted or unsubstituted $C_6$ to $C_{60}$ arylene group,
Ar1 is a substituted or unsubstituted $C_6$ to $C_{60}$ aryl group; or a substituted or unsubstituted $C_2$ to $C_{60}$ heteroaryl group comprising at least one of S and O,
Ar2 is a substituted or unsubstituted $C_6$ to $C_{60}$ aryl group; or a substituted or unsubstituted $C_2$ to $C_{60}$ heteroaryl group, R1 to R4 are the same as or different from each other, and are each independently selected from the group consisting of hydrogen; deuterium; a halogen group; —CN; a substituted or unsubstituted $C_1$ to $C_{60}$ alkyl group; a substituted or unsubstituted $C_2$ to $C_{60}$ alkenyl group; a substituted or unsubstituted $C_2$ to $C_{60}$ alkynyl group; a substituted or unsubstituted $C_1$ to $C_{60}$ alkoxy group; a substituted or unsubstituted $C_3$ to $C_{60}$ cycloalkyl group; a substituted or unsubstituted $C_2$ to $C_{60}$ heterocycloalkyl group; a substituted or unsubstituted $C_6$ to $C_{60}$ aryl group; a substituted or unsubstituted $C_2$ to $C_{60}$ heteroaryl group; —SiRR'R"; —P(=O)RR'; and an amine group which is unsubstituted or substituted with a $C_1$ to $C_{20}$ alkyl group, a substituted or unsubstituted $C_6$ to $C_{60}$ aryl group, or a $C_2$ to $C_{60}$ heteroaryl group, or two or more adjacent groups are bonded to each other to form a substituted or unsubstituted aliphatic or aromatic hydrocarbon ring, R, R', and R" are the same as or different from each other, and are each independently hydrogen; deuterium; —CN; a substituted or unsubstituted $C_1$ to $C_{60}$ alkyl group; a substituted or unsubstituted $C_3$ to $C_{60}$ cycloalkyl group; a substituted or unsubstituted $C_6$ to $C_{60}$ aryl group; or a substituted or unsubstituted $C_2$ to $C_{60}$ heteroaryl group, m, p, and q are each independently an integer from 0 to 4, and n is an integer from 0 to 2.

2. The hetero-cyclic compound of claim 1, wherein Chemical Formula 1 is represented by any one of the following Chemical Formulae 2 to 13:

[Chemical Formula 2]

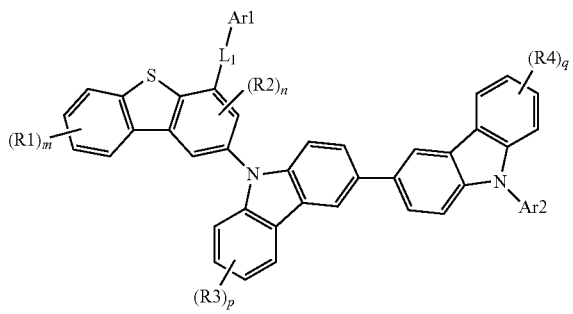

[Chemical Formula 3]

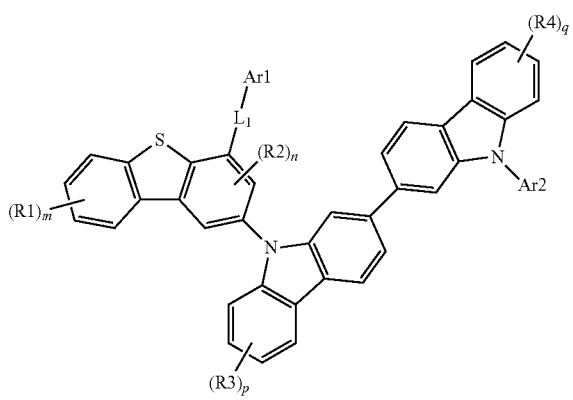

[Chemical Formula 4]

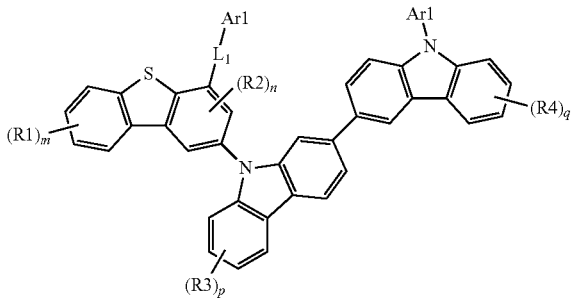

[Chemical Formula 5]

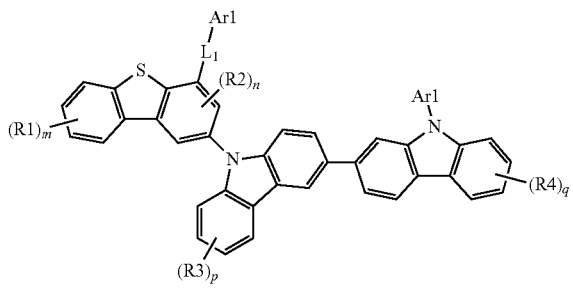

[Chemical Formula 6]

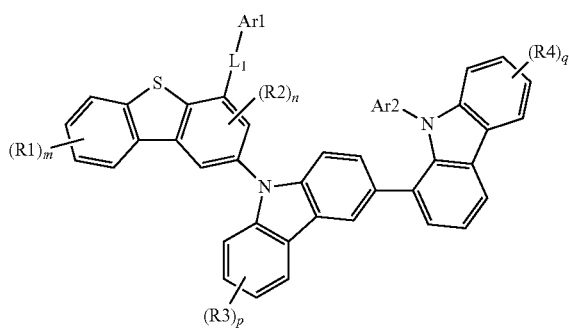

[Chemical Formula 7]

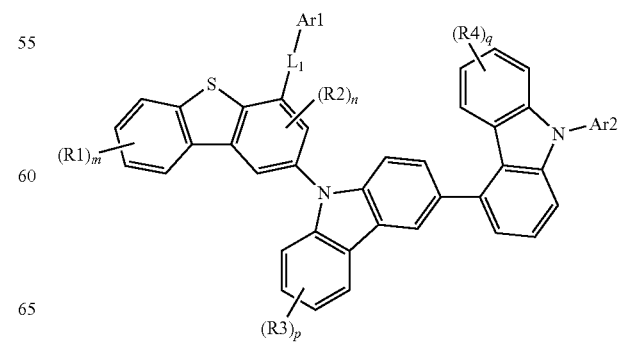

[Chemical Formula 8]

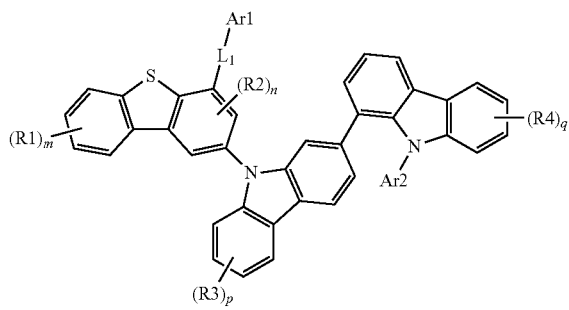

[Chemical Formula 9]

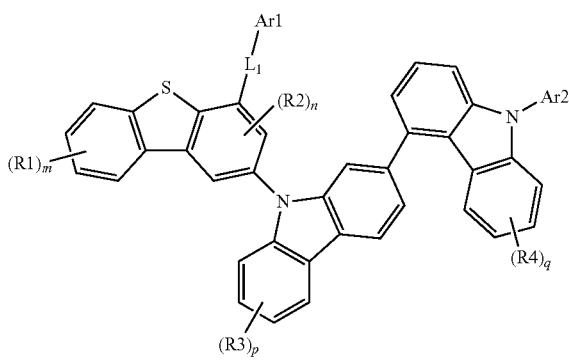

[Chemical Formula 10]

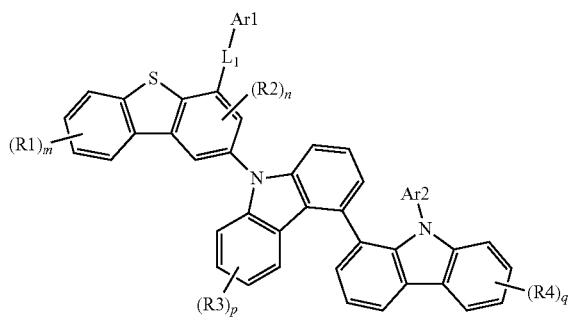

[Chemical Formula 11]

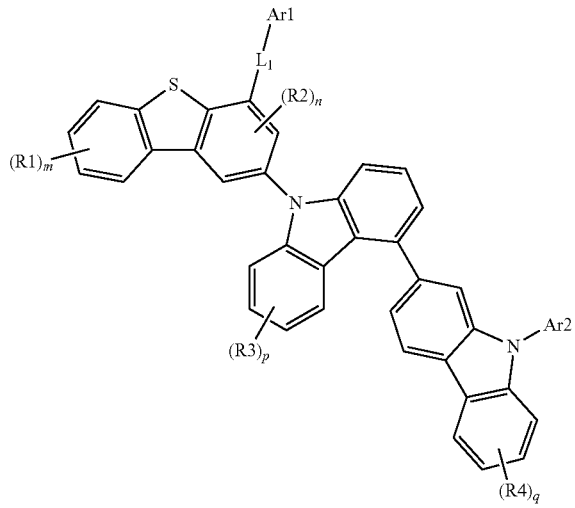

[Chemical Formula 12]

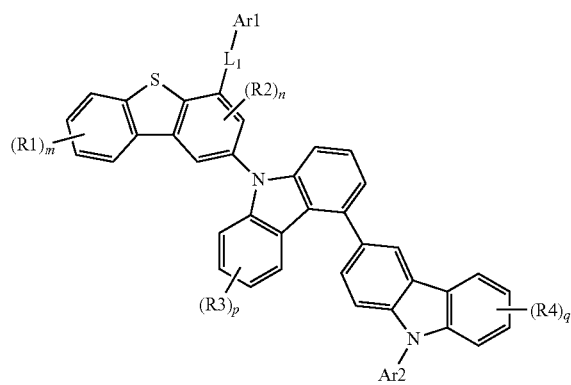

[Chemical Formula 13]

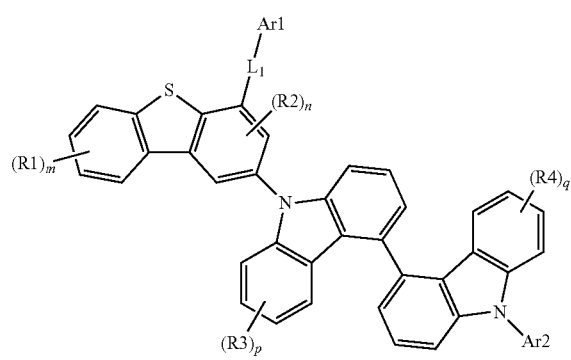

in Chemical Formulae 2 to 13, the definitions of L1, Ar1, Ar2, R1 to R4, m, n, p, and q are the same as those in Chemical Formula 1.

3. The hetero-cyclic compound of claim 1, wherein Ar1 of Chemical Formula 1 is a phenyl group, a biphenyl group, a naphthyl group, a fluorene group in which an alkyl group is substituted, a dibenzothiophene group, or a dibenzofuran group.

4. The hetero-cyclic compound of claim 1, wherein Ar2 of Chemical Formula 1 is a phenyl group.

5. The hetero-cyclic compound of claim 1, wherein R1 and R4 of Chemical Formula 1 are each independently hydrogen or deuterium.

6. The hetero-cyclic compound of claim 1, wherein Chemical Formula 1 is represented by any one of the following compounds:
1
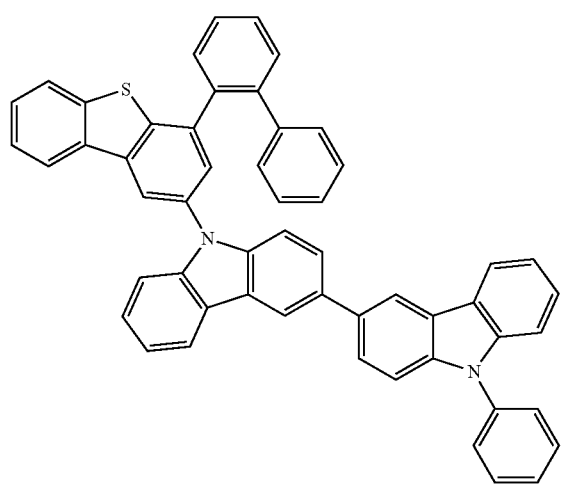
2
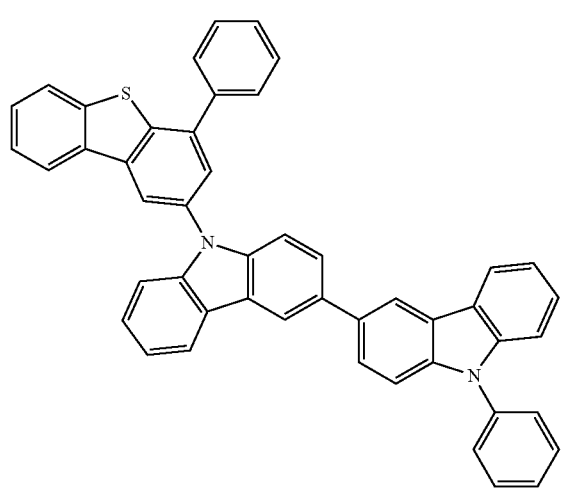
3
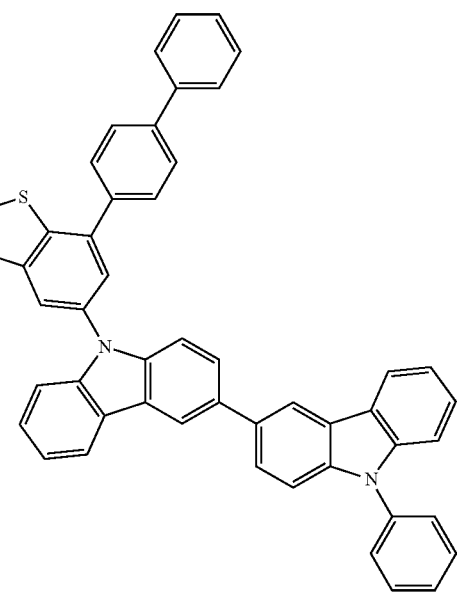
4
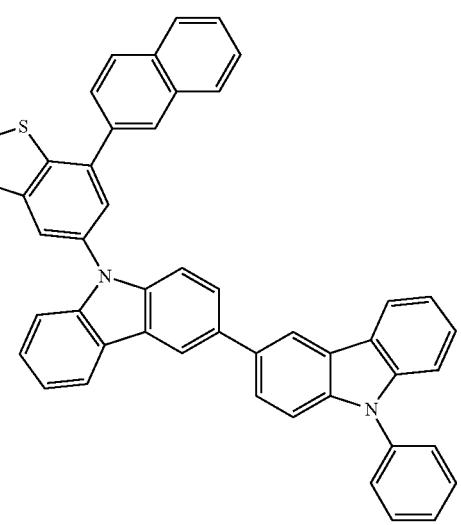
5

-continued
6
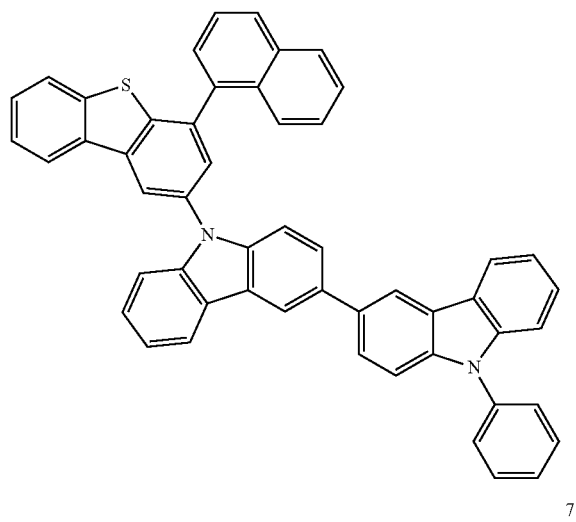
7
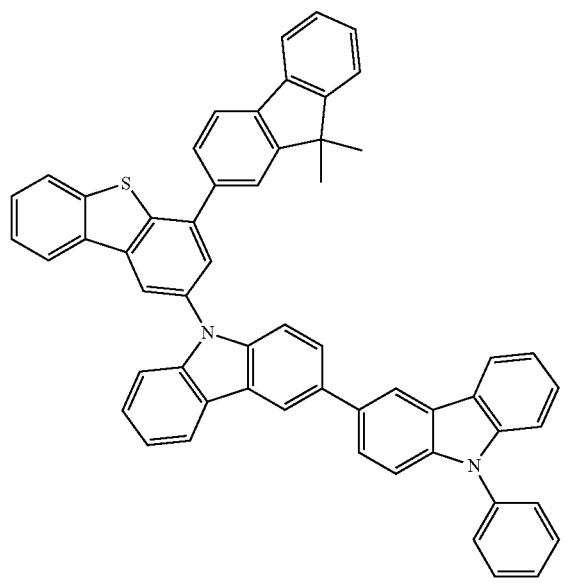
8
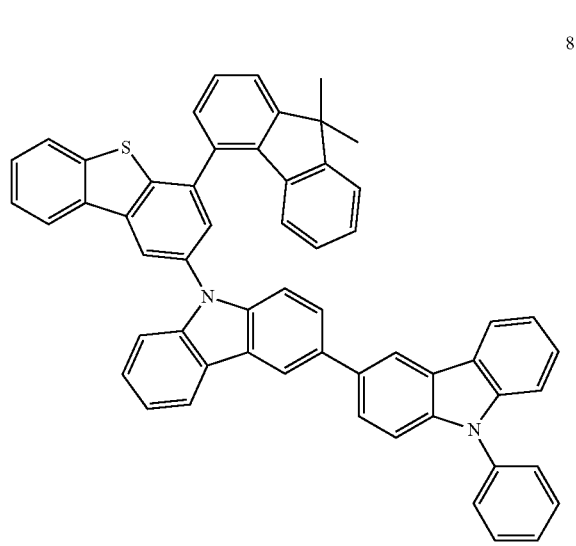
-continued
9
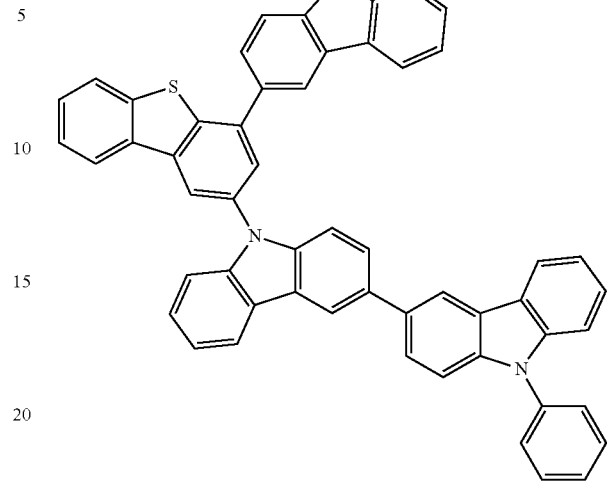
10
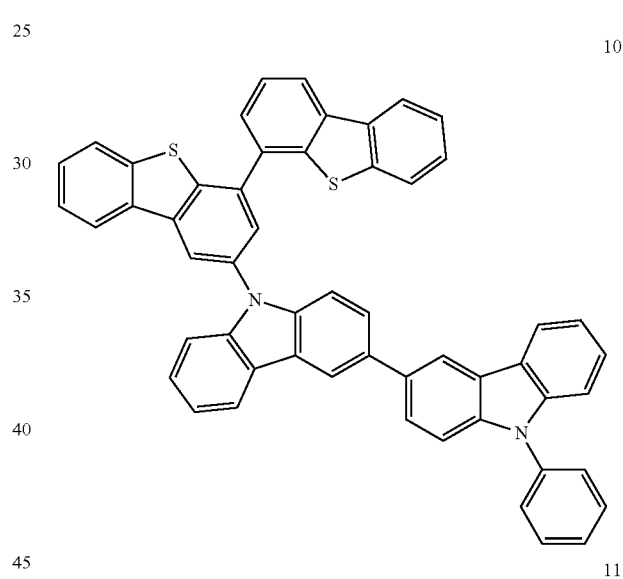
11
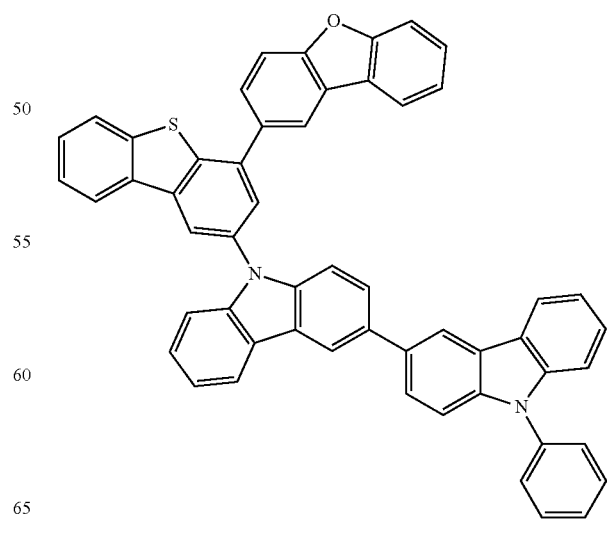

12
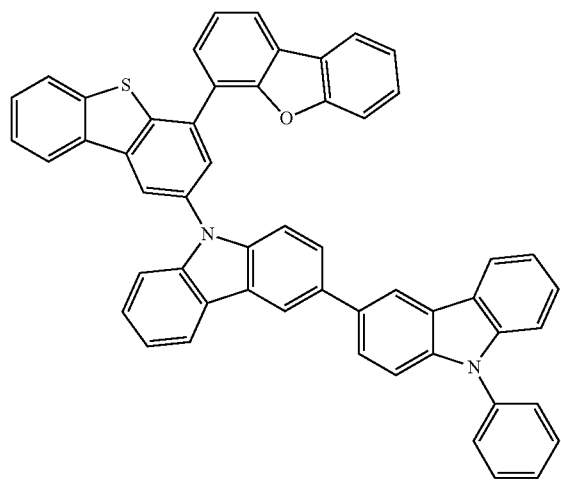
13
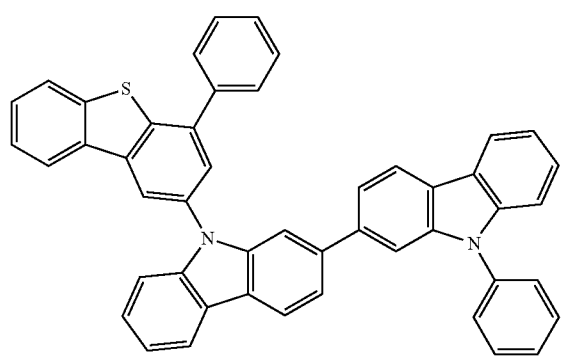
14
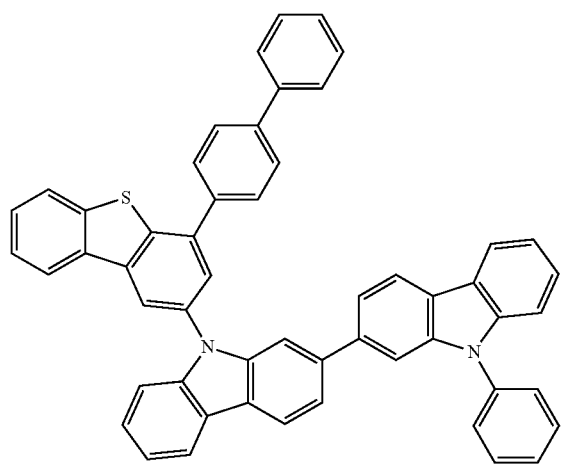
15
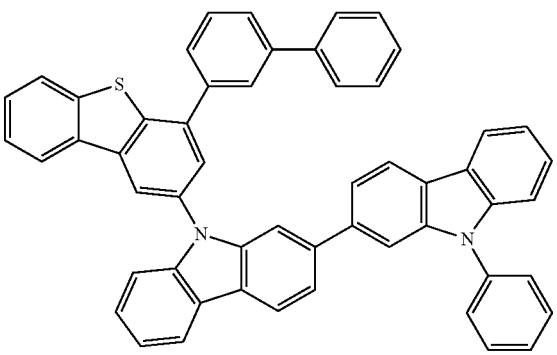
16
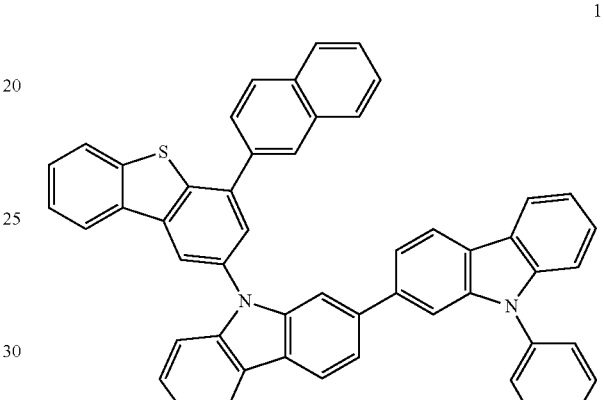
17
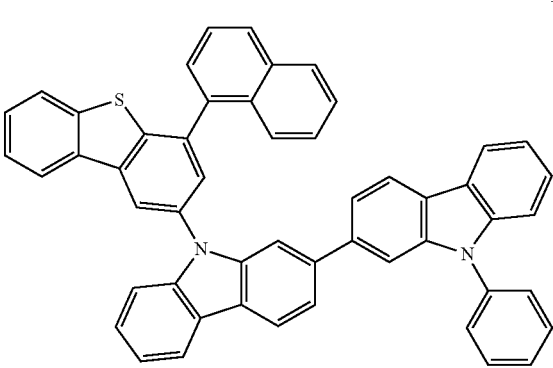
18
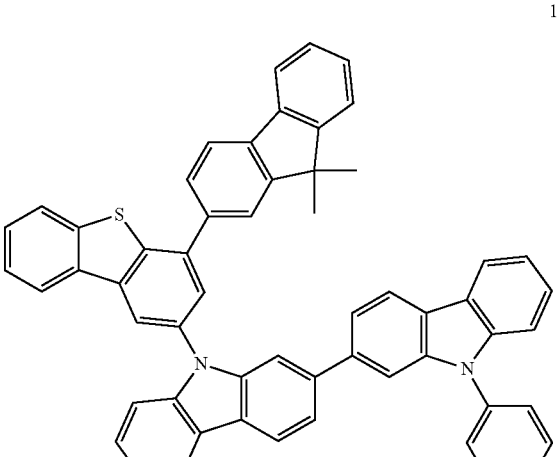

19
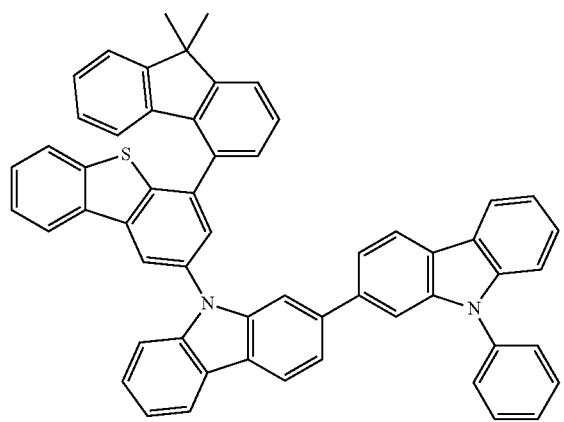
20
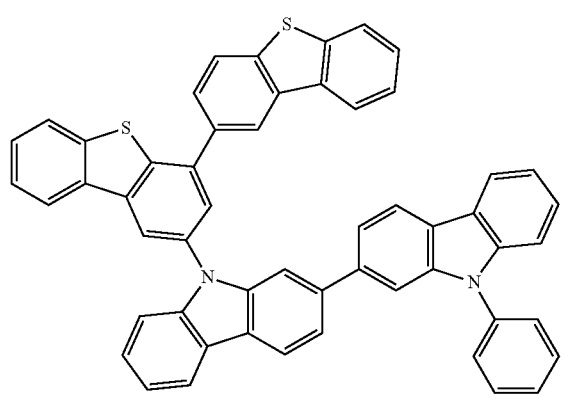
21
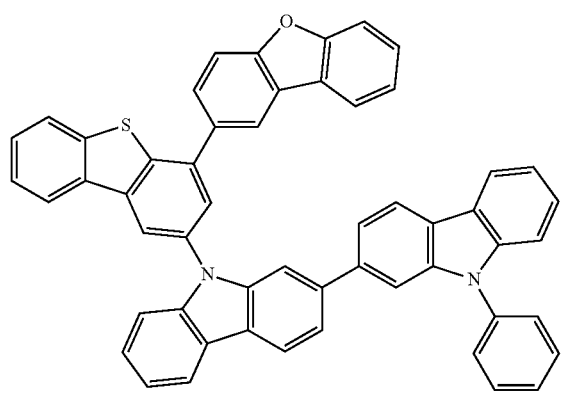
22
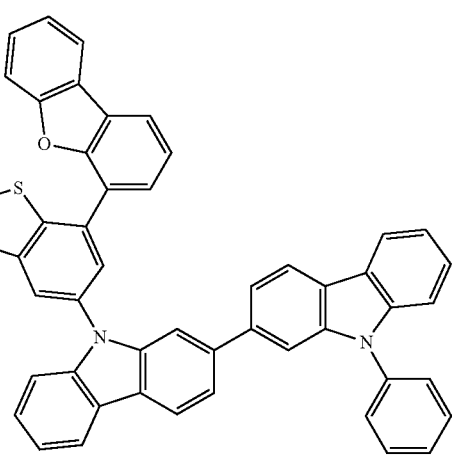
23
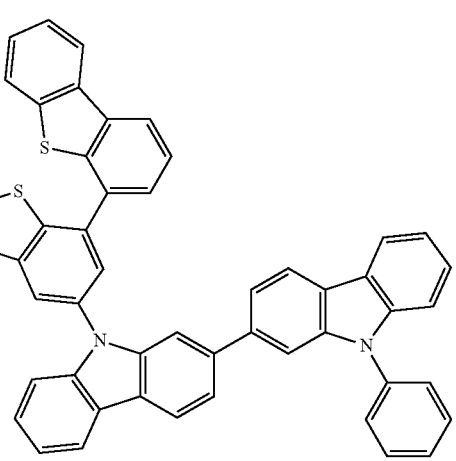
24
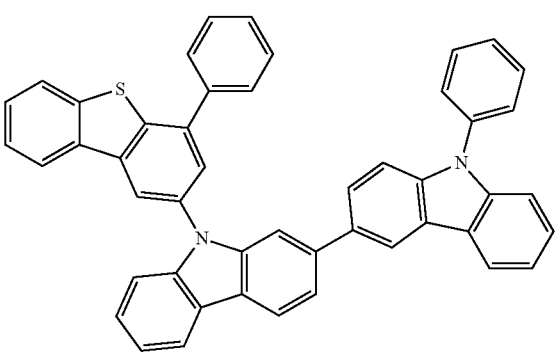

25
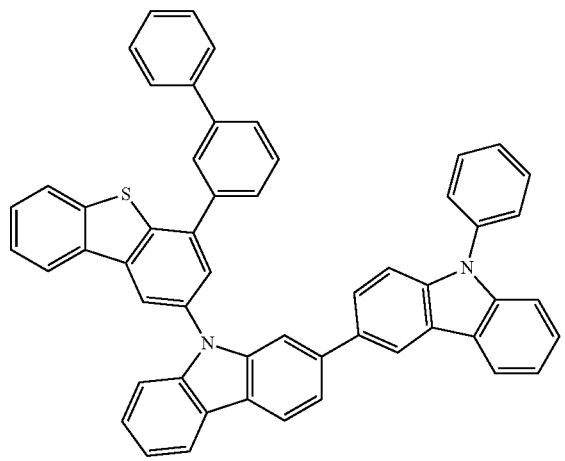
26
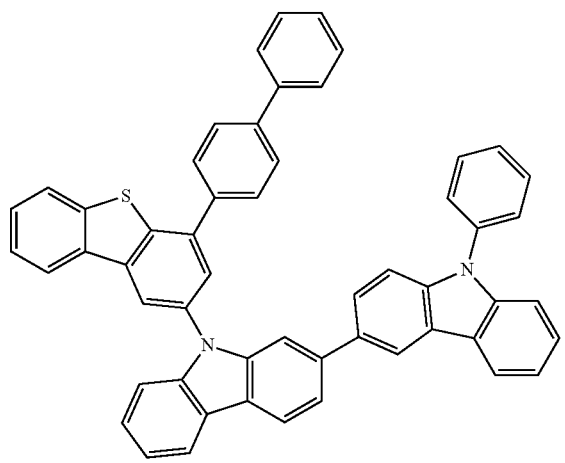
27
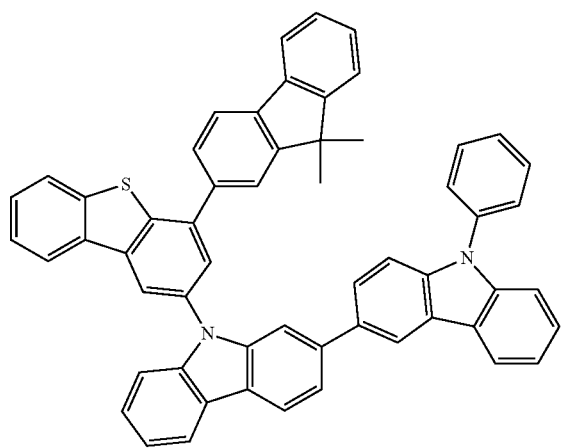
28
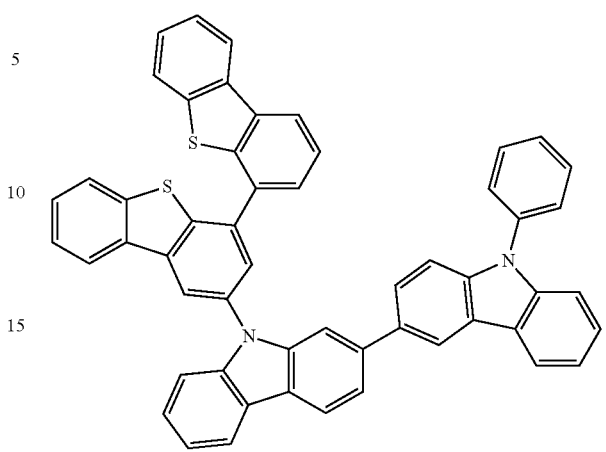
29
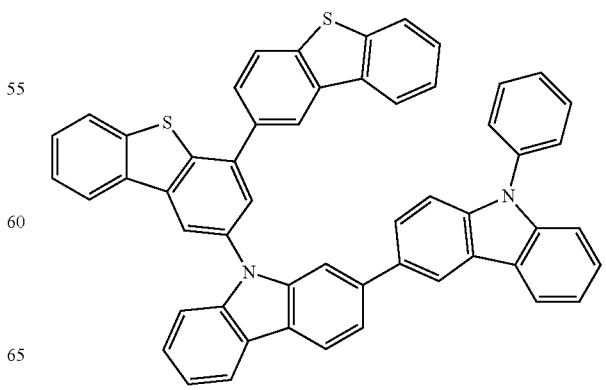

31
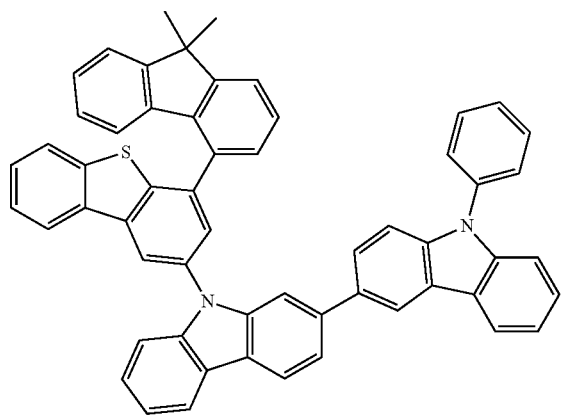
32
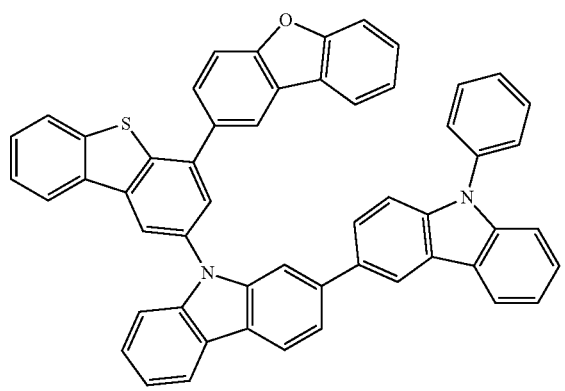
33
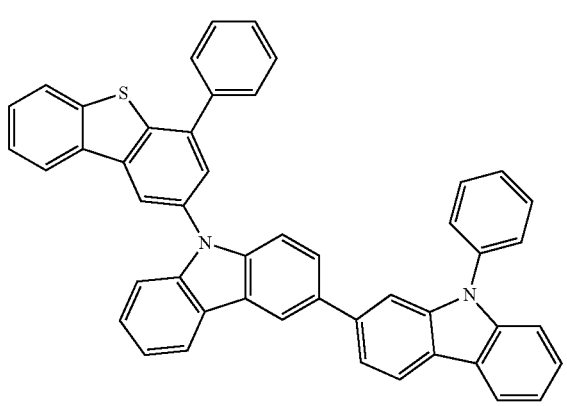
34
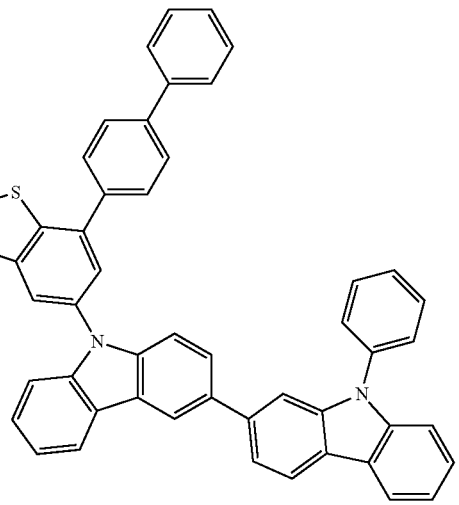
35
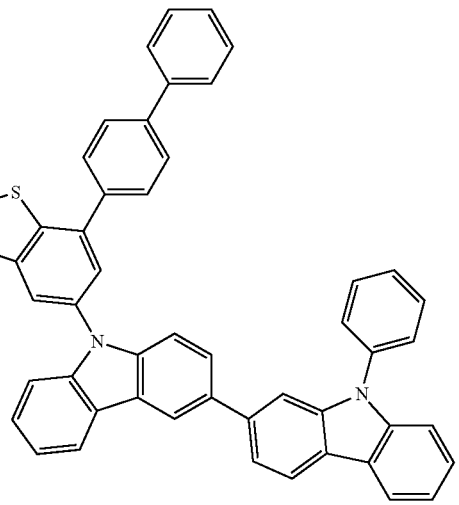
36
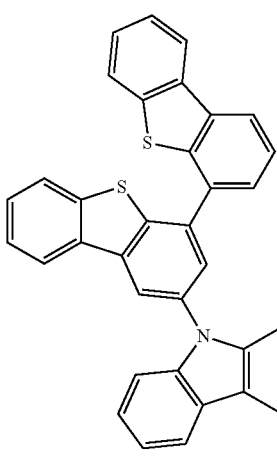

37
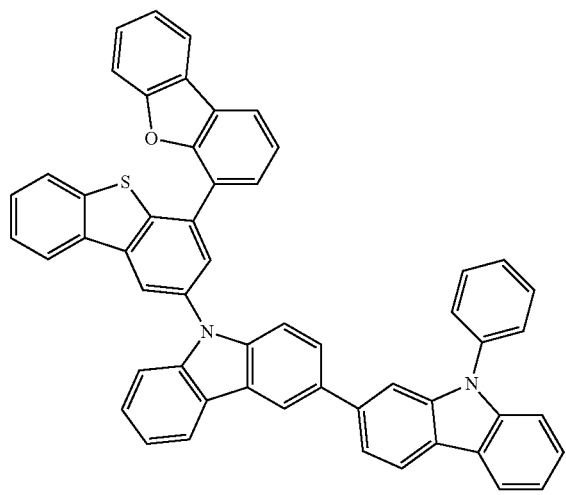
38
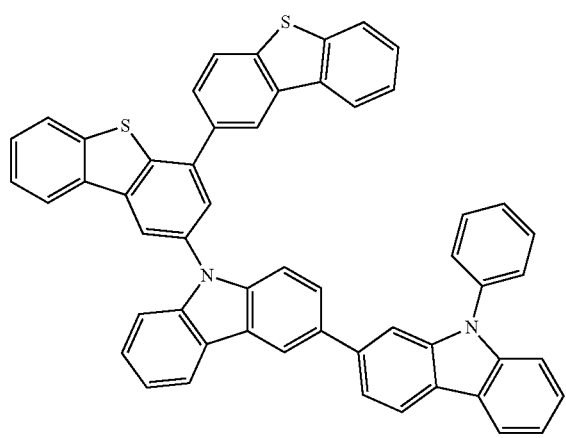
39
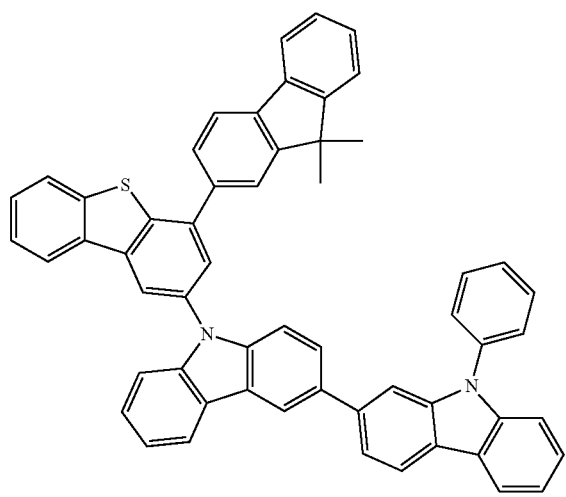
40
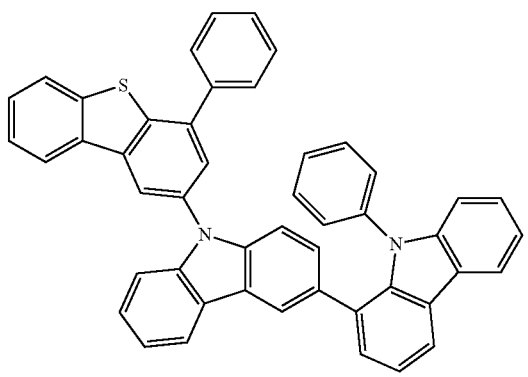
41
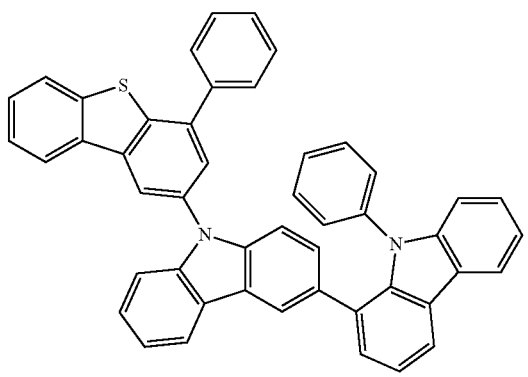
42
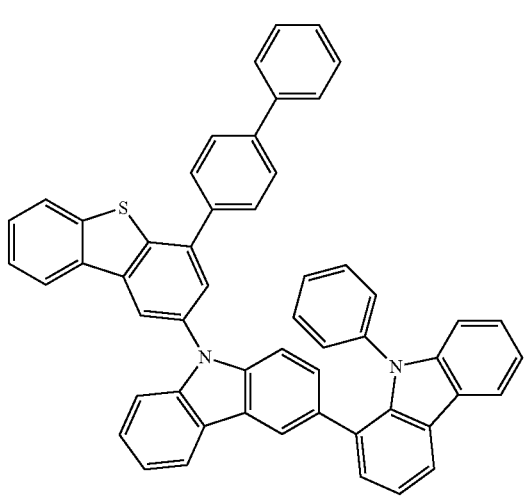

105
-continued
43
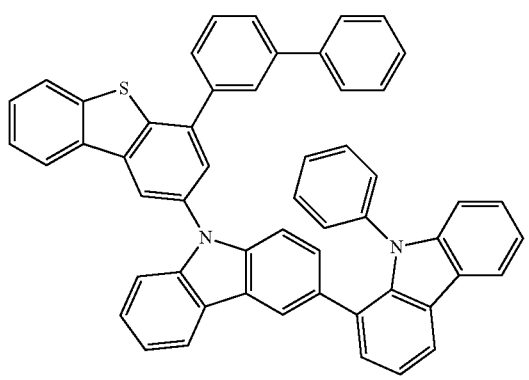
44
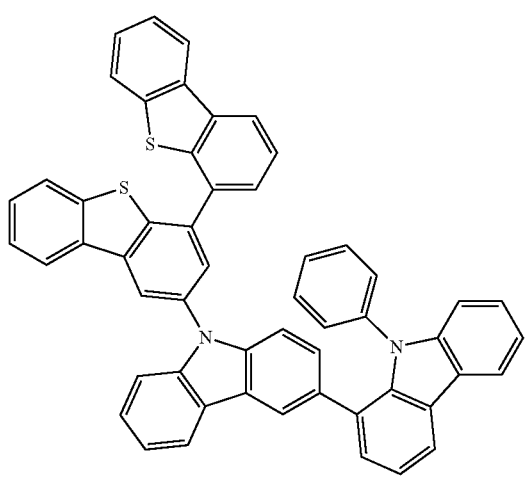
45
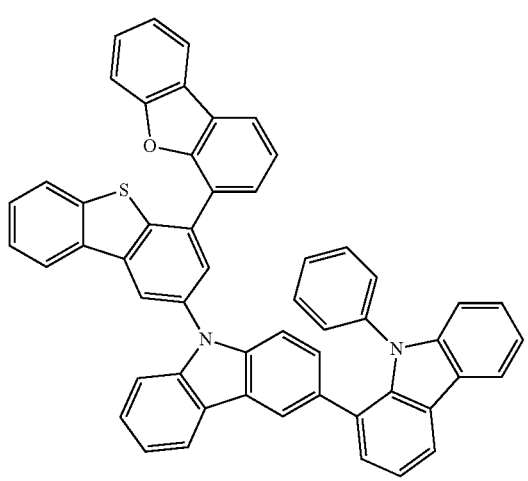
106
-continued
46
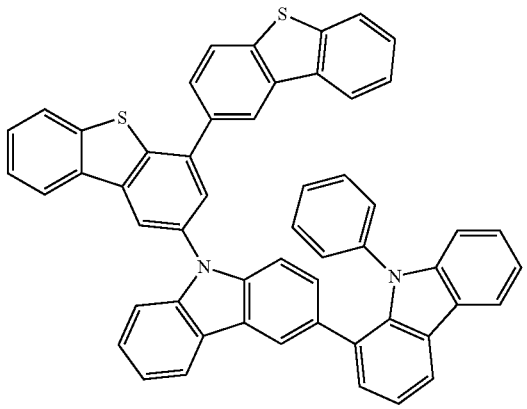
47
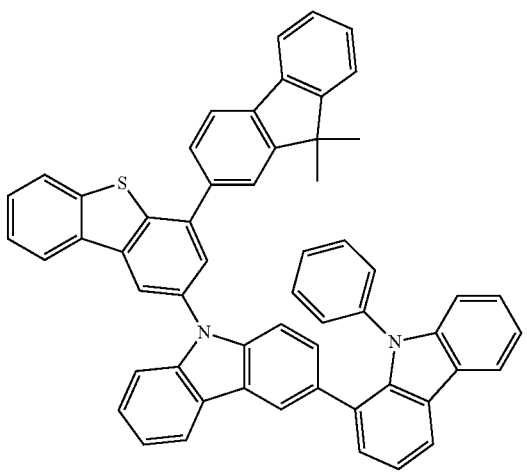
48
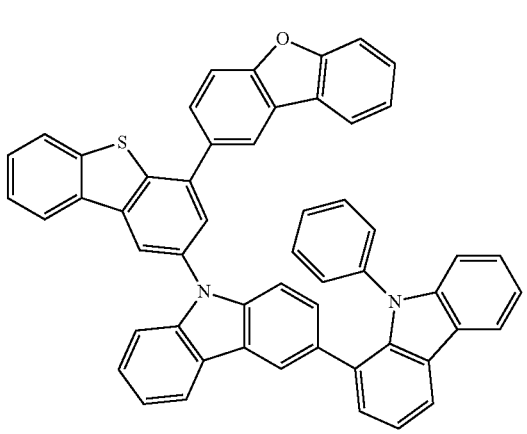

49
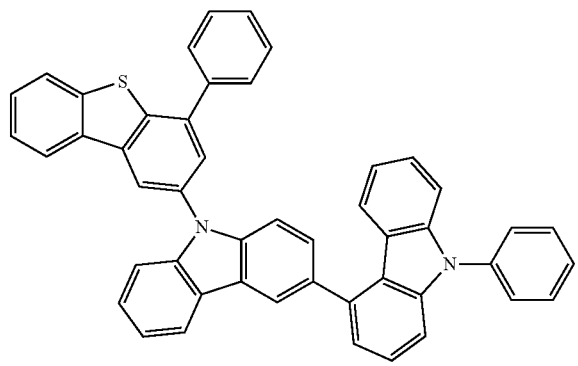
50
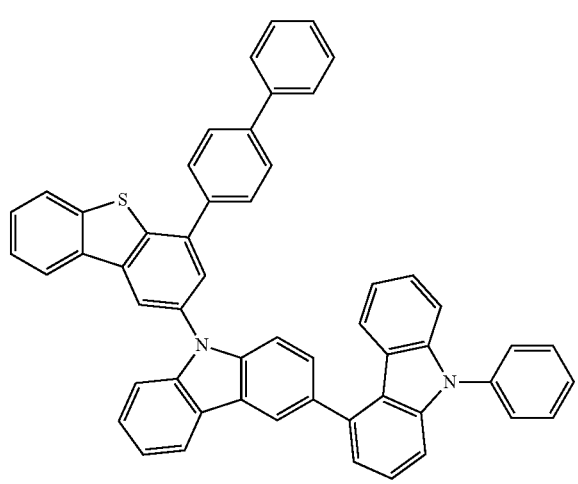
51
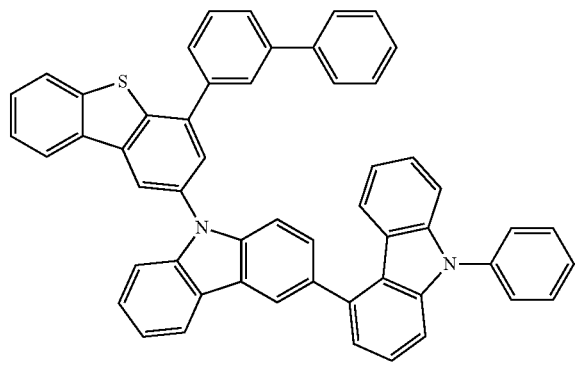
52
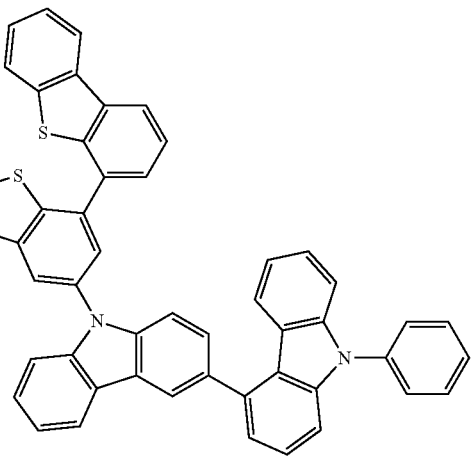
53
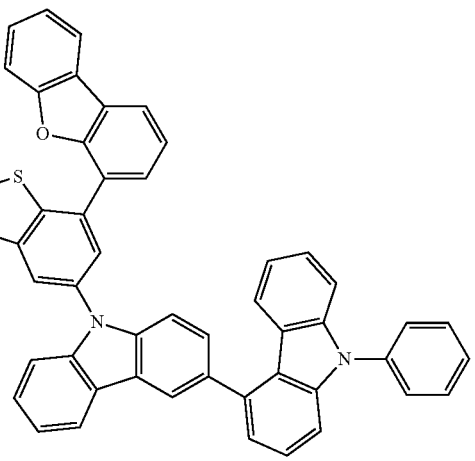
54
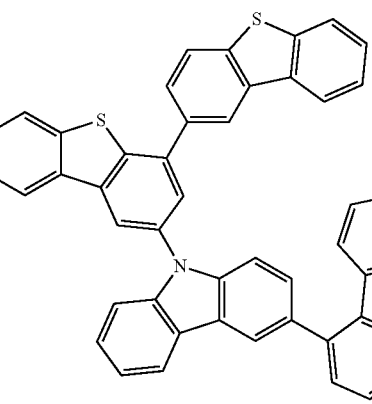

109
-continued
55
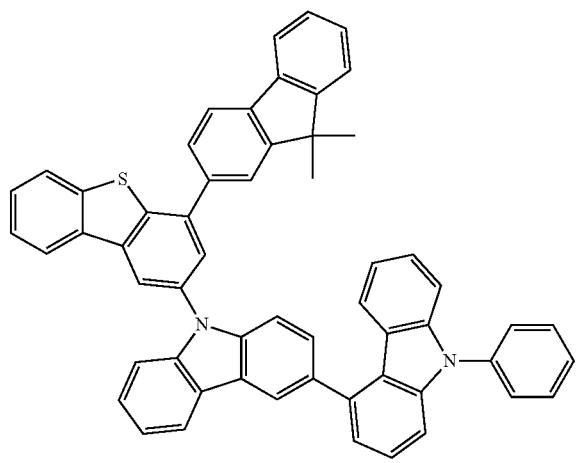
56
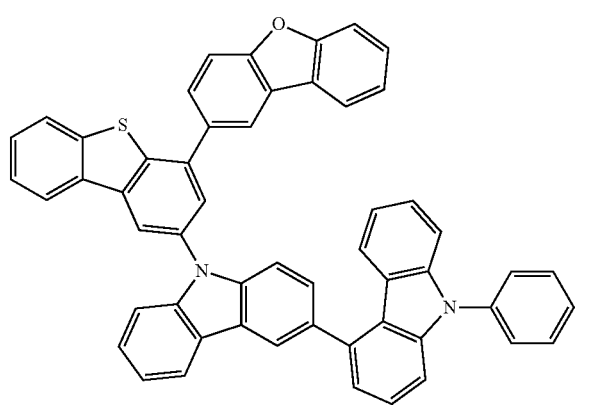
57
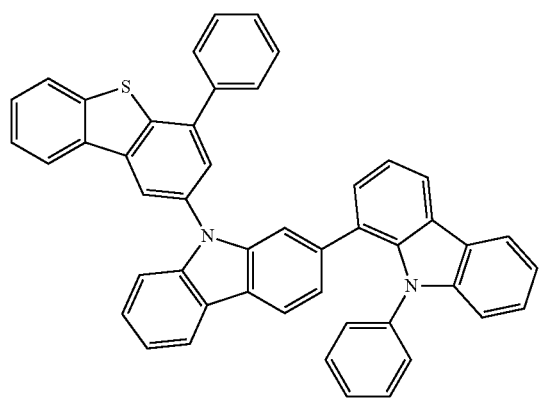
110
-continued
58
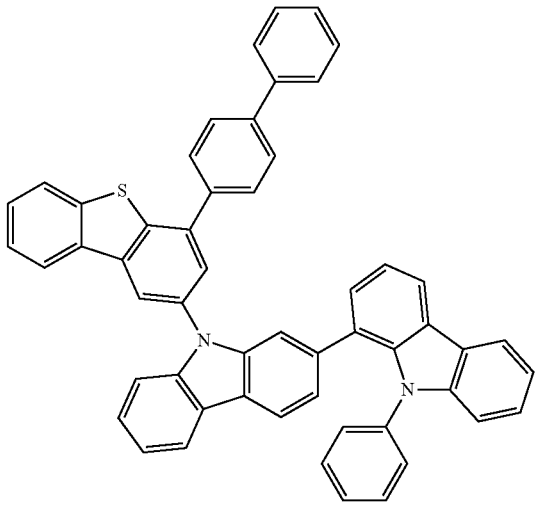
59
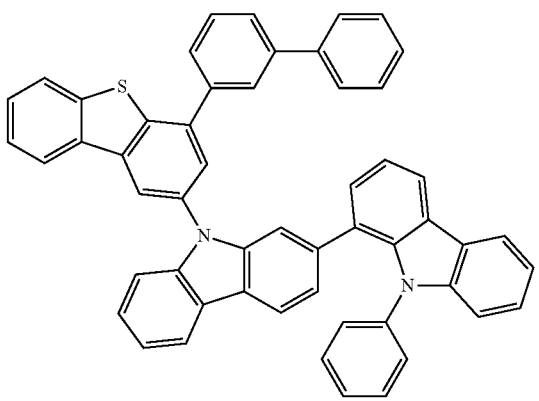
60
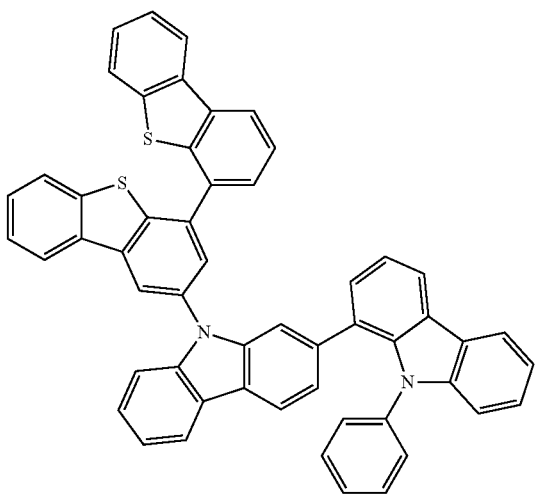

61
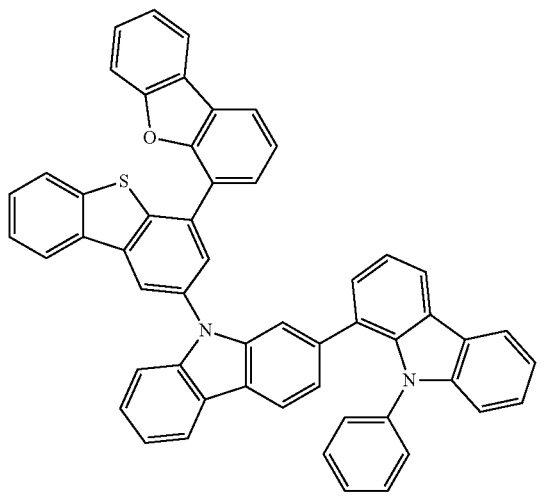
64
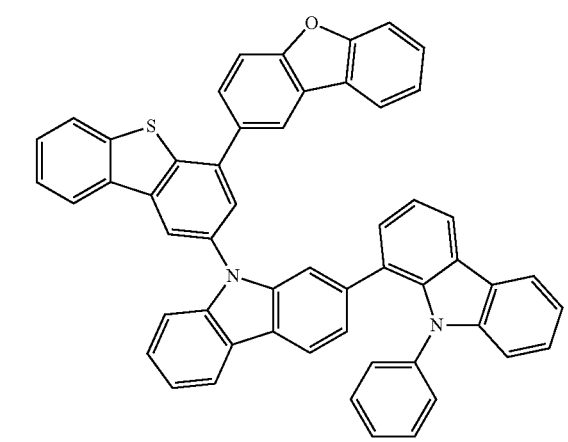
62
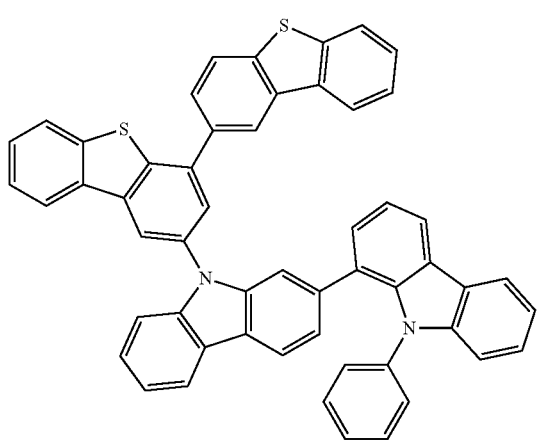
65
63
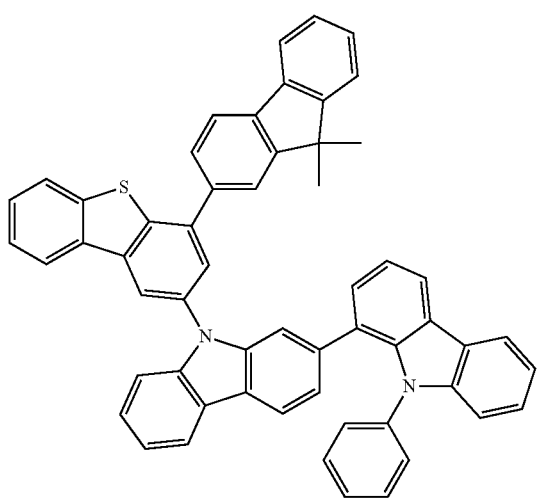
66
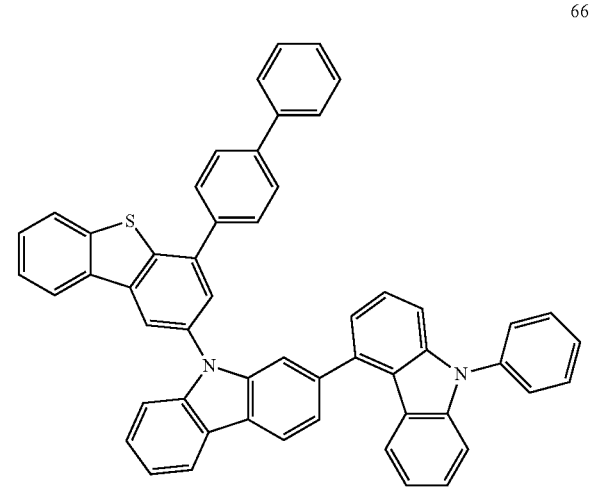

67
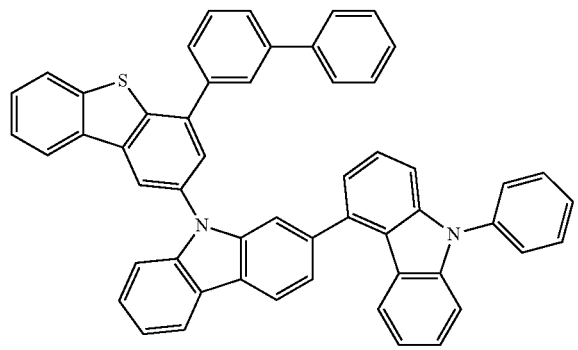
68
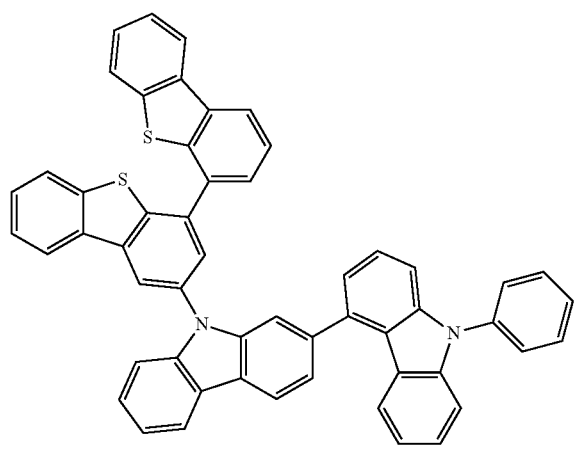
69
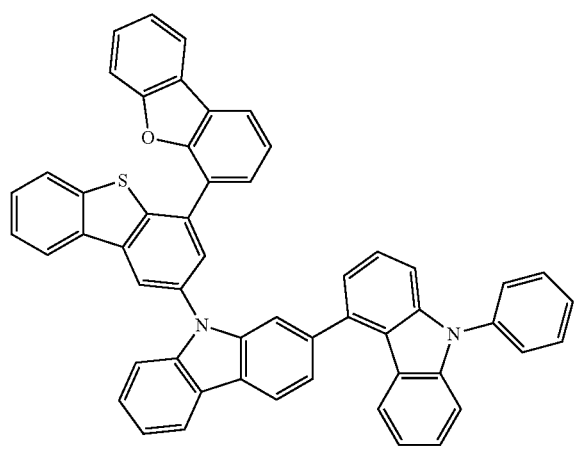
70
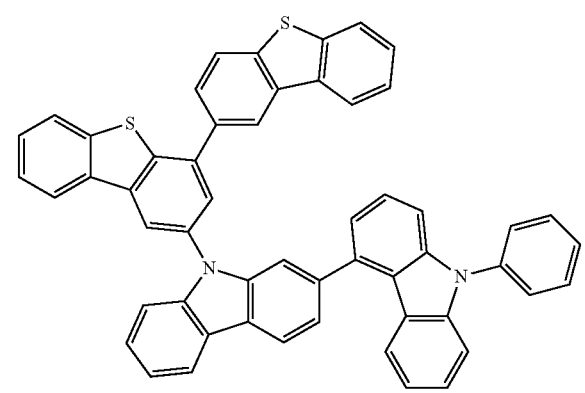
71
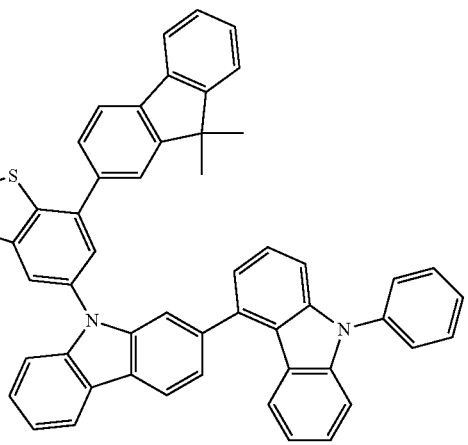
72
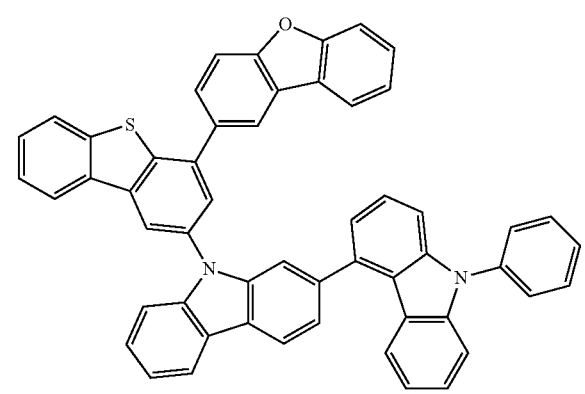

73
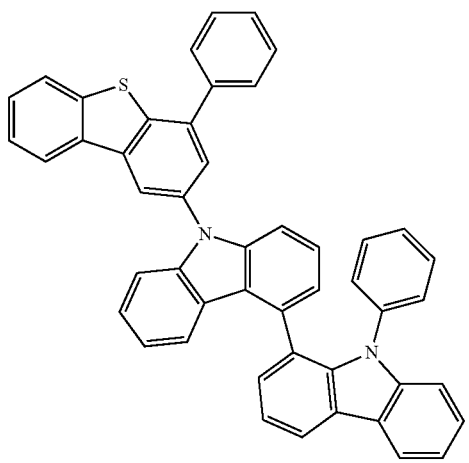
74
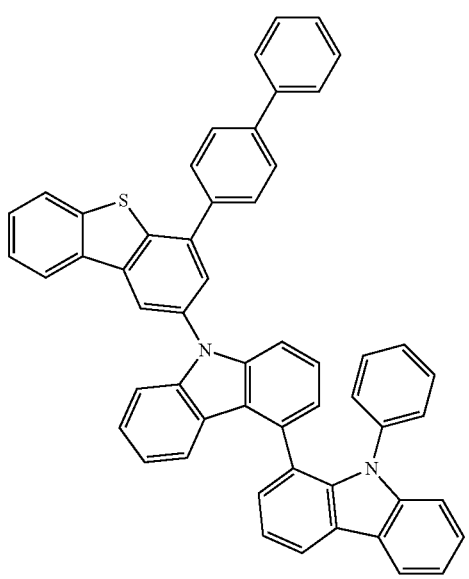
75
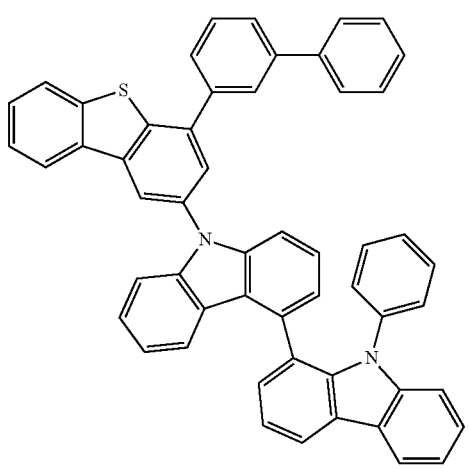
76
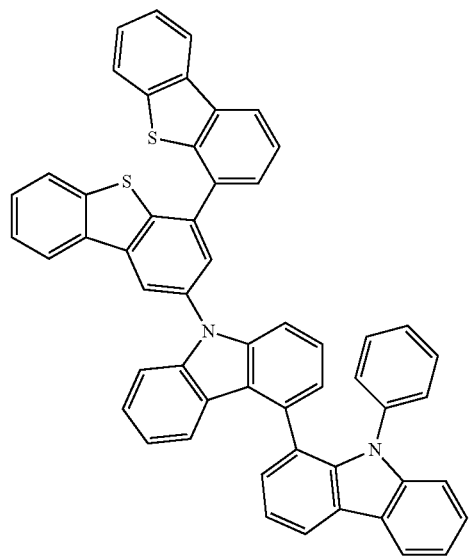
77
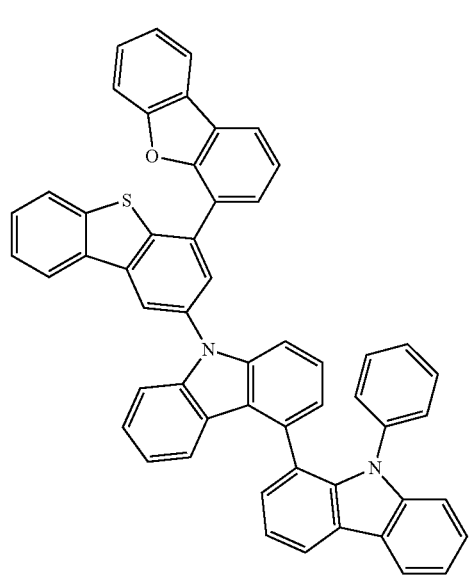
78
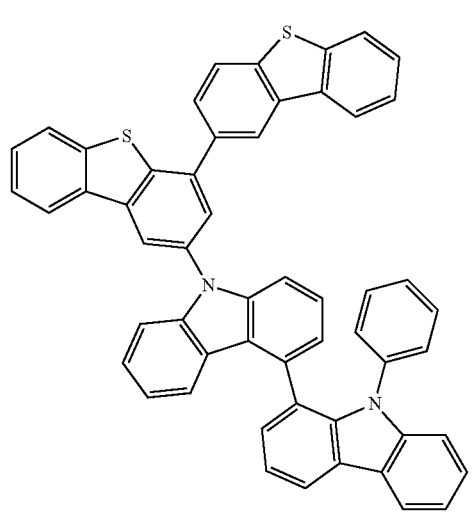

117
-continued
79
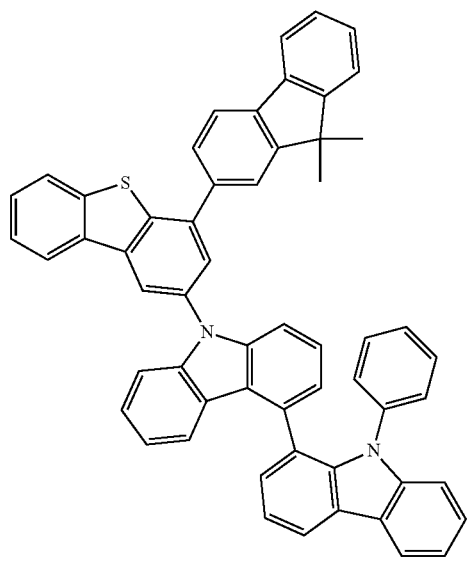
80
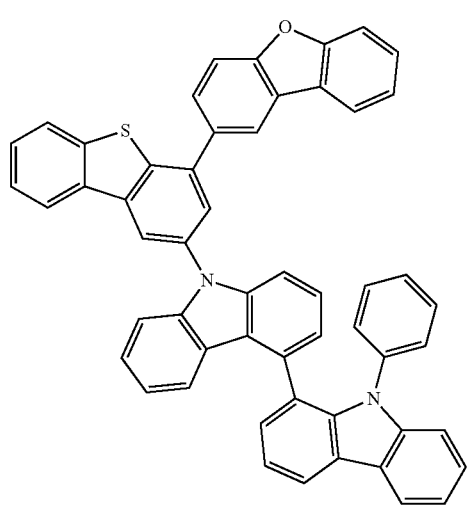
81
118
-continued
82
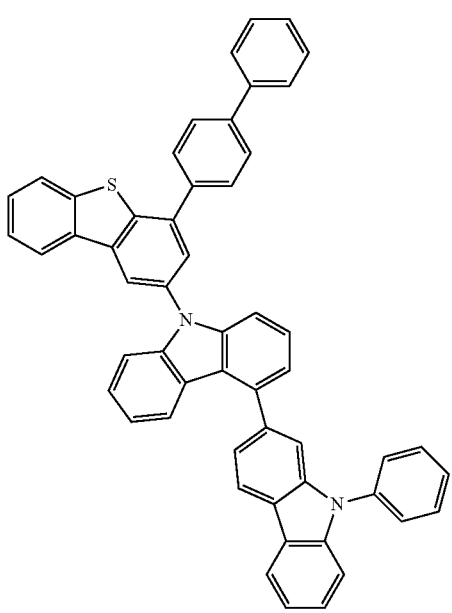
83
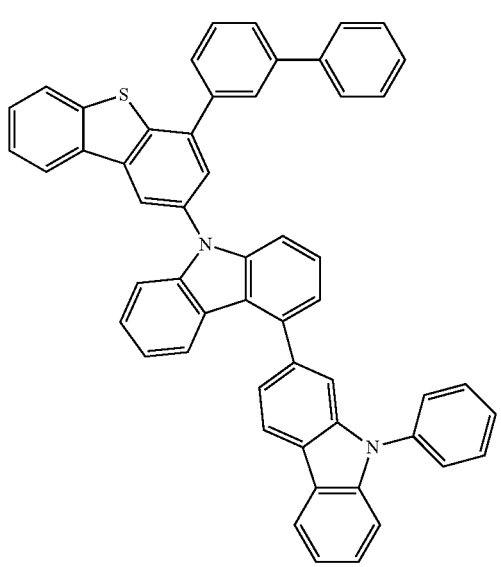

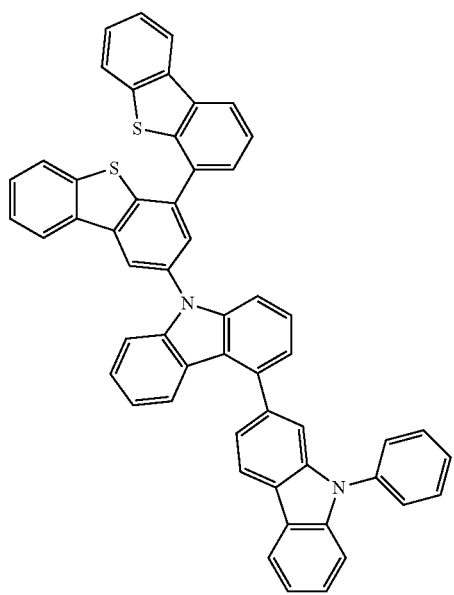
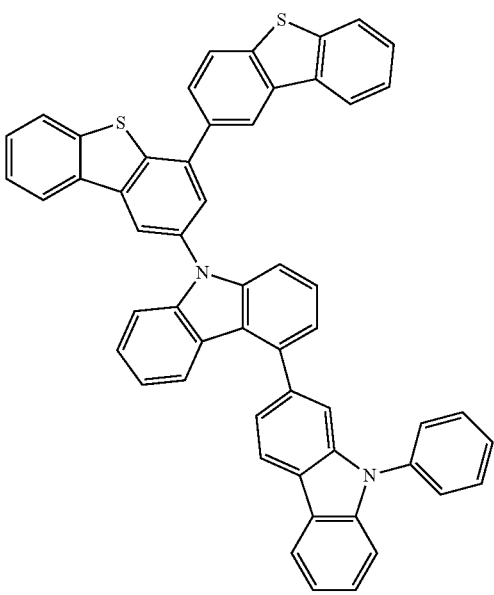
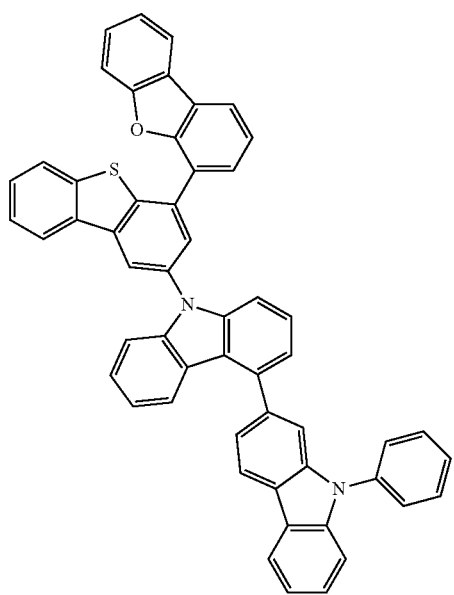

88
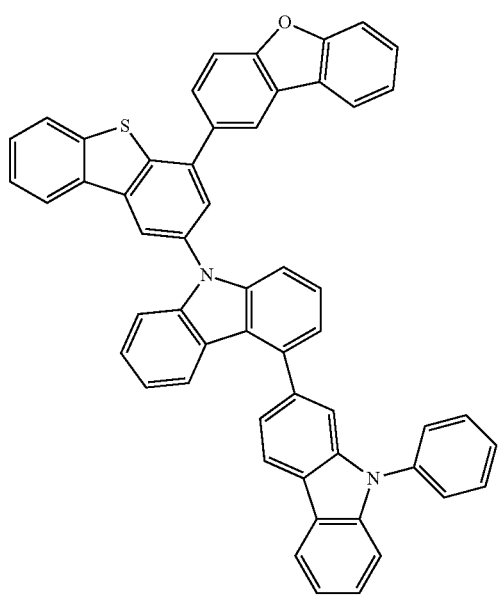
89
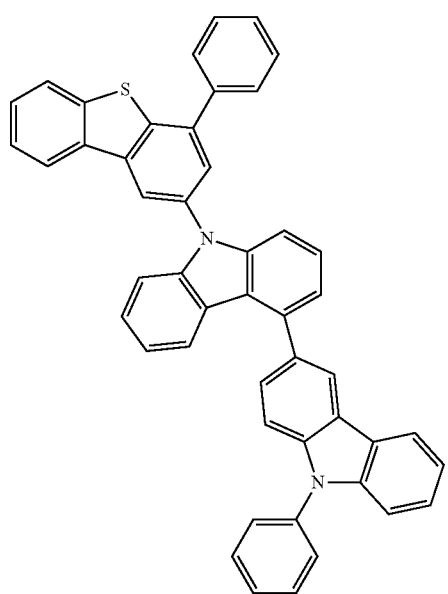
90
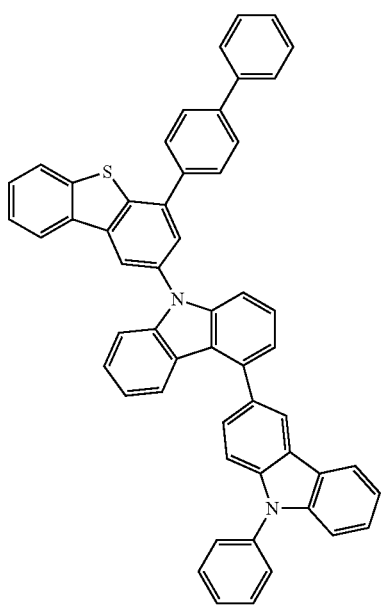
91
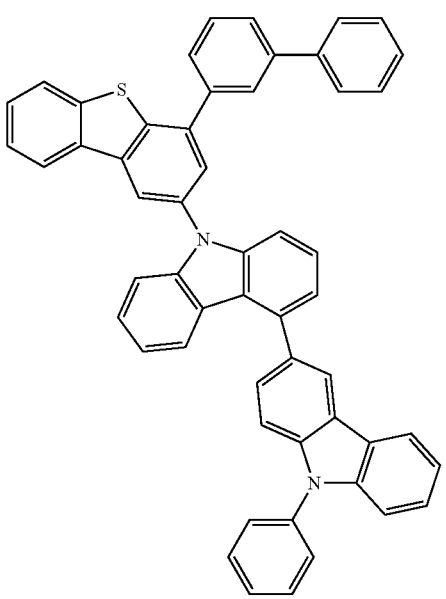

123
-continued
92
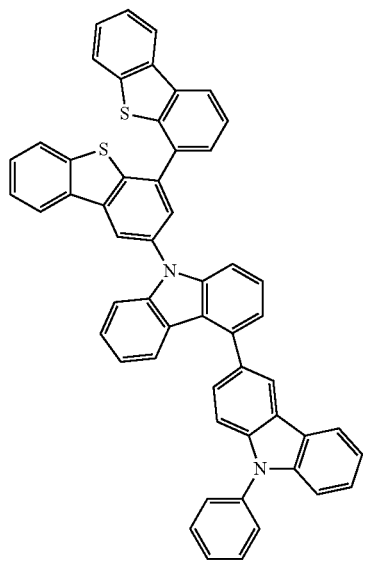
93
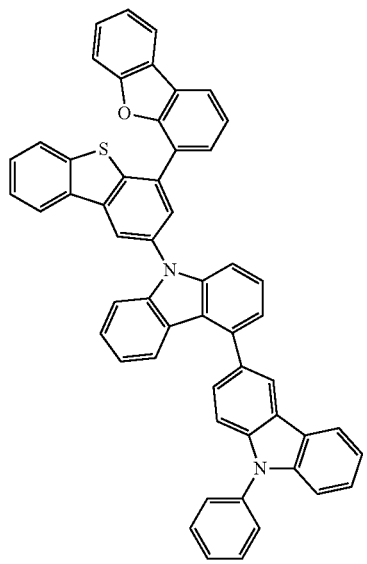
124
-continued
94
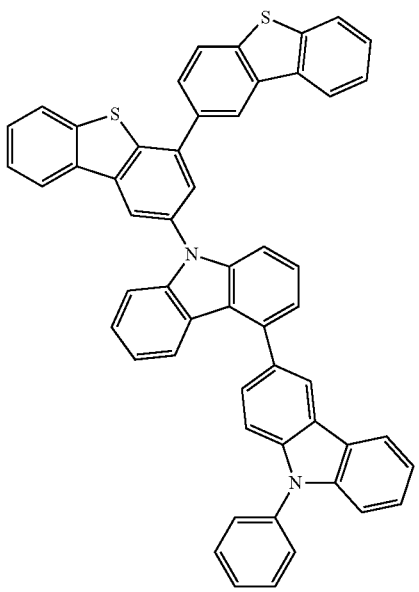
95
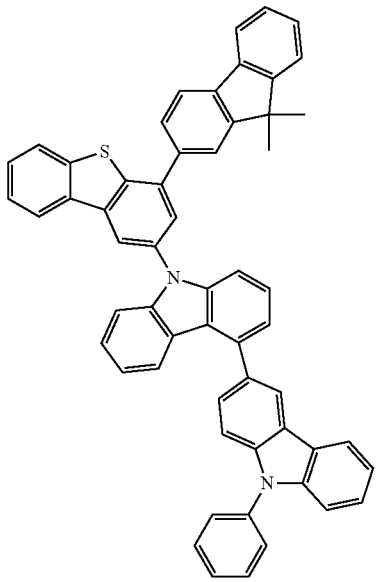

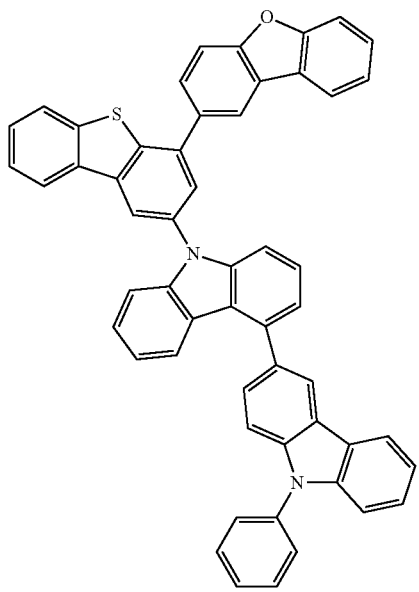
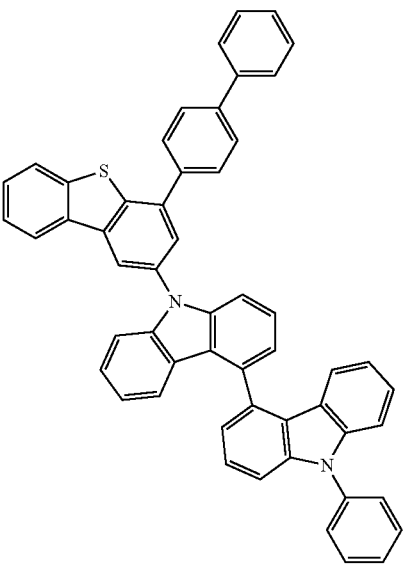

127
-continued
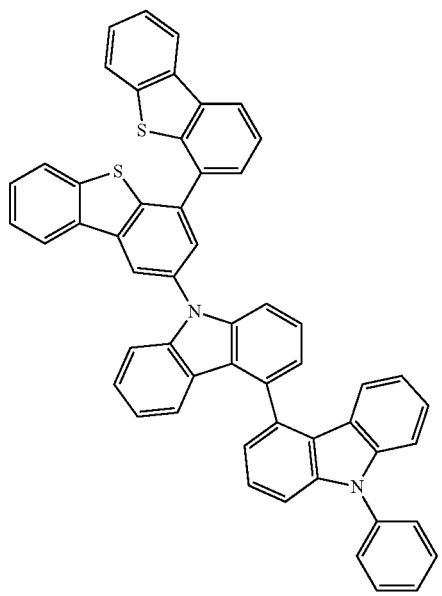
100
128
-continued
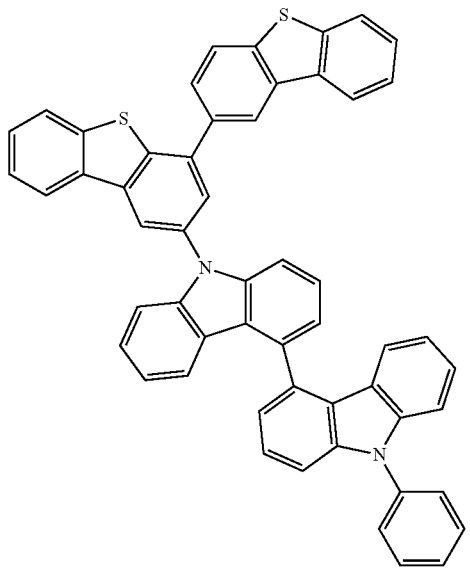
102
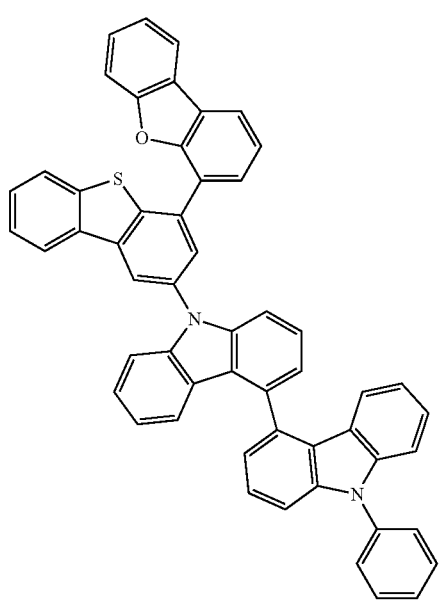
101
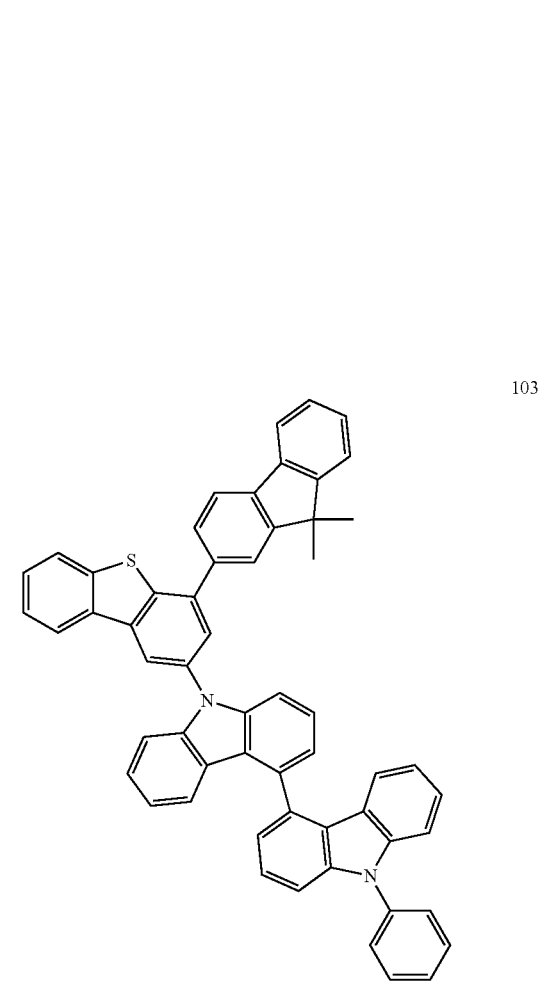
103

-continued

104

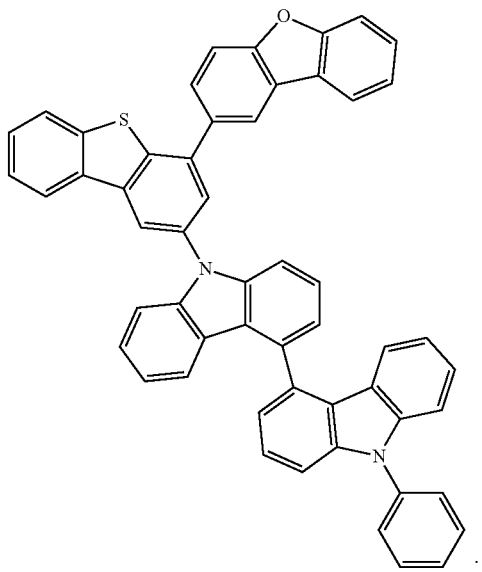

7. An organic light emitting device comprising:
a positive electrode;
a negative electrode; and
an organic material layer having one or more layers disposed between the positive electrode and the negative electrode,
wherein one or more layers of the organic material layer comprise the hetero-cyclic compound of claim 1.

8. The organic light emitting device of claim 7, wherein the organic material layer comprises at least one layer of a hole blocking layer, an electron injection layer, and an electron transporting layer, and at least one layer of the hole blocking layer, the electron injection layer, and the electron transporting layer comprises the hetero-cyclic compound.

9. The organic light emitting device of claim 7, wherein the organic material layer comprises a light emitting layer, and the light emitting layer comprises the hetero-cyclic compound.

10. The organic light emitting device of claim 7, wherein the organic material layer comprises one or more layers of a hole injection layer, a hole transporting layer, and a layer which injects and transports holes simultaneously, and one layer of the layers comprises the hetero-cyclic compound.

* * * * *